US012686712B2

(12) United States Patent
Figueiredo et al.

(10) Patent No.: US 12,686,712 B2
(45) Date of Patent: Jul. 21, 2026

(54) ANTIBODY, RELATED USE, PHARMACEUTICAL COMPOSITION INCLUDING METHOD FOR DIAGNOSING FUNGAL INFECTIONS, FUNGAL INFECTION DIAGNOSIS KIT AND METHOD FOR TREATING FUNGAL INFECTIONS

(71) Applicant: Fundação Oswaldo Cruz, Rio de Janeiro (BR)

(72) Inventors: Alexandre Bezerra Conde Figueiredo, Rio de Janeiro (BR); Marcio Lourenco Rodrigues, Curitiba (BR); Fernando de Paiva Conte, Rio de Janeiro (BR); Fernanda Lopes Fonseca, Rio de Janeiro (BR); Marcia Arissawa, Niterói (BR)

(73) Assignee: FUNDAÇÃO OSWALDO CRUZ, Rio de Janeiro (BR)

( * ) Notice: Subject to any disclaimer, the term of this patent is extended or adjusted under 35 U.S.C. 154(b) by 732 days.

(21) Appl. No.: 17/796,661

(22) PCT Filed: Jan. 12, 2021

(86) PCT No.: PCT/BR2021/050007
§ 371 (c)(1),
(2) Date: Jul. 31, 2022

(87) PCT Pub. No.: WO2021/151180
PCT Pub. Date: Aug. 5, 2021

(65) Prior Publication Data
US 2024/0262897 A1 Aug. 8, 2024

(30) Foreign Application Priority Data
Jan. 31, 2020 (BR) .................... BR102020002165-6

(51) Int. Cl.
| | |
|---|---|
| *C07K 16/14* | (2006.01) |
| *A61K 39/395* | (2006.01) |
| *G01N 33/53* | (2006.01) |
| *G01N 33/569* | (2006.01) |
| *G01N 33/577* | (2006.01) |

(52) U.S. Cl.
CPC .......... *C07K 16/14* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 3,654,090 | A | 4/1972 | Schuurs et al. |
| 3,850,752 | A | 11/1974 | Schuurs et al. |
| 4,016,043 | A | 4/1977 | Schuurs et al. |
| 4,342,566 | A | 8/1982 | Theofilopoulos et al. |
| 4,816,397 | A | 3/1989 | Boss et al. |
| 4,816,567 | A | 3/1989 | Cabilly et al. |
| 5,225,539 | A | 7/1993 | Winter |
| 5,530,101 | A | 6/1996 | Queen et al. |
| 5,545,806 | A | 8/1996 | Lonberg et al. |
| 5,569,825 | A | 10/1996 | Lonberg et al. |
| 5,585,089 | A | 12/1996 | Queen et al. |
| 5,859,205 | A | 1/1999 | Adair et al. |
| 5,922,545 | A | 7/1999 | Mattheakis et al. |
| 6,075,181 | A | 6/2000 | Kucherlapati et al. |
| 6,111,166 | A | 8/2000 | van de Winkel |
| 6,150,584 | A | 11/2000 | Kucherlapati et al. |
| 6,200,951 | B1 | 3/2001 | Gray et al. |
| 6,207,418 | B1 | 3/2001 | Hori et al. |
| 6,797,492 | B2 | 9/2004 | Daugherty et al. |

FOREIGN PATENT DOCUMENTS

| | | |
|---|---|---|
| EP | 0120694 A2 | 10/1984 |
| EP | 0125023 A1 | 11/1984 |
| KR | 2005-0096499 | 10/2005 |
| WO | 9014837 A1 | 12/1990 |
| WO | 9311161 A1 | 6/1993 |
| WO | 9413804 A1 | 6/1994 |

OTHER PUBLICATIONS

Ward et al. "Binding Activities Of A Repertoire Of Single Immunoglobulin Variable Domains Secreted From *Escherichia coli*" Nature, 3416242): 544-546, Oct. 12, 1989. (3 Pages).
International Search Report and the Written Opinion Dated Sep. 10, 2021 From the International Searching Authority Re. Application No. PCT/BR2021/050007 (12 Pages).
Albengres et al. "Systemic Antifungal Agents", Drug Safety, 18(2): 83-97, Feb. 1998.
Coelho et al. "Chapter One—The Tools for Virulence of Cryptococcus Neoformans", Advances in Applied Microbiology, 87: 1-41, 2014.
Database Genbank "Iimmunoglobulin Kappa Light Chain Variable Region, partial [Mus,musculus ]", Database Genbank [Online] AMN89630.1 , Database Accession No. AMN89630, Mar. 9, 2016. (2 Pages).
Database Genbank "Immunoglobulin Heavy Chain Variable Region, Partial [Mus,musculus]", Database Genbank [Online] AAO19669.1, Database Accession No. AAO19669, Jul. 24, 2016. (2 Pages).

(Continued)

*Primary Examiner* — Ilia I Ouspenski
(74) *Attorney, Agent, or Firm* — Kilpatrick Townsend & Stockton LLP

(57) ABSTRACT

Present invention provides monoclonal antibody against chitin oligomer through hybridoma technique. Antibodies abovementioned can be used as tools to fungal infection diagnostic and treatment. Pharmaceutical compositions and fungal infection treatment kits are also disclosed, including antibodies abovementioned. Moreover, fungal infection diagnostic method is also disclosed, using antibodies abovementioned and their use in drug preparation to treat fungal infections.

10 Claims, 11 Drawing Sheets

Specification includes a Sequence Listing.

(56)             References Cited

OTHER PUBLICATIONS

Database Genbank "Immunoglobulin Light Chain Variable Region, Partial [Mus,musculus]", Database Genbank [Online] ATI 98585.1, Database Accession No. ATI 98585, Oct. 16, 2017. (2 Pages).

Fonseca et al. "A Binding of the Wheat Germ Lectin to Cryptococcus Neoformans Chitooligomers Affects Multiple Mechanisms Required for Fungal Pathogenesis", Fungal Genetics and Biology, 60:64-73, Published Online Apr. 19, 2013.

Fonseca et al. "Role for Chitin and Chitooligomers in the Capsular Architecture of Cryptococcus Neoformans", Eukaryotic Cell, 8(10):1543-1553, Oct. 2009.

Hamill "Amphotericin B Formulations: A Comparative Review of Efficacy and Toxicity", Drugs, 73(9):919-934, Jun. 1, 2013.

Kim et al. "Enzyme-Linked Immunosorbent Assay for Detection of Chitooligosaccharides", Bioscience, Biotechnology, and Biochemistry, 64(4):696-701, Jan. 2000.

Rodrigues et al. "Monoclonal Antibody to Fungal Glucosylceramide Protects Mice Against Lethal Cryptococcus Neoformans Infection" Clinical and Vaccine Immunology, 14(10):1372-1376, Oct. 2007.

Alvarez et al., Antifungal Efficacy of an Intravenous Formulation Containing Monomeric Amphotericin B, 5- Fluorocytosine, and Saline for Sodium Supplementation, Pharmaceutical Research, vol. 34, No. 5, May 2017, pp. 1115-1124.

Armstrong-James et al., A Neglected Epidemic: Fungal Infections in HIV/AIDS, Trends in Microbiology, vol. 22, No. 3, Mar. 2014, pp. 120-127.

Azab et al., Rapid Diagnosis of Invasive Fungal Infections, International Journal of Current Microbiology and Applied Sciences, vol. 4, No. 11, Nov. 2015, pp. 470-486.

Bain et al., Non-Lytic Expulsion/Exocytosis of Candida Albicans from Macrophages, Fungal Genetics and Biology, vol. 49, No. 9, Sep. 2012, pp. 677-678.

Barnes et al., Aspergillosis: Spectrum of Disease, Diagnosis, and Treatment, Infectious Disease Clinics, vol. 20, No. 3, Sep. 2006, pp. 545-561.

Beenhouwer et al., Human Immunoglobulin G2 (lgG2) and IgG4, but Not IgG1 or lgG3, Protect Mice against Cryptococcus neoformans Infection, Infection and Immunity, vol. 75, No. 3, Mar. 2007, pp. 1424-1435.

Benedict et al., Emerging Issues, Challenges, and Changing Epidemiology of Fungal Disease Outbreaks, The Lancet Infectious Diseases, vol. 17, No. 12, Dec. 2017, pp. e403-e411.

Bird et al., Single-chain Antigen-Binding Proteins, Science, vol. 242, No. 4877, Oct. 21, 1988, pp. 423-426.

Bongomin et al., Global and Multi-National Prevalence of Fungal Diseases-Estimate Precision, Journal of Fungi, vol. 3, No. 4, Oct. 18, 2017, 29 pages.

Borba et al., Cost-Effectiveness of Amphotericin B Formulations in the Treatment of Systemic Fungal Infections, Mycoses, vol. 61, No. 10, Oct. 2018, pp. 754-763.

Brena et al., Fungicidal Monoclonal Antibody C7 Binds to Candida albicans Als3, Infection and Immunity, vol. 75, No. 7, Jul. 2007, pp. 3680-3682.

Brown et al., Hidden Killers: Human Fungal Infections, Science Translational Medicine, vol. 4, No. 165, Dec. 19, 2012, pp. 1-9.

Buissa-Filho et al., The Monoclonal Antibody against the Major Diagnostic Antigen of Paracoccidioides brasiliensis Mediates Immune Protection in Infected BALB/c Mice Challenged Intratracheally with the Fungus, Infection and Immunity, vol. 76, No. 7, Jul. 2008, pp. 3321-3328.

Buitrago et al., Efficacy of DNA Amplification in Tissue Biopsy Samples to Improve the Detection of Invasive Fungal Disease, Clinical Microbiology and Infection, vol. 19, No. 6, Jun. 2013, pp. E271-E277.

Campuzano et al., Innate Immunity against Cryptococcus, from Recognition to Elimination, Journal of Fungi, vol. 4, No. 1, Mar. 7, 2018, pp. 1-22.

Casadevall et al., A New Synthesis for Antibody-Mediated Immunity, Nature Immunology, vol. 13, No. 1, Dec. 16, 2011, pp. 21-28.

Casadevall et al., Accidental Virulence, Cryptic Pathogenesis, Martians, Lost Hosts, and the Pathogenicity of Environmental Microbes, Eukaryotic Cell, vol. 6, No. 12, Dec. 2007, pp. 2169-2174.

Casadevall et al., Immunoglobulins in Defense, Pathogenesis and Therapy of Fungal Diseases, Cell Host Microbe, vol. 11, No. 5, May 17, 2012, pp. 447-456.

Chayakulkeeree et al., Cryptococcosis, Infectious Disease Clinics, vol. 20, 2006, pp. 507-544.

Colombo et al., Fungal Colonization of the Brain: Anatomopathological Aspects of Neurological Cryptococcosis, Annals of the Brazilian Academy of Sciences, vol. 87, Aug. 2015, pp. 1293-1309.

Denning et al., Itraconazole Resistance in Aspergillus fumigatus, Antimicrobial Agents and Chemotherapy, vol. 41, No. 6, Jun. 1997, pp. 1364-1368.

Dos Santos, Advances and Challenges in Therapeutic Monoclonal Antibodies Drug Development, Brazilian Journal of Pharmaceutical Sciences, vol. 54, Nov. 8, 2018, pp. 2-15.

Dutra et al., Warfare and Defense: The Host Response to Cryptococcus Infection, Fungal Biology Reviews, vol. 32, No. 2, Mar. 2018, pp. 35-51.

Eastman et al., Cryptococcal Heat Shock Protein 70 Homolog Ssa1 Contributes to Pulmonary Expansion of Cryptococcus neoformans during the Afferent Phase of the Immune Response by Promoting Macrophage M2 Polarization, The Journal of Immunology, vol. 194, No. 12, Jun. 15, 2015, pp. 5999-6010.

Elsegeiny et al., Immunology of Cryptococcal Infections: Developing a Rational Approach to Patient Therapy, Frontiers in Immunology, vol. 9, Apr. 4, 2018, pp. 1-9.

Erwig et al., Interactions of Fungal Pathogens with Phagocytes, Nature Reviews Microbiology, vol. 14, Mar. 2016, pp. 163-176.

Fesel et al., B-Glucan: Crucial Component of the Fungal Cell Wall and Elusive MAMP in Plants, Fungal Genetics and Biology, vol. 90, May 2016, pp. 53-60.

Fisher et al., Independent Contribution of Bronchoalveolar Lavage and Serum Galactomannan in the Diagnosis of Invasive Pulmonary Aspergillosis, Transplant Infectious Disease, vol. 16, No. 3, Jun. 2014, pp. 505-510.

Guimaraes et al., Monoclonal Antibodies to Heat Shock Protein 60 Alter the Pathogenesis of Histoplasma capsulatum, Infection and Immunity, vol. 77, No. 4, Apr. 2009, pp. 1357-1367.

Guimaraes et al., Surface Architecture of Histoplasma capsulatum, Frontiers in Microbiology, vol. 2, Nov. 18, 2011, pp. 1-14.

Hagen et al., Recognition of Seven Species in the Cryptococcus gattii/Cryptococcus neoformans Species Complex, Fungal Genetics and Biology, vol. 78, May 2015, pp. 16-48.

Harris et al., Cryptococcus gattii in the United States: Clinical Aspects of Infection With an Emerging Pathogen, Clinical Infectious Diseases, vol. 53, No. 12, Dec. 15, 2011, pp. 1188-1195.

Harris et al., Cryptococcus gattii Infections in Multiple States Outside the US Pacific Northwest, Emerging Infectious Diseases, vol. 19, No. 10, Oct. 2013, pp. 1620-1626.

Heitman, Microbial Pathogens in the Fungal Kingdom, Fungal Biology Reviews, vol. 25, No. 1, Mar. 1, 2011, pp. 48-60.

Holliger et al., "Diabodies": Small Bivalent and Bispecific Antibody Fragments, Proceedings of the National Academy of Sciences, vol. 90, No. 14, Jul. 15, 1993, pp. 6444-6448.

Hoogenboom et al., Antibody Phage Display Technology and Its Applications, Immunotechnology, vol. 4, No. 1, Jun. 1998, pp. 1-20.

Hoogenboom, Designing and Optimizing Library Selection Strategies for Generating High-Affinity Antibodies, Trends in Biotechnology, vol. 15, No. 2, Feb. 1997, pp. 62-70.

Huang et al., Evaluation of a New Cryptococcal Antigen Lateral Flow Immunoassay in Serum, Cerebrospinal Fluid and Urine for the Diagnosis of Cryptococcosis: A Meta-Analysis and Systematic Review, Public Library of Science One, vol. 10, No. 5, May 14, 2015, pp. 1-10.

Jaijakul et al., (1,3)-B-D-Glucan as a Prognostic Marker of Treatment Response in Invasive Candidiasis, Clinical Infectious Diseases, vol. 55, No. 4, Aug. 15, 2012, pp. 521-526.

Kaplon et al., Antibodies to Watch in 2019, mAbs, vol. 11, No. 2, Feb. 2019, pp. 219-238.

Kauffman, Histoplasmosis: a Clinical and Laboratory Update, Clinical Microbiology Reviews, vol. 20, No. 1, Jan. 2007, pp. 115-132.

(56)             References Cited

OTHER PUBLICATIONS

King, Applications and Engineering of Monoclonal Antibodies, Chemical Rubber Company Press, Nov. 27, 1998, 79 pages.

Kohler et al., Continuous Cultures of Fused Cells Secreting Antibody of Predefined Specificity, Nature, vol. 256, No. 5517, Aug. 7, 1975, pp. 495-497.

Kohler et al., The Spectrum of Fungi That Infects Humans, Cold Spring Harbor Perspectives in Medicine, vol. 5, Jan. 2015, pp. 1-23.

Kontoyiannis, Antifungal Resistance: An Emerging Reality and A Global Challenge, The Journal of Infectious Diseases, vol. 216, Aug. 15, 2017, pp. S431-S435.

Kozel et al., Fungal Diagnostics, Cold Spring Harbor Perspectives in Medicine, vol. 4, No. 4, Apr. 2014, pp. 1-14.

Kurtz et al., Lipopeptide Inhibitors of Fungal Glucan Synthase, Journal of Medical & Veterinary Mycology, vol. 35, Mar. 1, 1997, pp. 79-86.

Kwon-Chung et al., Cryptococcus neoformans and Cryptococcus gattii, the Etiologic Agents of Cryptococcosis, Cold Spring Harbor Perspectives in Medicine, vol. 4, Jul. 2014, pp. 1-27.

Kwon-Chung et al., The Case for Adopting the "Species Complex" Nomenclature for the Etiologic Agents of Cryptococcosis, MSphere, vol. 2, No. 1, Jan. 11, 2017, pp. 1-7.

Lamoth, Galactomannan and 1,3-3-D-Glucan Testing for the Diagnosis of Invasive Aspergillosis, Journal of Fungi, vol. 2, No. 3, Jul. 2016, pp. 1-8.

Leach et al., Surviving the Heat of the Moment: A Fungal Pathogens Perspective, Public Library of Science Pathogens, vol. 9, No. 3, Mar. 7, 2013, pp. 1-4.

Lemke et al., Amphotericin B, Applied Microbiology and Biotechnology, vol. 68, Apr. 9, 2005, pp. 151-162.

Lin, Cryptococcus neoformans: Morphogenesis, Infection, and Evolution, Infection, Genetics and Evolution, vol. 9, No. 4, Jul. 2009, pp. 401-416.

Lin et al., The Biology of the Cryptococcus neoformans Species Complex, Annual Review of Microbiology, vol. 60, Oct. 2006, pp. 69-105.

Liu et al., Molecular Mechanisms of Cryptococcal Meningitis, Virulence, vol. 3, No. 2, Mar. 1, 2012, pp. 173-181.

Martinez et al., Antibody to Cryptococcus neoformans Glucuronoxylomannan Inhibits the Release of Capsular Antigen, Infection and Immunity, vol. 72, No. 6, Jun. 2004, pp. 3674-3679.

Martinez et al., Specific Antibody Can Prevent Fungal Biofilm Formation and This Effect Correlates with Protective Efficacy, Infection and Immunity, vol. 73, No. 10, Oct. 2005, pp. 6350-6362.

Meya et al., Serum Cryptococcal Antigen (CRAG) Screening is a Cost-Effective Method to Prevent Death in HIV- Infected Persons with CD4 ≤100/uL Starting HIV Therapy in Resource-Limited Settings, Clinical Infectious Diseases, vol. 51, No. 4, Aug. 15, 2010, pp. 448-455.

Moragues et al., A Monoclonal Antibody Directed against a Candida albicans Cell Wall Mannoprotein Exerts Three Anti-C. albicans Activities, Infection and Immunity, vol. 71, No. 9, Sep. 2003, pp. 5273-5279.

Mukherjee et al., Combination Treatment of Invasive Fungal Infections, Clinical Microbiology Reviews, vol. 18, No. 1, Jan. 1, 2005, pp. 163-194.

Nguyen et al., Performance of Candida Real-Time Polymerase Chain Reaction, B-D-Glucan Assay, and Blood Cultures in the Diagnosis of Invasive Candidiasis, Clinical Infectious Diseases, vol. 54, No. 9, May 1, 2012, pp. 1240-1248.

Nicola et al., Nonlytic Exocytosis of Cryptococcus neoformans from Macrophages Occurs In Vivo and Is Influenced by Phagosomal pH, mBio, vol. 2, No. 4, Aug. 9, 2011, pp. 1-9.

Nosanchuk et al., Antibodies to a Cell Surface Histone-Like Protein Protect Against Histoplasma Capsulatum, Journal of Clinical Investigation, vol. 112, No. 8, Oct. 2003, pp. 1164-1175.

Nucci et al., Emerging Fungal Diseases, Clinical Infectious Diseases, vol. 41, No. 4, Aug. 15, 2005, pp. 521-526.

Odds et al., Antifungal Agents: Mechanisms of Action, Trends in Microbiology, vol. 11, No. 6, Jun. 2003, pp. 272-279.

Onishi et al., Diagnostic Accuracy of Serum 1,3-3-D-Glucan for Pneumocystis jiroveci Pneumonia, Invasive Candidiasis, and Invasive Aspergillosis: Systematic Review and Meta-Analysis, Journal of Clinical Microbiology, vol. 50, No. 1, Jan. 1, 2012, pp. 7-15.

Ostermann et al., Cost Analysis of Voriconazole Versus Liposomal Amphotericin B for Primary Therapy of Invasive Aspergillosis among Patients with Haematological Disorders in Germany and Spain, BioMed Central Pharmacology and Toxicology, vol. 15, Sep. 24, 2014, pp. 1-8.

Pande et al., Phage Display: Concept, Innovations, Applications and Future, Biotechnology Advances, vol. 28, No. 6, Nov. 2010, pp. 849-858.

International Application No. PCT/BR2021/050007, International Preliminary Report on Patentability mailed on Jan. 29, 2022, 15 pages.

Polvi et al., Opportunistic Yeast Pathogens: Reservoirs, Virulence Mechanisms, And Therapeutic Strategies, Cellular and Molecular Life Sciences, vol. 72, Feb. 21, 2015, pp. 2261-2287.

Posch et al., Promising Immunotherapy Against Fungal Diseases, Expert Opinion on Biological Therapy, vol. 17, No. 7, Jul. 2017, pp. 861-870.

Power et al., Synthesis of High Avidity Antibody Fragments (scFv Multimers) For Cancer Imaging, Journal of Immunological Methods, vol. 242, Aug. 28, 2000, pp. 193-204.

Powers-Fletcher et al., Nonculture Diagnostics in Fungal Disease, Infectious Disease Clinics, vol. 30, No. 1, Mar. 2016, pp. 37-49.

Rachini et al., An Anti-B-Glucan Monoclonal Antibody Inhibits Growth and Capsule Formation of Cryptococcus neoformans In Vitro and Exerts Therapeutic, Anticryptococcal Activity In Vivo, Infection and Immunity, vol. 75, No. 11, Nov. 2007, pp. 5085-5094.

Rajasingham et al., Global Burden of Disease of HIV-Associated Cryptococcal Meningitis: An Updated Analysis, The Lancet Infectious Diseases, vol. 17, No. 8, Aug. 2017, pp. 873-881.

Ramanan et al., Laboratory Diagnostics for Fungal Infections: A Review of Current and Future Diagnostic Assays, Clinics in Chest Medicine, vol. 38, No. 3, Sep. 2017, pp. 535-554.

Rampini et al., Similar Efficacy of Broad-Range Its Pcr And Conventional Fungal Culture for Diagnosing Fungal Infections in Non-Immunocompromised Patients, BioMed Central Microbiology, vol. 16, Jun. 28, 2016, pp. 1-8.

Rivera et al., Antibody-Mediated Protection against Cryptococcus neoformans Pulmonary Infection Is Dependent on B Cells, Infection and Immunity, vol. 73, No. 2, Feb. 2005, pp. 1141-1150.

Rodrigues, The Multifunctional Fungal Ergosterol, American Society for Microbiology, vol. 9, No. 5, Sep. 18, 2018, pp. 1-5.

Roemer et al., Antifungal Drug Development: Challenges, Unmet Clinical Needs, and New Approaches, Cold Spring Harbor Perspectives in Medicine, vol. 4, No. 5, May 2014, pp. 1-14.

Saeed et al., The Preparation and Identification of a Monoclonal Antibody against Domoic Acid and Establishment of Detection by Indirect Competitive ELISA, Toxins, vol. 9, No. 8, Aug. 17, 2017, pp. 1-16.

Schwartz et al., Advances in the Diagnosis and Treatment of Fungal Infections of the CNS, Lancet Neurology, vol. 17, Apr. 2018, pp. 362-372.

Scorzoni et al., Antifungal Therapy: New Advances in the Understanding and Treatment of Mycosis, Frontiers in Microbiology, vol. 8, Jan. 13, 2017, pp. 1-23.

Singh et al., Aspergillus Infections in Transplant Recipients, Clinical Microbiology Reviews, vol. 18, No. 1, Jan. 1, 2005, pp. 44-69.

Smulian et al., Immunization With Recombinant Pneumocystis carinii p55 Antigen Provides Partial Protection Against Infection: Characterization of Epitope Recognition Associated With Immunization, Microbes and Infection, vol. 2, No. 2, Feb. 2000, pp. 127-136.

Spitzer et al., Combinatorial Strategies for Combating Invasive Fungal Infections, Virulence, vol. 8, No. 2, Feb. 2017, pp. 169-185.

Spivak et al., Candida auris: an Emerging Fungal Pathogen, Journal of Clinical Microbiology, vol. 56, No. 2, Feb. 2018, pp. 1-10.

Steimbach et al., Efficacy and Safety of Amphotericin B Lipid-Based Formulations-A Systematic Review and Meta- Analysis, Mycoses, vol. 60, No. 3, Mar. 2017, pp. 146-154.

(56) References Cited

OTHER PUBLICATIONS

Sulahian et al., Use and Limits of (1-3)-B-D-Glucan Assay (Fungitell), Compared to Galactomannan Determination (Platelia Aspergillus), for Diagnosis of Invasive Aspergillosis, Journal of Clinical Microbiology, vol. 52, No. 7, Jul. 2014, pp. 2328-2333.

Theel et al., B-D-Glucan Testing is Important for Diagnosis of Invasive Fungal Infections, Journal of Clinical Microbiology, vol. 51, No. 11, Nov. 2013, pp. 3478-3483.

Thorn et al., PharmGKB Summary: Fluoropyrimidine Pathways, Pharmacogenet Genomics, vol. 21, No. 4, Apr. 2011, pp. 237-242.

Torosantucci et al., Protection by Anti-B-Glucan Antibodies is Associated with Restricted B-1,3 Glucan Binding Specificity and Inhibition of Fungal Growth and Adherence, Public Library of Science, vol. 4, No. 4, Apr. 2009, pp. 1-17.

Vallabhaneni et al., The Global Burden of Fungal Diseases, Infectious Disease Clinics, vol. 30, No. 1, Mar. 2016, pp. 1-11.

Vandeputte et al., Antifungal Resistance and New Strategies to Control Fungal Infections, International Journal of Microbiology, vol. 2012, Dec. 1, 2011, pp. 1-26.

Wager et al., Cryptococcus and Phagocytes: Complex Interactions that Influence Disease Outcome, Frontiers in Microbiology, vol. 7, Feb. 9, 2016, pp. 1-16.

Wager et al., STAT1 Signaling is Essential for Protection against Cryptococcus neoformans Infection in Mice, The Journal of Immunology, vol. 193, No. 8, Oct. 15, 2014, pp. 4060-4071.

Zeller et al., Detection of Fungal Pathogens by a New Broad Range Real-Time PCR Assay Targeting the Fungal ITS2 Region, Journal of Medical Microbiology, vol. 66, No. 10, Oct. 1, 2017, pp. 1383-1392.

Zotchev, Polyene Macrolide Antibiotics and their Applications in Human Therapy, Current Medicinal Chemistry, vol. 10, No. 3, Feb. 1, 2003, pp. 211-223.

Proteins

β-Glucans

Chitin

Lipid bilayer

β-Glucan Synthase

Fungal Cell

DNA
RNA flucytosine

Ergosterol

Azoles

Lanosterol

AmB

Echinocandin

Antigen

Spleenocytes producing
the antibody of interest

Fusion

Myeloma Lineage

Fused and unfused cells

Selection in specific medium

Only fused cells
(hybridomas) grow

Hybridoma producing
Antibody of interest

Figure 10
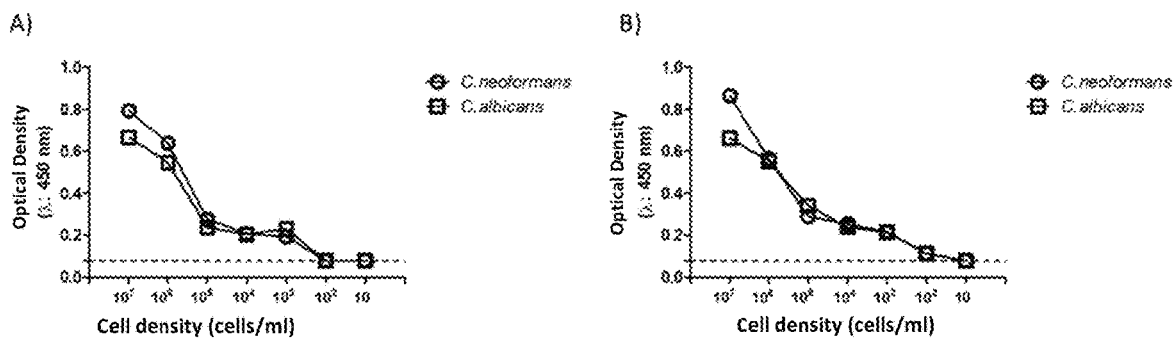
Figure 11
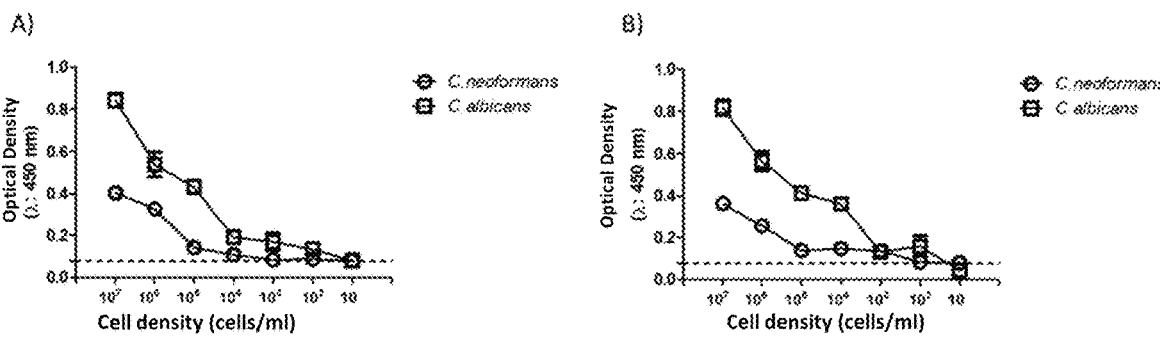
Figure 12

A)

B)

Melanization HC6/DD11

C)

Melanization AF1/CC5

ANTIBODY, RELATED USE, PHARMACEUTICAL COMPOSITION INCLUDING METHOD FOR DIAGNOSING FUNGAL INFECTIONS, FUNGAL INFECTION DIAGNOSIS KIT AND METHOD FOR TREATING FUNGAL INFECTIONS

RELATED APPLICATIONS

This application is a National Phase of PCT Patent Application No. PCT/BR2021/050007 having International filing date of Jan. 12, 2021, which claims the benefit of priority of Brazil Patent Application No. BR10 2020 002165-6 filed on Jan. 31, 2020. The contents of the above applications are all incorporated by reference as if fully set forth herein in their entirety.

SEQUENCE LISTING STATEMENT

The ASCII file, entitled 93329SequenceListing.txt, created on Jul. 29, 2022, comprising 8,682 bytes, submitted concurrently with the filing of this application is incorporated herein by reference.

FIELD AND BACKGROUND OF THE INVENTION

The present invention refers to diagnostic medicine, biotechnology and biodrug field. Specifically, the present invention refers to monoclonal antibodies to therapeutic use against fungal infections, as well as fungal infection diagnostic application in any human or animal individual.

Fungi are eukaryotic and saprophyte organisms with a rigid cellular wall that comprise around 5 million species in the planet (1). Compared to plants, that are also eukaryotic cells, including cellular wall, the difference that fungal cells have cellular walls that contain chitin, unlike plant cells, that contain cellulose, shall be highlighted.

Fungi present a major morphological diversity, including two main morphotypes: yeast, round, oval or spheric unicellular shapes, and filaments, which have hypha shape and are multicellular. Yeasts are cells that reproduce by single or multiple budding. Filament fungi have basic morphology to hypha, that can be septet or non-septet. Dimorphic fungi existence shall be highlighted, which can live in yeast shape and hypha shape, relying on environmental variations that guide transition between morphological states.

Fungi Kingdom is divided into four phyla: Ascomycota, Basidiomycota, Zygomycota and Chitridiomycota. Ascomycota and Basidiomycota phyla host several animal and plant pathogens, including human pathogens *Cryptococcus neoformans, Cryptococcus gattii, Candida* sp., *Aspergillus* sp., *Histoplasma capsulatum* and *Coccidioides immitis* (2)

Systemic mycoses, tables that result from invasive fungal infections (IFI), represent one of the main causes of human deaths in the world (3). According to data submitted by Global Action Fund for Fungal Infections (GAFFI), more than 300 million people of all ages experience some kind of severe fungal infection every year around the globe. It is estimated that, in this group, more than 1.6 million people will die, and such statistics are comparable to the ones observed to tuberculosis and 3 times greater than malaria.

IFI incidence increase is mostly the result of a significant increase in last decades of immunosupressive conditions, including HIV infection and immunosupression inducing drug use (4). What is more, broad spectrum antineoplasic and antibiotic use, apart from invasive medical interventions (5), also enables directly IFI increase.

Systemic mycoses can affect any host organ. Fungal disease classification in this category is dynamic and highly variable, as illustrated by the remark that species previously considered non-pathogenic are now acknowledged, including pathogens responsible for invasive mycoses (6). Such infections are very common in immunocompromised patients and are often associated to a high death rate (4). The most frequent genders engaged in systemic fungal infections include *Candida, Pneumocystis, Histoplasma, Aspergillus, Cryptococcus, Mucor, Rhizopus* and *Coccidioidomyces* (Table 1).

TABLE 1

| Global estimates and deaths related to fungal infections a year among people with HIV | | | |
|---|---|---|---|
| Fungal Infection | Annual Load | Lethality rate, if treated | Annual death rate |
| Cryptococcal Meningitis | ~1 million | >50% | ~100,000-600,000 |
| Pneumocystis Pneumonia | >400,000 | 15% with the best treatment | >200,000 |
| Disseminated Histoplasmosis | >100,000 | 15-30%, if diagnosed and treated | >80,000 |
| Chronic Pulmonary Aspergillosis | >185,000 | 15-40% at hospitals | >100,000 |
| Invasive Aspergillosis | >45,000 | 30% treated at hospitals | >30,000 |
| *T. marneffei* Infection | >8,000 | 33% | >2,000 |
| Fungal Infection in Skin and Mucosa | >10 million | <1% | <1,000 |
| Total | >11 million | | >500,000 |

Pathogen fungi to human beings exist in several natural habitats, however IFIs are usually observed in tropical and subtropical climates (7,8). It is speculated that climate change increase might have changed the disease distribution, and consequently, led to pathogen fungi appearance in new geographies (7). For instance, Northeaster United States registered 100 cases of the disease per *C. gattii* belonging to molecular type VGII, usually found in South America (9). However, this outbreak was registered in a temperate region dos EUA (10). It is worth noting that fungi have various characteristics that enable new niche adaptation and colonization, and consequently, the capacity to survive to host physiological conditions and switching between morphological states (11). The most common pathogen fungi adaptations include the capacity to grow at 37° C. (12), shape and size changes, capacity to scape from macrophages (13,14), melanizing and forming biofilm (15).

It is worth noting that species belonging to *Aspergillus, Candida, Cryptococcus* genders, and *Pneumocystis* are responsible for approximately 90% of human death cases (11). Recent global estimates register more than 11 million fungal infections associated to HIV-positive patients, resulting in more than 500 thousand annual deaths (Table 1).

According to Centers for Disease Control and Prevention (CDC, USA), fungi are the most frequently agents associated to mortality by microbial meningitis. It is estimated that around one million meningitis cases caused by fungus *C. neoformans* occur every year, resulting in more than two hundred thousand deaths 3 months upon infection (16).

Despite high mortality rate associated to different fungal infection types, therapeutic strategies recommended are almost the same ones since the 1950s, compared to bacterial infection treatments (18). Currently, there are four main antifungal drug classes: azoles, polyenes, pyrimidines and echinocandins. Several other classes, including morpholines and allylamines, are used only as topical agents, due to lower efficacy or severe adverse effects, whenever administered systematically.

However, intense and indiscriminate use of drugs belonging to such classes, enabled the selection of multiple resistant isolates to antifungal drugs (19), which despite being rare, has stood out, especially in the case of *Candida* species. The appearance of multiple resistant isolates to antifungal drugs also represents, at this time, a major global threat to public health. An example of this severe problem took place in early 2009, when a resistant *Candida* species to Fluconazole (FLC) was described in Eastern Asia, *Candida auris*. Currently, such species is widely disseminated in five continents and it is acknowledgedly described, as it has a multiple resistant profile to drugs (20).

Current gold standard meningoencephalitis treatment caused by *Cryptococcus* spp is a combination of amphotericin polyene B (AmB) with 5-flucytosine. AmB presents high nephrotoxicity and requires intravenous administration, limiting its use to regions without adequate medial infrastructure. It is estimated that a 15-day intravenous treatment with liposomal AmB costs between €10,000 and €20,000, in Europe (21) and in Brazil, and this value can reach R$250,000.00 monthly cost (Source: SUS Assisting Center to Assess Health Technologies and Excellence—CCATES).

Thus, searching for alternatives that decrease antifungal treatment adverse effects, monoclonal antibody use in fungal infection templates is considered highly promising, as it can bond with high specificity to antigens expressed in fungi in patient body fluids, and it is also key tools in clinical diagnostic field.

*Cryptococcus* gender is characterized by oval or spheric yeast cells surrounded by on capsule. Gender members belong to Basidiomycota phylum (22). *C. neoformans* and *C. gattii*, gender pathogen members, were subdivided for decades into three varieties and five serotypes based on capsular polysaccharide antigenic determinants: *C. neoformans* var *grubii*(serotype A), *C. neoformans* var *neoformans* (serotype D), *C. neoformans*(hybrid AD) and *C. gattii* (serotypes B and C) (23). Currently, there is a reclassification proposal of *C. neoformans* and *C. gattii* into seven species, based on molecular evidences (24).

*C. neoformans* is a saprophyte, cosmopolitan fungus, globally disseminated and found in bird excrements (usually pigeons) in soil and trees. It causes cryptococcosis, predominantly in immunosuppressed individuals. *C. gattii* is found in tropical and subtropical region tree trunks, causing infection, especially in immunocompetent (25).

The balance between host immune system and fungus virulence is directly related to disease development or not. It is worth noting that infection establishment is provided by man exposure to environments contaminated by fungus, as there is similarity between clinical and environmental isolates in individual with cryptococcosis (26).

Human cryptococcosis occurs primarily through dried yeast cell inhalation, or possibly basidiospores, that are deposited in alveolar space (FIG. 1). Infectious strain virulence, inoculant size and individual immunological state are preponderant factors to disease progress (27).

The infection can be asymptomatic or have latent form, depending on the host immune system. As a contrast, in immunocompromised individuals, cryptococcal cells proliferate and disseminate to several organs, especially the brain. In these conditions, meningoencephalitis backgrounds are common (28).

It is worth noting that the interaction between *C. neoformans* and environmental predators is seen as a significant factor to fungus progress as a successful facultative intracellular pathogen. *C. neoformans* can survive in amoebas and can use the same pathogen strategy in human macrophages, which in several aspects provide a similar environment. Thus, it was proposed that such environmental niche predation has selected cryptococcal virulence characteristics that enable pathogenesis in human hosts (29).

Phagocytic cells are the first organism defense line against pathogen fungi. The interactions between *Cryptococcus* and phagocytes can result in infection control, relying on several stimulating factors. However, phagocytes can enable higher risk to disseminated fungal infection, as they can carry alive fungi among different tissues. The individual immunological state is directly linked to such interaction destination. Immunocompetent individuals in general block fungal dissemination through local cellular mechanisms. Immunocompromised patients produce an inflammatory response that enables pathogen replication (30, 31), with consequent dissemination.

Disease progress is directly related to profiles Th1 and Th2, and consequent macrophage polarization M1/M2. (32). Type Th1 cells produce large TNF and INFγ quantities, which induce type M1 macrophage activation, and consequent *Cryptococcus* elimination (33). Type Th2 cells produce cytokines involved in inflammatory reactions, inducing to type M2 macrophage proliferation, that do not have antifungal activity and enable fungus proliferation (30).

It is worth noting there are several molecules produced by *Cryptococcus* that stimulate type M2 macrophage response (34, 35). They include arginase, urease and laccase (30). Such macrophages represent cryptococcosis dissemination central role, as *Cryptococcus* can use such cells as replication niche and exit macrophages through non-lytic exocytosis, among other mechanisms (14). Due to such characteristic, an assumption that macrophages could act as Trojan Horses was proposed, leading *C. neoformans* internalized cells to cross blood-brain barrier and reach the Central Nervous System (SNC) (36).

*C. neoformans* preference for SNC is correlated to several factors. SNC can represent to fungus a safer host, as the brain is a immunologically privileged environment. What is more, L-3,4 dihydroxyphenylalanine (L-DOPA), diphenolic substrate used by fungus to melanin synthesis, can enable its permanence in SNC. *C. neoformans* and *C. gattii* melanization protects fungi against oxidative stress, phagocytosis, decreases antifungal action, and changes immunity standards (27).

IFIs clinical diagnostic is hard, due to lack of signs and specific symptoms at disease start. Lab tests are, thus, essential for a closure that enables morbidity and mortality decrease.

Optimal characteristics to develop diagnostic platforms include early pathogen detection, fine sensibility, capacity to achieve discrimination in species level, wide pathogen range detection (multiple capacity), reliability, quantitative accuracy (capacity to differentiate between disease and colonization) and not being invasive. No standard diagnostic tests comply with such criteria, and indeed, several are absent in different levels.

Fungal pathogen identification is still based on organism direct view by optical microscopy, infected tissue histopathology and fungus cultivation (17, 37). Even though classic fungal culture and traditional serology techniques are significant and necessary, fungal detection and identification by molecular techniques are required (antibodies and antigenics, PCR and sequencing), enabling quick and efficient diagnostic, complementing culture-based traditional methods.

One of IFI diagnostic culture use greatest limitations is linked to result achievement time, as several pathogens, especially filamentous fungi, have slow growth. Depending on inoculant characteristics and fungal growth, culture requires at least 2 to 3 days of incubation, and for some species, days to weeks. Non-sterile source positive cultures, including Bronchoalveolar Lavage (BAL) samples, also require cautions interpretation to differentiate between fungal colonization and actual invasive agent insulation. Finally, fungal hemocultures, although they are not invasive and highly specific, required long incubation and can be equally insensitive, presenting reliable results in 50% of the cases linked to *Candida* spp. and 10% of cases linked to *Aspergillus* spp. (38).

In case of fungal meningitis, the problem can be even more severe, as an inaccurate or late diagnostic can incur in patient death. It is worth noting that, in some cases, biopsy is required to establish an accurate diagnostic, as cerebrospinal liquid cultures are frequently not diagnosed, especially in cases with fungal cerebral abscess (39). In cryptococcosis, such problems can be easily solved by using Serum Cryptococcal Antigen (CrAg) test, which uses fungal antigenic in patient serum. This test consists of an efficient and cheap method to prevent death in people infected with HIV with lymphocyte counts T CD4≤100/μL in regions with socio-economic restrictions (40).

Biopsy is generally not a feasible option to severely ill patients and with suspicion of IFIs, including aspergillosis, as they have higher hemorrhage probability due to thrombocytopenia (39) The test presents limited sensibility and specificity (41) and requires properly trained professionals to identify the microorganism. Despite of that, microscopic observation still is the diagnostic gold standard to several IFIs (42).

Fungal antigenic identification in patient samples has progressed significantly in IFIs diagnostic area. These molecules include mostly cellular wall components (FIG. 2). Such structure detection might suggest IFI occurrence, and are often detectable before clinical signs or disease symptoms are present (43). These biomarkers include (1,3)-β-D-glucan (BDG), *Aspergillus* galactomannan (GM), *Cryptococcus* glucuronoxylomannan (GXM) and histoplasmin antigenic.

As abovementioned, antigenic detection enables identifying IFIs early, directing therapeutic strategies and assessing disease prognostic in response to therapy (38,45,46). BDG is found in most fungi, except for Zygomycetes, *Blastomyces dermatitidis, Mucoromycotina, Cryptococcus* spp. and some Basidiomycota (e.g., *Malassezia* spp.) (45).

Not only BDG has limited specificity to specific fungal pathogens and ranges according to organism, but also there are clear advantages compared to other techniques. In case of invasive candidiasis, there is sensibility in approximately 70% compared to hemoculture (47). In case of *Pneumocystis* pneumonia, greater sensibility (96%) and specificity (84%) are observed in serum compared to the same analysis in candidiasis and aspergillosis, that did not exceed 80% (48). It should be highlighted that such diagnostic kits are already available in the market and are used to assess pneumonia cases by *Pneumocystis* (Company Era Biology—Goldstream Fungus (1-3)-β-D-Glucan Test (GCT-110T—Company MiraVista Diagnostics—Beta-D Glucan Assay).

On the other hand, the high cost associated to false positive results in patients with Positive and Negative Gram bacteremia (37%) and in β-lactam antibiotic batches (33%) showed that such diagnostic test can be limited, even though it is useful in combination with other complementary diagnostic methods (49).

Galactomannan (GM) is a characteristic *Aspergillus* spp polysaccharide released during growth, being detected by commercially available tests in blood circulation, serum, urine and BAL during fungus growth in tissue (50). As it is released bu fungus constitutively, GM can be a prognostic and disease progress and/or treatment response marker. Several immunoenzymology methods are used to detect GM, however the most promising one is sandwich ELISA, as it is the most sensitive one, detecting low GM concentrations in clinical samples (51).

GM test presents a better result according to patient population, for instance in transplanted patients or with hematological diseases, presenting approximately 90% specificity whenever used through Bronchoalveolar liquid detection (43,52). In pediatric patients, the test can produce false positives in approximately 80% of the cases, a fact associated to breastfeeding, bacteremia or antibiotic use (43). What is more, GM presents crossed reactions with several fungi antigenics, as mannan polysaccharide is found is several fungi wall.

However, there are challenges associated to this methods, including false positive result risk due to crossed contamination or reactivity, as well as false negatives, due to trial imperfect sensibility. As a general rule, no lab diagnostic test shall be used as an independent test to IFI diagnostic. Current fungal diagnostic tests shall be used in combination with host assessments with host assessments and radiographic characteristics to managed in optimized way the patients at risk (43).

During the last decade, PCR trials have emerged as promising experimental approaches to detect fungal pathogens. PCR use is common at clinical practice, with great application to guide preventive or directed therapy to control pathogens (43,50,53).

In fungi, PCR gene amplification usually engages regions 18S, 5.8S and 28S, that codify to ribosomal RNA (rRNA), and DNA sequence variable areas of transcribed spacer internal intervening regions, named ITS1 and ITS2 (54).

Apart from PCR, several molecular method variety, including DNA sequencing, microarrays and mass spectrometry, laser ionization and desorption by mass spectrometry by ionization (MALDI) is used to develop wide range molecular detection trials (43). However, the most usual approach to molecular detection is PCR, followed by Sanger sequencing, as it is can be particularly useful when fungal culture is negative or not requested at the time tissue biopsy has been performed (55).

Over the last 30 years, fungi relevance as disease causer in humans has increased dramatically (18). On the other hand, therapeutical options available are not accessible, toxic or inefficient, thus the search for new antifungal relevance becomes unquestionable (56).

As abovementioned, there are currently four main classes of antifungal drugs. These classes include azoles, polyenes, pyrimidines and echinocandins. Several other classes, including morpholines and allylamines, are used only as topical agents, due to lower efficacy or severe adverse effects, whenever administered systematically.

Azoles are the most widely used antifungal in clinical practice. These drugs present ergosterol biosynthetic rout as target, acting mainly through key enzyme inhibition, lanosterol 14 alpha demethylase, coded by gene ERG11 (57).

FLC and itraconazole, broad spectrum azoles, since the 1990s have been used in different systemic infection treatment, due to their high absorption power and lower toxicity than initially developed azoles (58). However, they present drug interactions with drugs used in chemotherapy or AIDS treatment (58,59). Moreover, itraconazole and FLC are inefficient against some emerging pathogens, including *Scedosporium, Fusarium* and *Mucorales* (60). The perception that azole fungal strength phenomenon perception is increasing is still high (58). Other drugs of this class are under development, including new generation triazoles. Some have been approved by Food and Drug Administration (FDA) (57).

Polyene class includes more than 200 molecules, most of them are produced by *Streptomyces* bacteria, however, only three have clinical application, as follows: AmB, nystatin and natamycin (58). These compounds complex with ergosterol in plasmatic membrane (57). Its amphiphilic structure enables insertion in lipid bilayer, followed by pore development. Pore development enables plasmatic membrane destabilization with consequent intracellular component leakage, resulting in cellular lysis (61). Polyenes bond with lower affinity to cholesterol, ergosterol human analogous. The cholesterol bond explains its high toxicity and consequent side effects (62). Thus, AmB is widely used in systemic infections, unlike nystatin and natamycin that, as they are extremely toxic, are only used topically in vaginal tract and cutaneous infections (63).

AmB has poor absorption through gastrointestinal tract, incurring in the need to administer through intravenous route associated to severe adverse effects, especially in kidneys and liver (64). It is worth noting that side effects including nausea, vomit and fever are common, but the most severe effect is nephrotoxicity (65). New AmB formulations, including AmB liposomal complexes, minimize such side effects, however they raise the drug cost (66,67).

Fluoropyrimidines are cytokine structural synthetic analogous, and as a consequence, they inhibit nucleic acid synthesis (68). Nevertheless, such drugs cannot be used in isolated way, due to strength mechanism report (69). Current gold standard to meningoencephalitis by *Cryptococcus* is AmB combination with 5-flucytosine (5-FC), as it minimizes AmB nephrotoxicity due to drug lower dose administration for a lower time period, and it reduces strength to 5-FC (64). It should be highlighted that 5-FC is not available in Brazil, limiting Brazilian patient access to optimal treatment.

Echinocandins are non-competitive inhibitors of β (1-3)-glucan synthase, an enzyme that catalyzes polymerization of uridine diphosphate-glucose in β (1-3) glucan, one of structural components responsible for cellular wall integrity maintenance in fungi (70). β (1-3)-glucan synthase inhibition leads to cellular wall destabilization and intracellular component overflow, resulting in cellular lysis (71,72). However, several fungal pathogens are partially or totally resistant to echinocandin action, including *C. neoformans* and *C. gattii* or species belonging to *Trichophyton* and *Fusarium* genders, apart from *Scedosporium apiospermum, S. prolificans* and *Cladophialophora bantiana* (58). However, echinocandins are a fine alternative to fight other fungal infections. Most treatments with failure in classic therapy with azoles or polyenes is used successfully with echinocandins.

Antifungal strength mechanisms can start drug efficient concentration decrease, drug target alterations or superexpression and metabolic deviations (57).

Antibodies or immunoglobulins (Ig) are glycoproteins secreted by cells B that present the capacity to identify and/or neutralize foreign organisms or antigenics to host immune system (73). Ig are formed by two heavy protein chains, and two light ones, which have variable regions that participate of antigenic acknowledgment and regions included that perform molecule effecting function (73).

Antibody diversity is performed by amino acid sequence variability of light and heavy chain variable region. Complementarity determinant regions (CDR) are hypervariable sequences that contact directly the antigenic to be acknowledged (73).

Antibodies can be divided in different classes and subclasses, named isotypes (73). Ig classes include IgM, IgG, IgA, IgD and IgE, with human subdivision of IgA and IgG isotypes in IgA1, IgA2, IgG1, IgG2, IgG3 and IgG4, each one performing different effecting functions (73).

Monoclonal antibodies (AcM) were developed for the first time in 1975 by Georges Köhler and César Milstein (74) through hybrid cell production, named hybridoma, resulting from two different cell fusion (74). Hybridoma incurs from lymphocyte B fusion (previously immunized with antigenic of interest) with myeloma cells, generating an immortal cell and AcM producer (FIG. 4).

AcM present different applications in diagnostic and therapy fields, and can be used not only to infectious diseases caused by bacterias, viruses and protozoa, but also to autoimmune diseases and tumors, considering their high sensibility and specificity (75). In the last 30 years, around 80 AcM were approved by FDA to treat several diseases, including cancer, chronic inflammatory diseases, neurodegenerative diseases and infectious diseases (76).

Infectious disease immunodiagnostic has improved significantly upon hybridoma technology advent, as AcMs overcome polyclonal antibody limitations, and AcMs are capable of providing identification of only one antigenic, generating reproducible and consistent results (77).

AcM usage against pathogen fungi has become increasingly frequent. Antibodies with therapeutical potential have been developed with antigenic as histone 2B of *H. capsulatum* (78), β-glucans of *C. albicans* (79), glucosylceramide of *C. neoformans* (80), melanin of several pathogens (81), and thermal shock proteins of *H. capsulatum* (82). Antibodies with diagnostic use include reactive ones against antigen M and H of *H. capsulatum* and against antigen of *Cryptococus* (CrAg) (83,84).

AcM administration in IFI relies on several factors, that include necessarily AcM isotype, its titration, presentation via histocompatibility main complex (MHC), and especially immune cell activation (85).

AcMs against fungi can mediate three different effects: protection (inhibiting growth, immunomodulating immune system response and neutralizing fungus effects in host tissue), disease increase (as it enables disease dissemination, for instance, enabling *C. neoformans* phagocytosis) and virulence neutralization (through release inhibition of proteins or fungal polysaccharides) (77). These effects are illustrated in FIG. 5.

AcMs can also act indirectly in protection against IFI, through phagocytosis, complement system activation, cellular cytotoxicity regulation, and phagosome maturation (86). They can also impact directly, as in biofilm development (87), polysaccharide release (88), dimorphism (89), gene expression (90) and signal transduction (86).

Immunotherapeutical studies characterized protective AcM against different targets and different fungal species, including: β-1,3 Glucan—*A. fumigatus* (91), Als3—*C. albicans* (92), heat-shock protein 60—*H. capsulatum* (93), GXM—*C. neoformans* (94), gp43—*P. brasiliensis* (95) e p55—*Pneumocystis* spp (96). These studies evidenced that some fungal antigenics induce the protection mediated by antibodies during fungal infections.

Some of these antigenic targets to be maintained are applied to different fungi. Due to that, chitin, N-acetylglycosamine polymer, as it is one of the main fungal cellular wall parts, becomes and outstanding target to new therapeutical strategies.

Therefore, fungal infections have become one of the main disease causes in immunocompromised individuals, being a severe and underestimated public health issue (16), as well as drug resistance phenomenon might lead to significant increase immunocompromised individual morbidity and mortality around the world.

Thus, searching for alternatives that decrease antifungal treatment adverse effects, monoclonal antibody use in fungal infection templates is considered highly promising, as it can bond with high specificity to antigens expressed in fungi in patient body fluids, and it is also key tools in clinical diagnostic field.

Moreover, efficient diagnostic techniques can enable identifying patients with IFIs earlier than only with cellular culture. However, there are challenges associated to this methods, including false positive result risk due to crossed contamination or reactivity, as well as false negatives, due to trial imperfect sensibility. It is desired, thus, combination with different tests in association with host assessments, including intrinsic characteristics of patients at risk.

Concerning this background and due to fungal cellular surface architecture major complexity, chitooligomers were chosen as target to develop AcM.

Thus, present invention discloses AcM against chitin oligomers for therapeutical use and fungus diagnostic in biological samples. What is more, present invention also reveals synergism of AcM developed with AmB, due to bonding with chitooligomers in infection murine template by *Cryptococcus neoformans*, led to infected individual survival.

Invention advantages shall be evident in invention description provided in this document.

SUMMARY OF THE INVENTION

Present invention purpose is providing monoclonal antibodies (AcMs) to treat fungal infections and fungal infection diagnostic.

Particularly, AcMs are developed to present activity against fungal chitooligomers.

At a first aspect, present invention provides monoclonal antibody, including:
(i) VH CDR1 sequence, as described in SEQ ID NO: 1, VH CDR2, as described in SEQ ID NO: 2 and VH CDR3, as described in SEQ ID NO: 3; and (i) VL CDR1 sequence, as described in SEQ ID NO: 4, VL CDR2, as described in SEQ ID NO: 5 and VH CDR3, as described in SEQ ID NO: 6; or
(i) VH CDR1 sequence, as described in SEQ ID NO: 7, VH CDR2, as described in SEQ ID NO: 8 and VH CDR3, as described in SEQ ID NO: 9; and (i) VL CDR1 sequence, as described in SEQ ID NO: 10, VL CDR2, as described in SEQ ID NO: 11 and VH CDR3, as described in SEQ ID NO: 12.

As a second aspect, present invention foresees a pharmaceutical composition, which includes monoclonal antibody abovementioned. Pharmaceutical composition can also include AmB and/or FLC, as well as pharmaceutically acceptable vehicle/excipient. Pharmaceutical composition is for use in fungal infection treatment.

As a third aspect, present invention foresees the use of monoclonal antibody to prepare a drug to treat fungal infections. The use abovementioned can be performed in combination with polyenes and/or azoles preferably, AmB and/or FLC.

As a fourth aspect, present invention foresees a fungal infection diagnostic method that includes:
(i) providing monoclonal antibody or composition abovementioned with a sample achieved from an individual.
(ii) contacting monoclonal antibody or composition abovementioned with biological sample to be tested for enough time and under enough conditions to develop antigenic/antibody complex development; and
(iii) detecting antigenic/antibody complex developed in previous stage through a detection technique capable of generating detectable signal at present of antigenic/antibody complex abovementioned. Biological sample is selected from the group, including saliva, urine, serum, blood, Bronchoalveolar Lavage, peritoneal fluid or liquid, or any other biological fluids of the individual.

As a fifth aspect, present invention foresees a fungal infection diagnostic kit that includes monoclonal antibody or composition abovementioned. The kit can also include use instructions. What is more, the kit can also include antigenics/antibody complex detection media, which can include a signal generator, capable of generating a detectable signal.

As a sixth aspect, present invention foresees a fungal infection treatment kit, characterized by the fact it includes
(i) monoclonal antibody or composition abovementioned; and
(ii) antifungal agent,
(iii) Instructions to use components in combination.

As a seventh aspect, present invention foresees a fungal infection treatment method including administration of a therapeutically efficient quantity of antibody of composition abovementioned in an individual.

As an eighth aspect, present invention foresees an antibody or pharmaceutical composition to be used in fungal infection treatment in an individual.

11

12

Figure 1:
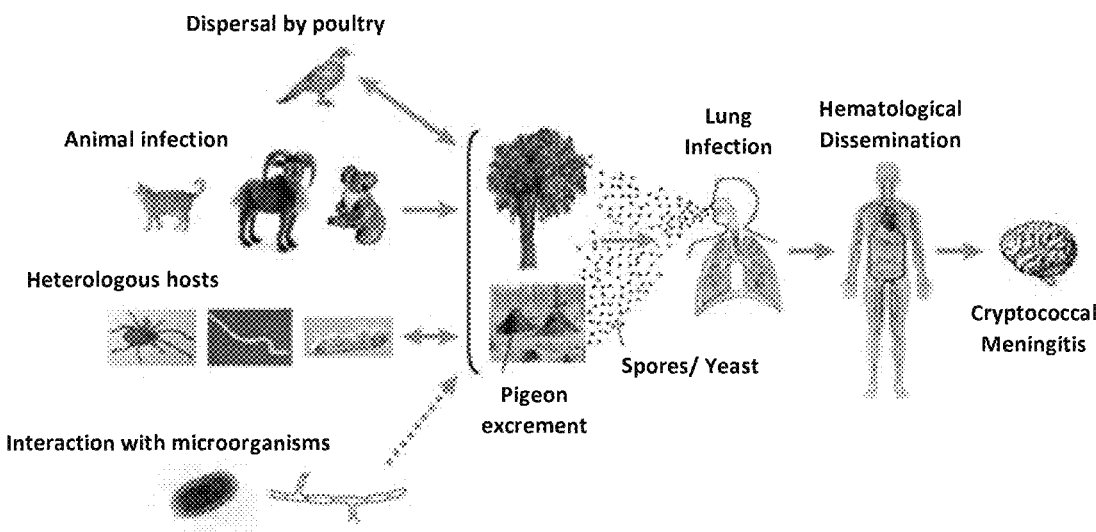
FIG. 1 refers to *Cryptococcus* spp infection cycle. Fungus can survive in soils and trees, and infect several animals, including pigeons, that are fungal cell dispersion media. In humans, through spore or dried yeast inhalation present in the environment, a lung infection is established, which can evolve to diseases in central nervous system (SNC). (Amended of [28]).
Figure 2:
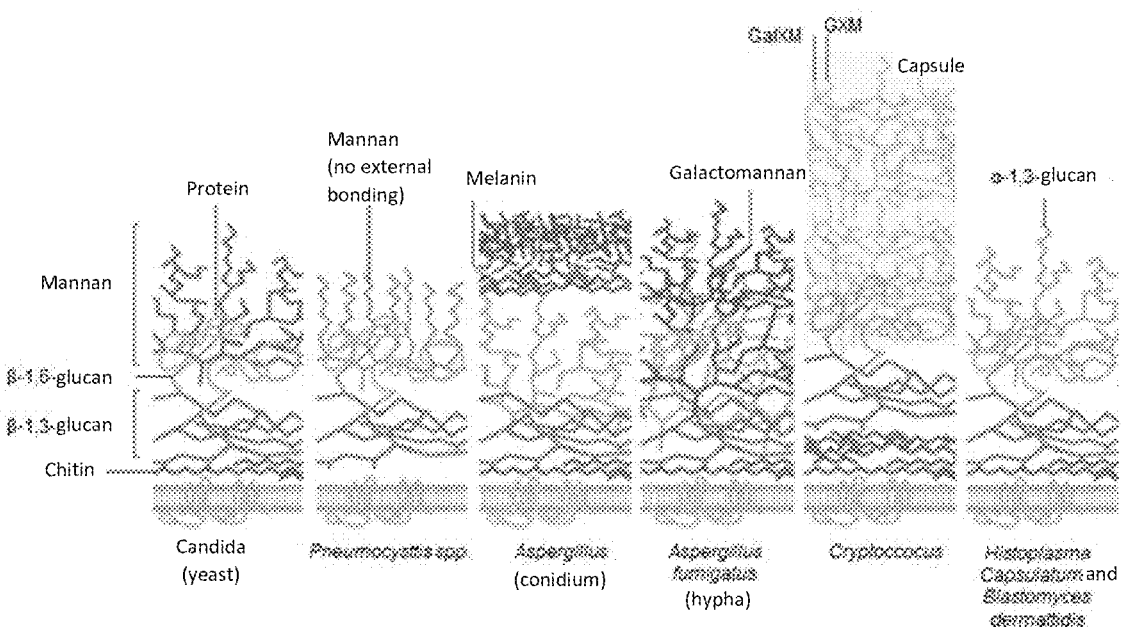
FIG. 2 refers to schematic representation of cellular wall structure and fungus capsule (Amended [99]).
Figures 3, 4:
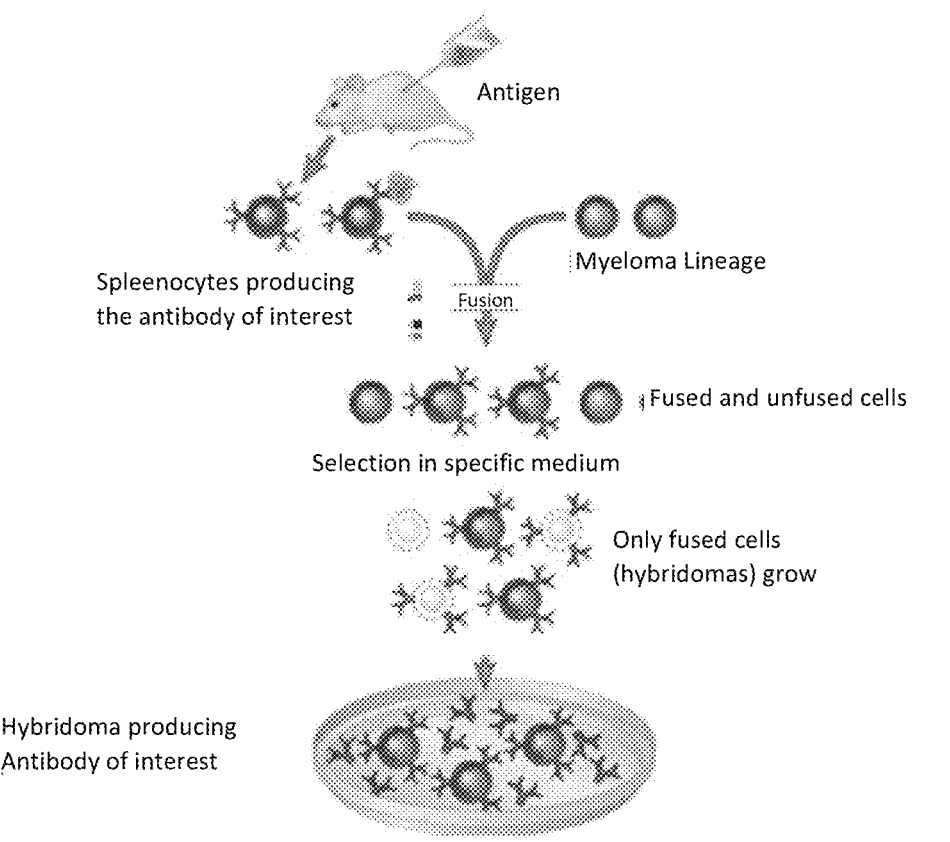
FIG. 3 refers to action of four main antifungal drug classes. The illustration evidences action of four main antifungal drug classes. Flucytosine evidences its action in nucleic acid synthesis, and other classes action site is in plasmatic membrane or cellular wall, whether in synthesis or complexing to ergosterol (Azoles and AmB, respectively) or in β-Glucan Synthase (Echinocandin). (Amended of [100]).

FIG. 4 refers to AcM development through hybridoma technique. Lymphocytes B fused with murine myeloma cells generate hybridomas, that are immortal antibody producing cells, that are later selected by immunoassay techniques to choose the best AcM producing clone being studied. Figure adapted from Abbas, A. et al. 2015 [073].

Figure 5:
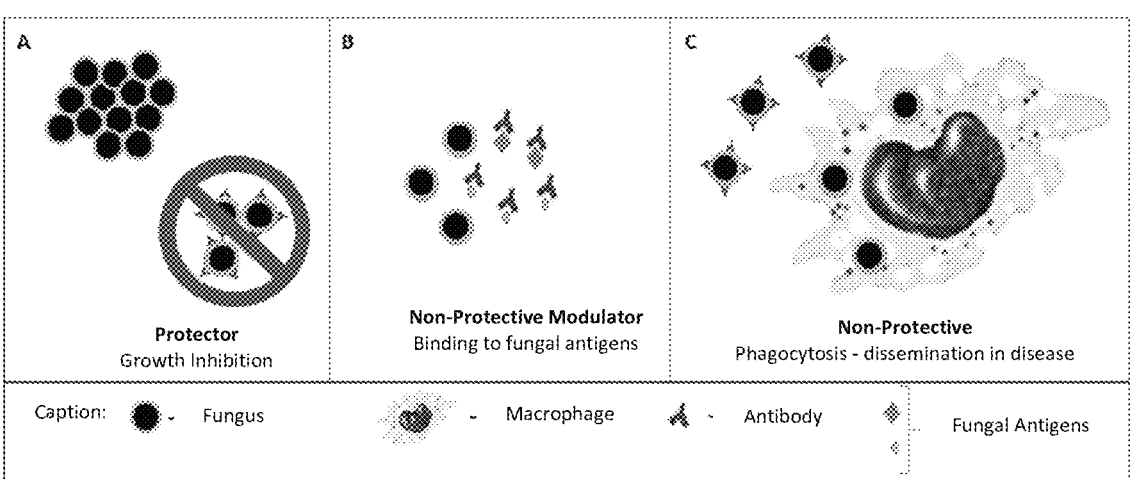

FIG. 5 refers to proposed mechanisms of antibody action against fungi, which can be considered in three general categories, including: A) growth direct inhibition, B) host tissue fungal product unwanted effect neutralization, and C) innate immune mechanism immunomodulation and potentiation, which in case of *C. neoformans* are not protective.

Figure 6:
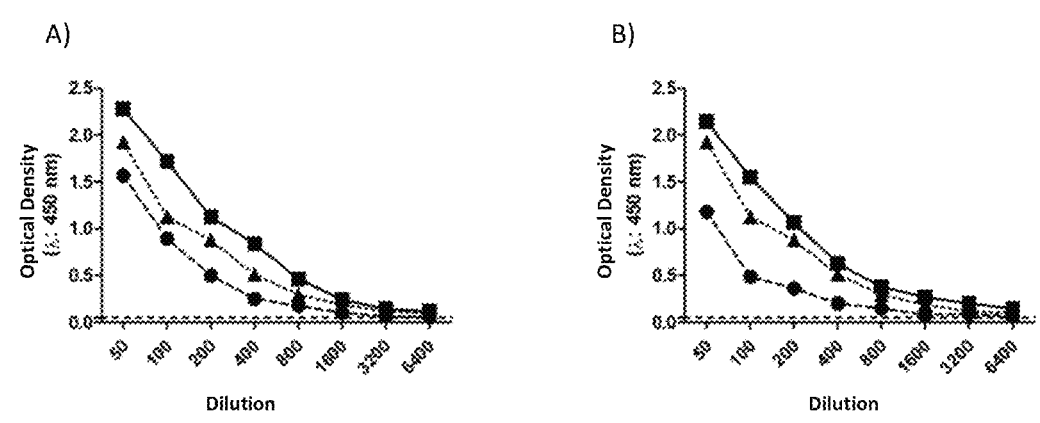

FIG. 6 refers to mice serum antibody titration curve achieved by ELISA. Balb/C mice were immunized with *C. gattii* via i.p. and chitotriose via i.p. and i.v. Immunized animal antibody serum titration was dosed by the end of the immunizations. (A) Serum titration to Immunoglobulin M (IgM); (B) Serum Titration to IgG. Curves with square, triangle and circle represent different animals. Broken line represents pre-immune serum cut line.

Figure 7:
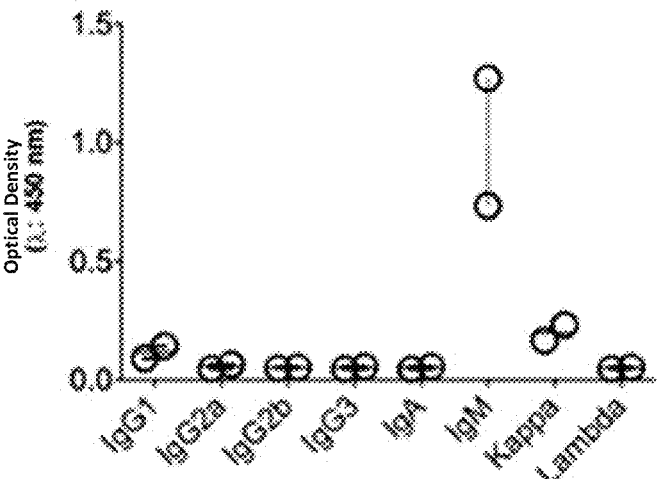

FIG. 7 refers to selected AcMs isotyping. The trial was performed using ELISA indirect kit that defines different immunoglobulin isotype presence (Igs). Selected AcMs refer to AF1/CC5 and HC6/DD11 antibody isotyping, which evidenced IgM detection prevalence.

Figure 8:
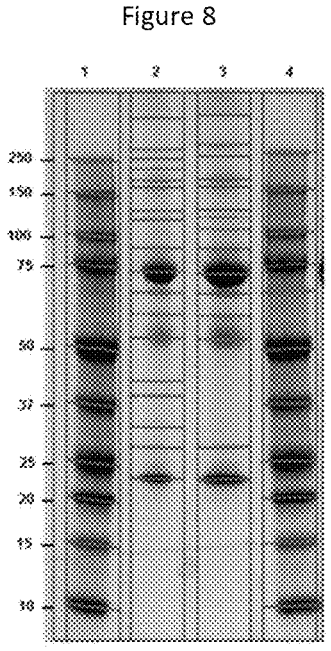

FIG. 8 refers to AcM AF1/CC5 and HC6/DD11 purification analysis. Lane 1: Precision Dual Color (Bio-Rad) molecular weight standards; Lanes 2 and 3: AcM AF1/CC5 and HC6/DD11, respectively; Lane 4: Precision Dual Color (Bio-Rad) molecular weight standards. Predominant bands in fractions 2 and 3 correspond to heavy (~70 kDa) and light chains (molecular mass ranging between ~23-24 kDa) of IgM.

Figure 9:
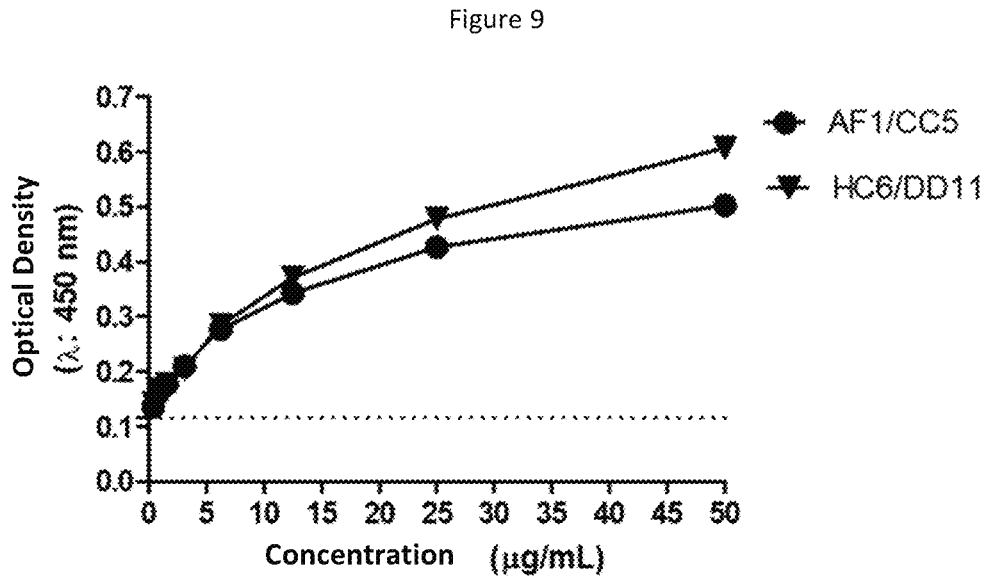

FIG. 9 refers to AcM to *C. albicans* bond saturation curve.

FIG. 10 refers to ELISA saturation curve to *C. neoformans* and *C. albicans* detectable by AcM HC6/DD11 and AF1/CC5. In (A) related to antibody AF1/CC5 and (B) related to antibody HC6/DD11.

FIG. 11 refers to Dot Blot saturation curve to *C. neoformans* and *C. albicans* detectable by AcM HC6/DD11 and AF1/CC5. In (A) related to antibody AF1/CC5 and (B) related to antibody HC6/DD11.

FIG. 12 refers to IF analysis of AcM HC6/DD11 and AF1/CC5 with *C. albicans* reaction. Left panels show fungal cells through differential contrast, and other panels show cells in fluorescence mode. Arrows indicate characteristic polar label of this fungal target type, which were evidenced to both AcM, and it is identified also in overlapping image (Calcofluor/Alexa 548).

Figure 13:
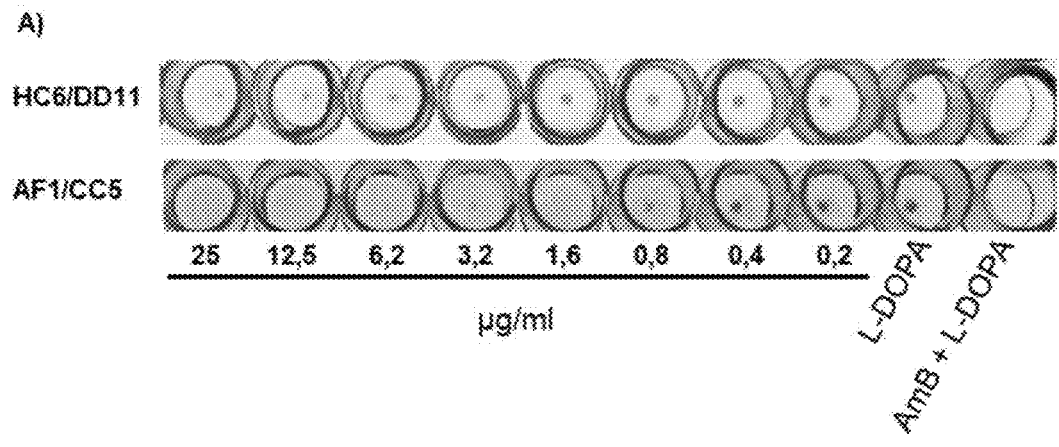
Figure 13:
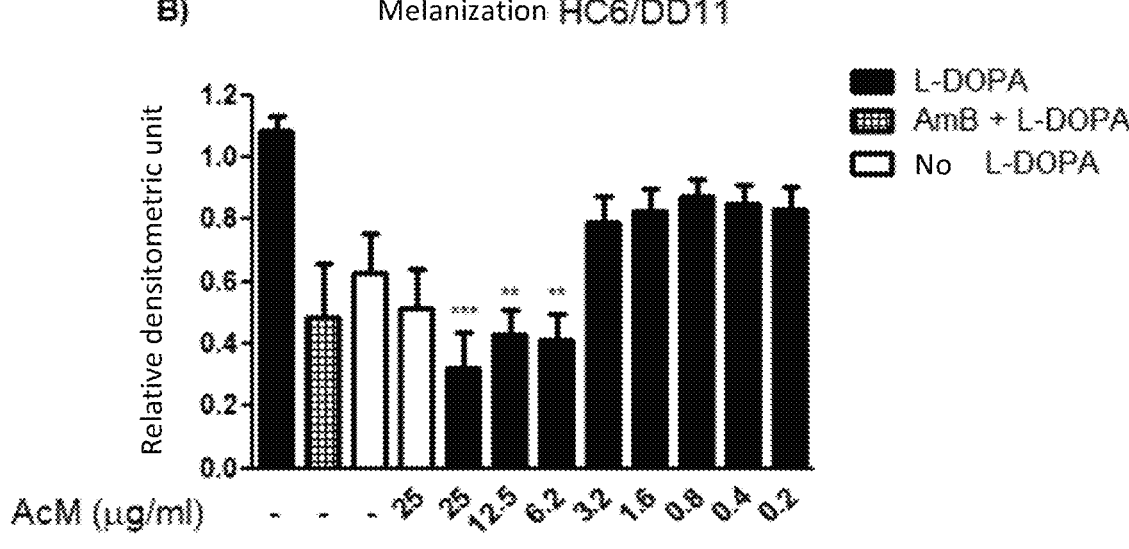
Figure 13:
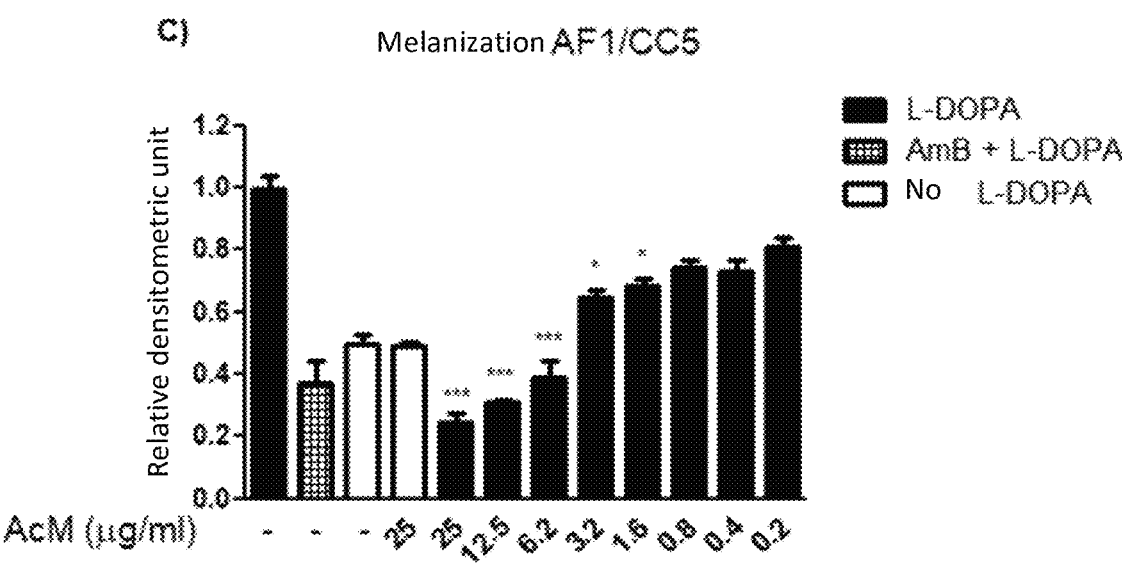

FIG. 13 refers melanization trial. (A) Pigmentation visual analysis upon fungus growth in liquid media supplemented with L-DOPA and treated with AcM; B and C) Graphic representation by pigmentation relative densitometry. AcM HC6/DD11 present partial pigmentation inhibition until 6.2 µg/ml (p<0.05) concentration, and AcM AF1/CC5 presented total inhibition until 6.2 µg/ml (p<0.001) concentration and partial one in 3.2 and 1.6 µg/ml (p<0.05) concentrations.

Figure 14:
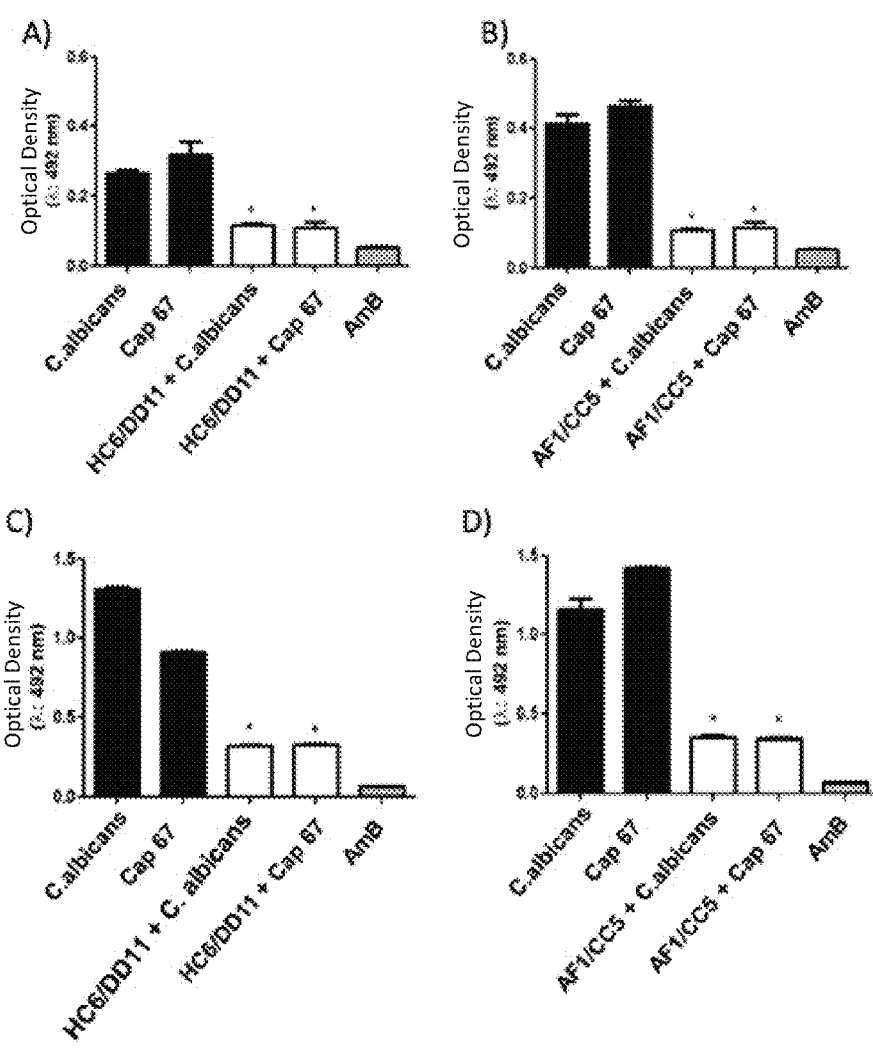

FIG. 14 refers to XTT trial—Biofilm development. Biofilm development was measured indirectly by XTT reduction trial. Fungal treatment with AcM HC6/DD11 and AF1/CC5 reduced biofilm development significantly compared to fungus without treatment (p<0.05). Black bar fungi without treatment and white bar fungus treated. Washed cells A and B; Non-washed cells C and D.

Figure 15:
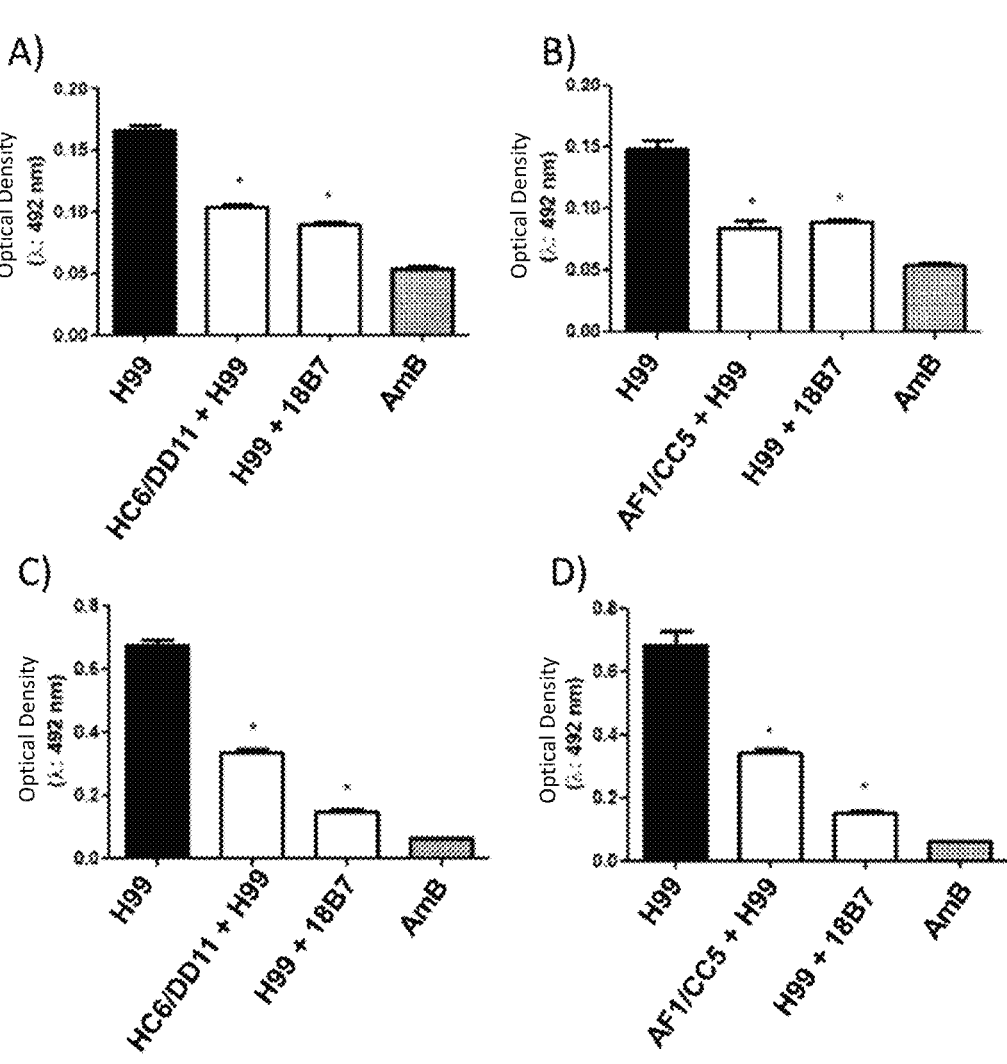

FIG. 15 refers to XTT trial—Biofilm development. Biofilm development was measured indirectly by XTT reduction trial. Fungus H99 treatment with AcM HC6/DD11 and AF1/CC5 reduced biofilm development significantly compared to fungus without treatment and presented similar behavior to fungus treated with antibody 18B7 (p<0.05). Black bar fungi without treatment and white bar fungus treated. Washed cells A and B; Non-washed cells C and D.

Figure 16:
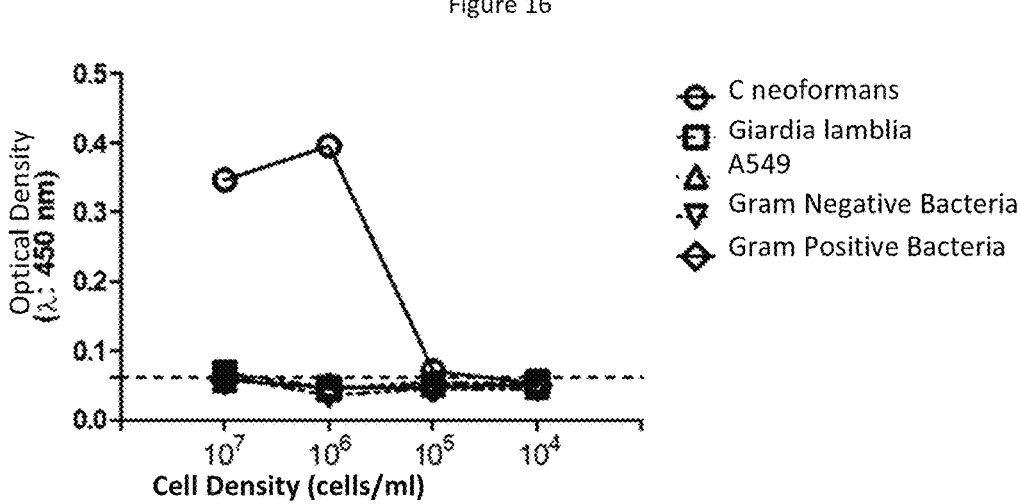

FIG. 16 refers to ELISA against intact cells *of C. neoformans, Giardia lamblia*, line A549, *E. coli* and *Staphylococcus aureus*. Broken line represents reaction blank.

Figure 17:
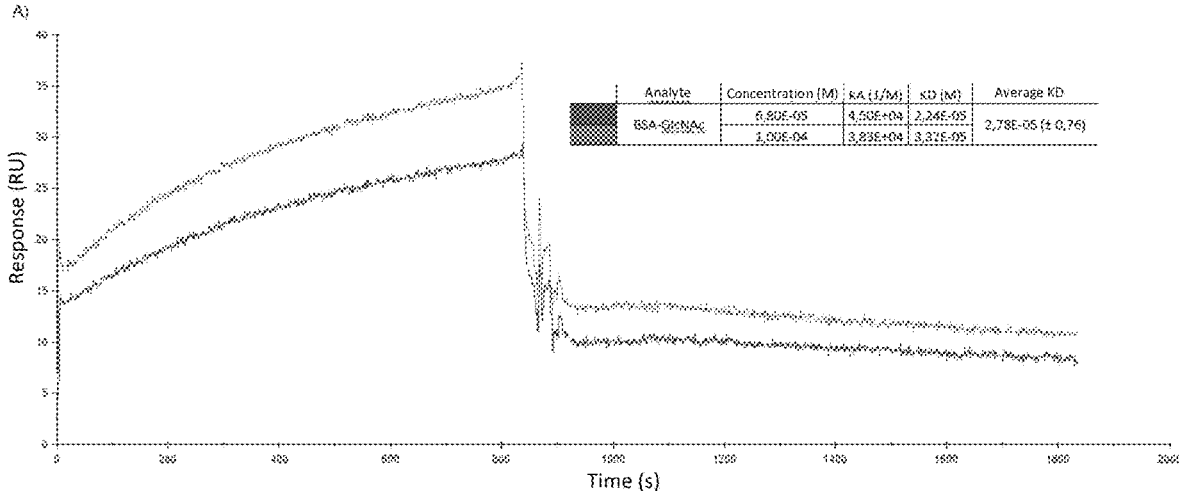

FIG. 17 refers to representative sensorgram, evidencing both AcM interactions against chitotriose. (A) AcM HC6/DD11 and (B) AF1/CC5. 0.06M chitotriose concentration is highlighted in green, and 0.1M one, in red.

Figure 18:
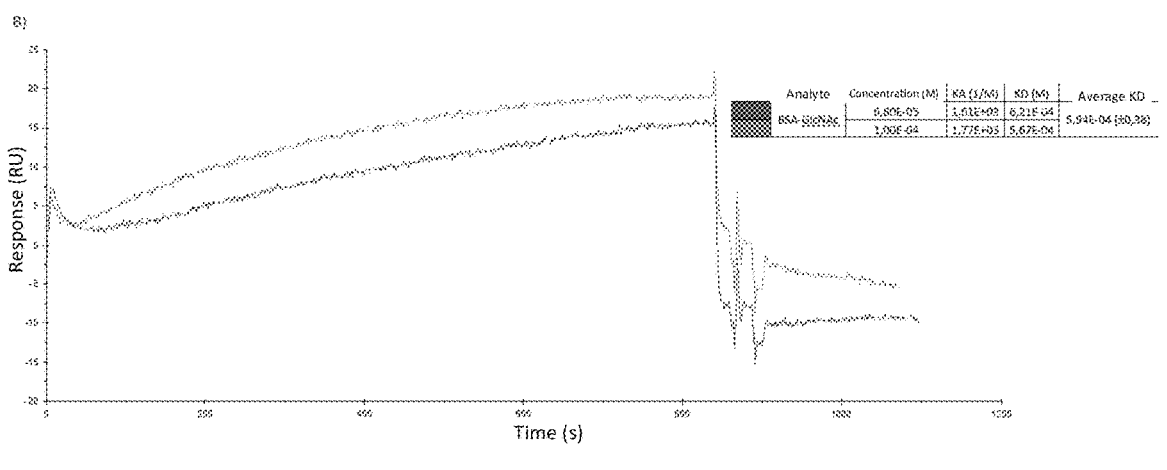

FIG. 18 refers to (A and B) fungicide synergic effect representation of AcM HC6/DD11 and AF1/CC5 added to AmB 0.1 µg/ml from 6.2 µg/ml added to 0.1 µg/ml of AmB compared to AmB in isolated form at 1 g/ml (p<0.001) concentration. A) AcM potentialized partial synergic effect at 1.6 and 3.2 µg/ml concentrations, compared to AmB isolated at 0.1 µg/ml (p<0.01) concentration; B) AcM potentialized partial synergic effect at 3.2 µg/ml concentration, compared to AmB isolated at 0.1 µg/ml (p<0.01) concentration.

Figure 19:
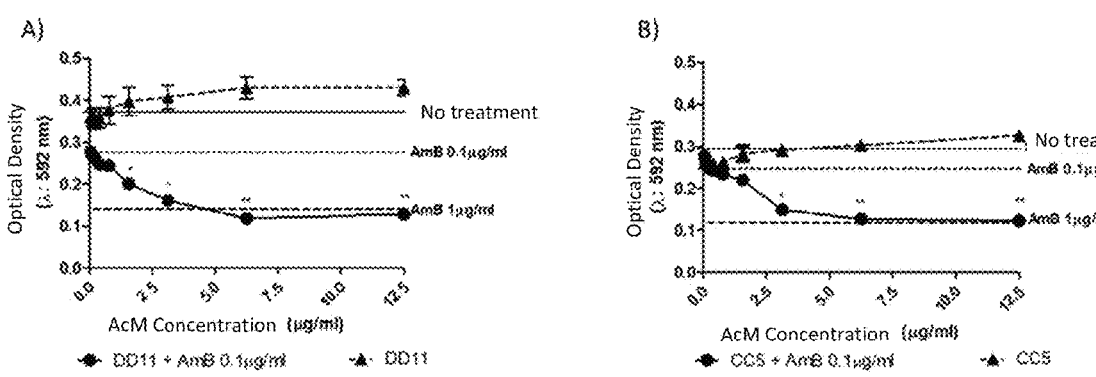

FIG. 19 refers to (A and B) synergic effect representation of AcM HC6/DD11 and AF1/CC5 added to FLC. Partial potentialized fungicide synergic effect of HC6/DD11 and AF1/CC5 from 3.2 µg/ml concentration added to 4 µg/ml of FLC, compared to FLC in isolated form at 4 µg/ml (p<0.01) concentration. Both AcM presented partial fungicide effect potentialization, whenever added to FLC at 2 µg/ml, and the behavior is similar to FLC at 4 µg/ml concentration at isolated form.

Figure 20:
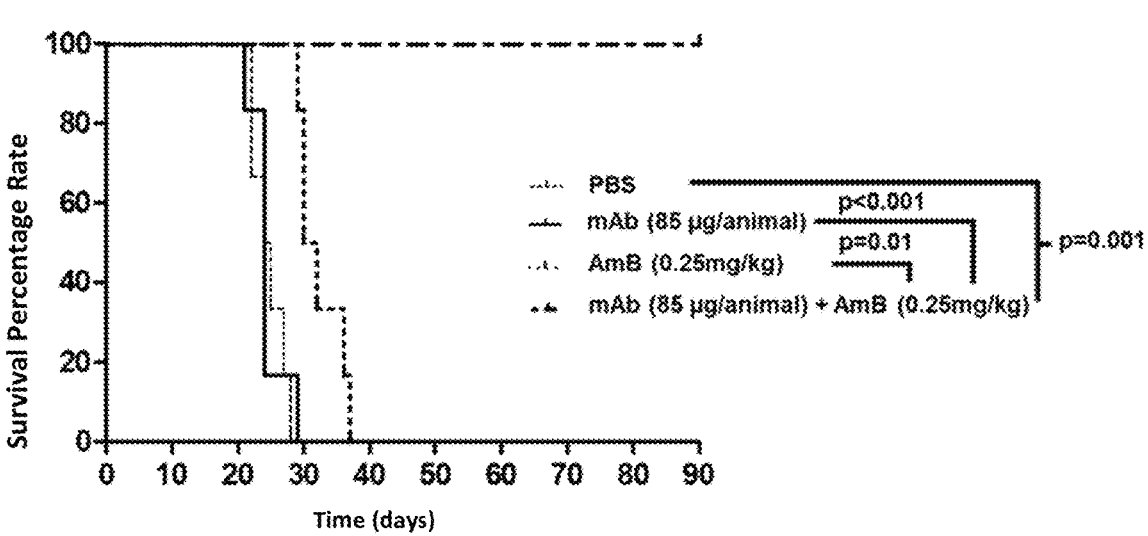

FIG. 20 refers to AcM administration added to AmB, protective in infection template by *C. neoformans*. Survival curve comparing animals treated with PBS, AcM, AmB (0.25 mg/kg) and synergic group. Groups with isolated treatment died between 28 and 37 days, and the synergic group presented 100% of survival and had statistical relevance compared to other groups (p≤0.01) (n=7).

Figure 21:
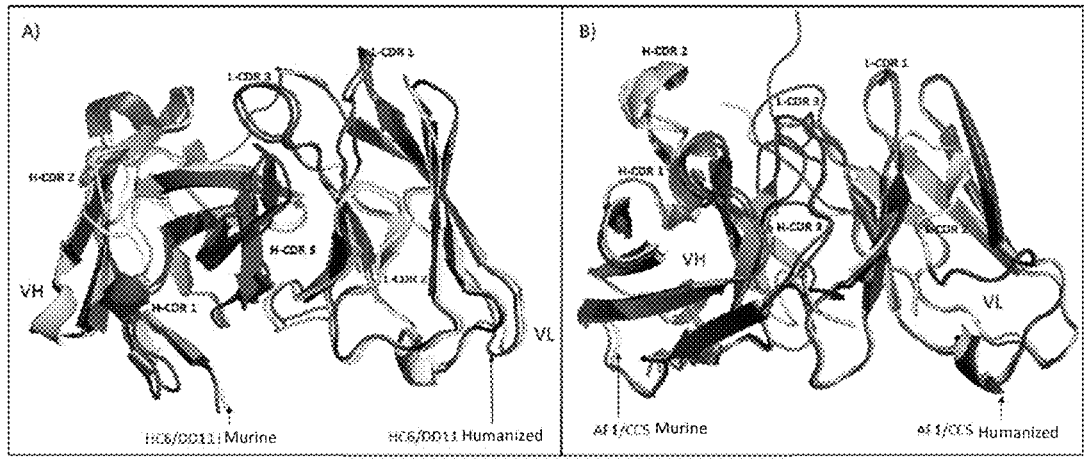

FIG. 21 refer to scFv fragment of murine and humanized antibodies.

DESCRIPTION OF SPECIFIC EMBODIMENTS OF THE INVENTION

Unless otherwise stated, every technical and scientific term used herein has the same meaning understood by a technical expert at the topic related to the invention. Terminology used in invention description purpose is describing only specific achievements, and does not have the intention of limiting the thought scope. Unless otherwise stated, every number expressing quantities, percentage rates and ratios, and other numeric values used in descriptive report and claims, shall be understood as being modified, in every case, by the term "approximately". Thus, unless otherwise stated, numeric parameters provided in descriptive report and claims are approximations that can vary, depending on properties to be achieved.

Present invention practice shall use, unless otherwise stated, standard chemistry, biochemistry, recombinant DNA techniques and immunology methods, within the technique knowledge. Such techniques are explained completely in literature. See, for instance, Fundamental Virology, 2nd Edition, vols. I & II (B. N. Fields & D. M. Knipe, eds.); Handbook of Experimental Immunology, Vols. I-IV (D. M. Weir & C. C. Blackwell eds., Blackwell Scientific Publications); T. E. Creighton, Proteins: Structures & Molecular Properties (W. H. Freeman & Company, 1993); A. L.

Lehninger, Biochemistry (Worth Publishers, Inc., current edition); Sambrook, & cols., Molecular Cloning: A Laboratory Manual (2nd Edition, 1989); Methods In Enzymology (S. Colowick & N. Kaplan eds., Academic Press, Inc.).

As used within present application, the term 'amino acid' denotes α-amino acids group that directly or in form of a precursor, can be codified by a nucleic acid. Individual amino acids are codified by nucleic acids, comprised by three nucleotides, known as codons. Each amino acid is codified by at least one codon. The fact the same amino acid is codified by different codons is known as 'genetic code degeneration'. The term 'amino acid', as used in present application, denotes α-amino acids that occur naturally, including alanine, arginine, asparagine, aspartic acid, cysteine, glutamine, glutamic acid, glycine, histidine, isoleucine, leucine, lysine, methionine, phenylalanin, proline, serine, threonine, tryptophan, tyrosine and valine.

The terms 'peptide', 'polypeptide' or 'protein' can be used interchangeably, and make reference to an amino acid polymer connected by peptide bonds, regardless of amino acid waste number that comprise this chain. Polypeptides, as used herein, include their 'variants' or 'derivatives', that refer to a polypeptide that includes variations or modifications, for instance, chemical replacement, deletion, addition or modifications in its amino acid sequence in relation to reference polypeptide. Chemical modification examples include glycosylation, PEGlaton, PEG alkylation, alkylation, phosphorylation, acetylation, amidation, etc. Polypeptide can be produced artificially from nucleotide sequences cloned through DNA technique of recombinant DNA or can be prepared through known chemical synthesis reaction.

More specifically, the term polypeptide of present invention can also be understood as antigenic, polyantigenic or multi-epitope antigenic, comprised by different epitope junction that can or cannot be interlinked by flexible or rigid linkers, specific to a single pathogen or different pathogens.

At a first achievement, present invention provides murine AcMs against chitin or chitooligomers produced through hybridoma technology.

The term 'antibody' is any immunoglobulin, including antibodies and fragments, linked to a specific epitope. The term includes polyclonal, monoclonal and chimeric antibodies, and the latter are described with further details in U.S. Pat. Nos. 4,816,397 and 4,816,567. The term 'antibody(ies)' includes wild type immunoglobulin (Ig) molecule, usually including four total length polypeptide chains, two heavy chains (H) and two light chains (L), or equivalent homologous Ig (e.g., one camelid nanobody, that includes only one heavy chain); including functional mutants, variants or derivatives of total length, that keep essential epitope bonding characteristics of one Ig molecule, and including specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Within the meaning of the term 'antibody', any 'antibody fragment' is included.

The term 'monoclonal antibody' is widely acknowledged in technical field, and refers to an antibody that is produced in mass in lab from a single clone and that acknowledges only one antigenic. Monoclonal antibodies are typically prepared by fusing an antibody producing cell B with a fast growing cell, including a tumor cell (also known as 'immortal' cell). Resulting hybrid cell, or hybridoma, is a clone capable of producing antibody indefinitely, in normal cultivation conditions.

The term 'hybridoma' is also traditionally acknowledge in technical field and is understood by any topic technical expert with general knowledge, as referring to a cell produced by fusing an antibody producing cell and an immortal cell, for instance, a myeloma cell. This hybrid cell is capable of providing antibody continuously.

The term 'antigenic' refers to an entity or fragment that can induce an immune response in an organism, particularly an animal, more specifically a mammal, including a human. The term includes immunogen and regions responsible for antigenicity or antigenic determinants.

Fungal antigenics used in present invention can be selected as from fungal cellular wall components and oligomers. More specifically, antigens can be selected from chitobiose, chitotriose, chitotetraose, chitopentaose, chitohexaose and chitoheptaose, and any other fungal antigen which origin is chitin and oligomers, and are capable of inducing an immune response. Preferably, fungal antigenic is chitotriose.

Present invention fungal antigenics can be achieved from any Fungi. kingdom species, more specifically any species of Ascomycota, Basidiomycota, Zygomycota and Chitridiomycota phyla. Even more specifically, of *Aspergillus, Candida, Cryptococcus* and *Pneumocystis* genders. Thus, species can be selected from the group comprising *Cryptococcus neoformans, Cryptococcus gattii, Candida* sp., *Aspergillus* sp., *Histoplasma capsulatum* and *Coccidioides immitis*.

Moreover, antigenics can be combined with adjuvants capable of inducing an immune response.

Adjuvants are compounds that, whenever administered jointly with an antigenic, increase immune response to antigenic, however, whenever administered individually, do not generate an immune response to antigenics. Adjuvants can increase immune response by several mechanisms, including lymphocyte recruiting, cells B and/or T stimulation and macrophage stimulation.

Adequate adjuvants to present invention can be selected, but not limited to, the following compound classes: (i) aluminum salts (alum), including aluminum hydroxide, aluminum phosphate, aluminum sulphate. Such adjuvants can be used with or without other specific immunostimulant agents, including MPL or 3-DMP, QS21, polymer or monomer amino acids, including polyglutamic acid or polylysine; (ii) oil emulsion formulations in water, including (a) MF59 (WO 90/14837), containing 5% of squalene, 0.5% of Tween 80 and 0.5% of Span 85 (optionally containing several quantities of MTP-PE) formulated in submicron particles using a microfluidizer, like microfluidizer Model 110Y (Microfluidics, Newton Mass.), (B) SAF, containing 10% of squalene, 0.4% of polymer L121 blocked by Tween 80.5% pluronic and thr-MDP, microfluidized in a submicron emulsion or stirred in vortex to generate a larger size particle emulsion, and (c) Ribi™ (RAS) adjuvant system, (Ribi Immunochem, Hamilton, Mont.) containing squalene at 2%, Tween 80 at 0.2% and one or more components of bacterial cellular wall of the group comprised by mono phosphoryl lipid A (MPL), trehalose dimicolate (TDM) and cellular wall skeleton (CWS), preferably MPL+CWS (Detox™); (iii) saponin adjuvants, including Stimulons (QS21, Aquila, Worcester, Mass.) or particles generated from them, including ISCOMs (immunostimulant complexes) and ISCOMATRIX; (iv) Freund Complete Adjuvant (CFA) and Freund Incomplete Adjuvant (IFA); (v) cytokines, including interleucines, for example, IL-1, IL-2 and IL-12, macrophage colony stimulating factor (M-CSF), tumor necrosis factor (TNF) and/or chemokines, including CXCL10 and CCL5. Preferably, adjuvant used is aluminum hydroxide (Al(OH)$_3$).

Originally developed by Köhler & Milstein [075], in hybridoma, mouse or another adequate host animal, is immunized to generate lymphocytes, that produce or are capable of producing antibodies that bond specifically to the protein used to immunization.

Upon immunization, antibody producing cells (spleen lymphocytes) are fused with myeloma cells (bone marrow primary tumor malignant cells), creating hybrid cellular line, resulting from a single fused cellular hybrid (called hybridoma) that inherited certain lymphocyte and myeloma cellular line characteristics. Appropriate fusing agent can be polyethylene glycol.

Hybridoma cells prepared like that are cultivated in an appropriate culture media, that preferably contains one or more substances that inhibit growth or survival of non-fused parental myeloma cells. For instance, as hypoxanthine-guanine phosphoribosyl transferase enzyme (HGPRT or HPRT) is missing, the culture media selected to hybridomas shall include typically hypoxanthine, aminopterin and thymidine (HAT media), substances that prevent deficient cell growth in HGPRT.

Hybridomas secrete a single specific immunoglobulin type to antigenic; what is more, as myeloma cells, hybrid cells had undefined cellular division potential. Such two characteristic combination provides different advantages on standard antiserum. While vaccinated animal derived antiserums are polyclonal antibody variable mixes that cannot be reproduced identically, monoclonal antibodies are highly specific immunoglobulins of a single type.

The only immunoglobulin type secreted by a hybridoma (monoclonal antibody) is specific to only one antigenic determinant, or epitope, in antigenic, a complex molecule with multiple antigenic determinants.

Culture media in which hybridoma cells are cultivated is tested to define monoclonal antibody production aimed against the antigenic. Preferably, monoclonal antibody bonding produced by hybridoma cells is defined by immunoprecipitation or in vitro bonding trial, including immunoassay (RIA) or immunoabsorbing trial bonded to enzyme (ELISA).

Upon hybridoma cell identification that produces antibodies with the specificity, affinity and/or activity desired, clones can be subcloned by limiting dilution procedures and cultivated by standard methods (98). Adequate media to such purpose includes, for instance, D-MEM or RPMI-1640 media. Moreover, hybridoma cells can be cultivated in vivo, for instance by cell intraperitoneal injection in mice.

Monoclonal antibodies produced by hybridoma are properly separated from culture media, ascites fluid or serum by antibody purification standard procedures, including affinity chromatography (using, for instance, protein A or protein G-Sepharose), or exchange chromatography, ions, hydroxyapatite chromatography, electrophoresis in gel, dialysis, among others.

In this context, several specialized myeloma cellular lines were developed to produce hybridomas, for instance, widely known lines in art: X63-Ag8, NSI-Ag4/1, MPCII-45.6TG1.7, C63-Ag8.653, Sp2/0-Ag14, FO and S194/5XXO. BU.1, 210. RCY3.Ag1.2.3, U-226AR, GM1500GTGAL2, U-226AR and GM1500GTGAL2. More specifically, line is SP2/0 (Sp2/0-Ag14 (ATCC® CRL-1581™).

In general, upon cell fusion, product achieved is cultivated in selective media, for instance, HAT media containing hypoxanthine, aminopterin and thymidine.

Media abovementioned enables hybrid cell proliferation and prevent non-fused myeloma cell growth that would usually continue to divide indefinitely.

Myeloma cells used are mutant without hypoxanthine-guanine phosphoribosyl transferase enzyme (HPRT), and thus, cannot use the rescue route. In surviving hybrid, lymphocyte B provides genetic information to produce such enzyme. As lymphocytes B themselves have a limited lifetime in culture (approximately two weeks), the only cells that can proliferate in HAT media are hybrid formed from myeloma and spleen cells.

As antibodies can be changed in different ways, the term 'antibody' shall be understood as covering any molecule or substance, with bonding domain with specificity required. Thus, this term covers antibody fragments, derivatives, functional equivalent and antibody homologous, including any polypeptide, including any immunoglobulin bonding domain whether natural or total, or partially synthetic. Chimeric molecules including immunoglobulin bonding domain, or equivalent, fused in another polypeptide, are consequently included. Chimeric antibody cloning and expression are provided in EP-A-0120694 and EP-A-0125023 and U.S. Pat. Nos. 4,816,397 and 4,816,567.

It has been evidenced that full antibody fragments can perform antigenic bonding function. Bonding fragment examples include (i) Fab fragment comprised by domains VL, VH, CL and CHI; (ii) Fd fragment comprised by domains VH and CHI; (iii) Fv fragment comprised by domains VL and VH of a single antibody; (iv) dAb fragment comprised by one domain VH; (v) isolate CDR regions; (vi) F(ab')$_2$ fragments, one bivalent fragment comprised by two Fab fragments bonded (vii) single-chain Fv molecules (scFv), in which a domain VH and a domain VL are bonded by a peptide linker that enables both domains to associate to form an antigenic bonding site [102, 103]; (viii) multivalent antibody fragment (dimers, trimers and/or tetramers of scFv (ix) bispecific single chain Fv dimers (PCT/US92/09965) and (x) 'diabodies', multivalent or multispecific fragments built by gene fusion (WO94/13804; [105]).

'Antibody molecule' phrase, and its different grammar forms as used herein, includes both an intact immunoglobulin molecule and an immunologically active portion of a immunoglobulin molecule.

Antibody molecules can be, for instance, intact immunoglobulin molecules, substantially intact immunoglobulin molecules and the immunoglobulin molecule portions that contain paratope including portions known in art, including Fab, Fab', F(ab')$_2$ and F(v), which portions are preferred to be used in therapeutic methods described herein.

Fab and F(ab')$_2$ portions of antibody molecules are prepared by proteolytic reaction of papain and pepsin, respectively, in substantially intact antibody molecules by widely know methods. See, for instance, U.S. Pat. No. 4,342,566 of Theofilopolous et al. Fab' antibody molecule portions are also widely known and produced from F(ab')$_2$ portions, followed by disulfide bonds linking both heaving chain portions like mercapto-ethanol, and followed by alkylation of mercaptan protein resulting form a reagent including iodine-acetamide. An antibody containing intact antibody molecules is preferred herein.

Apart from traditional hybridoma technique, there are several other widely known techniques to prepare monoclonal antibodies. Methods to prepare totally human antibodies are particularly useful. One method is phage exhibition technology that can be used to select several human antibodies, linking specifically in antigen, using enrichment methods by affinity. Phage exhibition has been completely described in literature and phage exhibition library development and screening are widely known in art, e.g., [106, 107, 108, 109]. Totally human antibodies can also be prepared by transgenic mouse immunization, providing large portion of heavy and light chains of human immunoglobulin, with one immunogen. Such mice examples are widely known in art, e. g., Xenomouse® (Abgenix, Inc.) and HuMAb-Mouse (Medarex, Inc.), see also U.S. Pat. Nos. 6,207,418, 6,150,584, 6,111,166, 6,075,181, 5,922,545, 5,545,806 and 5,569,825. Antibodies can be prepared by standard techniques, e.g. standard hybridoma techniques or phage exhibition.

Monoclonal antibodies derived by hybridoma technique from species different than human species, including mouse, can be humanized, meaning a genetically non-human antibody modified to be more human, with the purpose of preventing HAMA, when infused in humans. Antibody humanization methods are widely known in art, the most usual methods include complementarity determinant region (CDR) graft and superficial modification (also known as new surface provision). These methods have been extensively described in literature and patents, see e.g.; [110]; U.S. Pat. Nos. 5,225,539; 5,530,101; 5,585,089, 5,859,205 and 6,797,492, each one used as reference.

More specifically, present invention antibodies include the following nucleotide sequences of light and heavy chains; or sequences with 90%, 91%, 92%, 93%, 94%, 95%, 96%, 97%, 98% or 99% of sequence identity with them; or their degenerate sequences:

i) HC6/DD11

```
Heavy Chain Nucleotide Sequence (VH):
                                  (SEQ ID NO: 13)
3'ggcagggagcggtgaccgtggtccctgcgccccagacatcgaagtacc agtagctactaccgtagtaatcccttgcacagtagtacatggctgtgtcc tcagacctcagactgctcatttccaggtacagggtgttcttggcattctc tctagagatggtgaatcggcccgtcacagtgtctgcatagtagatactat atgccaaattactaatgaatgctacccactcaggcccttccctggagcc tgtcgaacccacgccattccgtagtcactgaaagtgaatccagaggctgc acaggatagtttccgggaccctccaggctgcactaagcctcccctgact cctccagcttaacttgaccggtcga5'

Light Chain Nucleotide Sequence (VL):
                                  (SEQ ID NO: 14)
5'gcaaccaattcctgcatctccaggggagaggtcaccataacctgcagt gccagctcaagtgtaagttacatgcactggttccagcagaagccaggcac ttctcccaaactctggatttatagcacatccaacctggcttctggagtcc ctgctcgcttcagtggcagtggatctgggacctcttactctctcacaatc agccgaatggaggctgaagatgctgccacttattactgccagcaaaggag tagttacccgctcacgttcggtgctgggaccaagctggagctgaaacggg ctgatgctgcaccaactgtatccctcgagacca3'
```

Sequence translation and relevant CDRs using Kabat definition method:

```
VH
                                  (SEQ ID NO: 15)
STGQVKLEESGGGLVQPGGSRKLSCAASGFTFSDYGMAWVRQAPGKGPEW

VAFISNLAYSIYYADTVTGRFTISRENAKNTLYLEMSSLRSEDTAMYYCA

RDYYGSSYWYFDVWGAGTTVTAPC

VL
                                  (SEQ ID NO: 16)
ATNSCISRGEVTITCSASSSVSYMHWFQQKPGTSPKLWIYSTSNLASGVP

ARFSGSGSGTSYSLTISRMEAEDAATYYCQQRSSYPLTFGAGTKLELKRA

DAAPTVSLET
```

More specifically, in which CDRs include the following sequences: (i) VH CDR1 sequence, as described in SEQ ID NO: 1, VH CDR2, as described in SEQ ID NO: 2 and VH CDR3, as described in SEQ ID NO: 3; and (ii) VL CDR1 sequence, as described in SEQ ID NO: 4, VL CDR2, as described in SEQ ID NO: 5 and VH CDR3, as described in SEQ ID NO: 6 or sequences with 90%, 91%, 92%, 93%, 94%, 95%, 96%, 97%, 98% or 99% of sequence identity with them.

i) AF1/CC5

```
Heavy Chain Nucleotide Sequence (VH):
                                  (SEQ ID NO: 17)
3'cggggaatgtgagagtggtgccttggccccagtagtcaaagccgtcgt acctatgcctcgtacagtaataaatgccagtgtcttcagctcttaagctg ttcatttgcaggtagacactacttttggaatcatctcttgagatggtgaa cctcccttcacagactcagcatagtatgttgcatgattattagctttgc ttctaatttcagcaacccactcaagccccttctctggagactggcggacc cagtccatccaggcgtcactaaaagtgaatccagaggcagcacaagagag tttcatggatcctccaggttgcaccaagcctcctcctgactcctccagct taacttgaccggtcga5'

Light Chain Nucleotide Sequence (VL):
                                  (SEQ ID NO: 18)
5'gattattttcttgcatctcagggagaggtcaccatgacctgcagtgcc agctcaagtataagttacatgcactggtaccagcagaagccaggcacctc ccccaaaagatggatttatgacacatccaaactggcttctggagtccctg ctcgcttcagtggcagtgggtctgggacctcttattctctcacaatcagc agcatggaggctgaagatgctgccacttattactgccatcagcggagtag ttacccatgcacgttcggtgctgggaccaagctggagctgaaacgggctg atgctgcaccaactgtatccctcgagaccaagaccagc3'
```

Sequence translation and relevant CDRs using Kabat definition method:

```
VH
                                  (SEQ ID NO: 19)
STGQVKLEESGGGLVQPGGSMKLSCAASGFTFSDAWMDWVRQSPEKGLEW

VAEIRSKANNHATYYAESVKGRFTISRDDSKSSVYLQMNSLRAEDTGIYY

CTRHRYDGFDYWGQGTTLTFP
```

-continued

VL (SEQ ID NO: 20)

DYFLASQGEVTMTCSASSSISYMHWYQQKPGTSPKRWIYDTSKLASGVPA

RFSGSGSGTSYSLTISSMEAEDAATYYCHQRSSYPCTFGAGTKLELKRAD

AAPTVSLETKTS

More specifically, in which CDRs include the following sequences: (i) VH CDR1 sequence, as described in SEQ ID NO: 7, VH CDR2, as described in SEQ ID NO: 8 and VH CDR3, as described in SEQ ID NO: 9; and (ii) VL CDR1 sequence, as described in SEQ ID NO: 10, VL CDR2, as described in SEQ ID NO: 11 and VH CDR3, as described in SEQ ID NO: 12 or sequences with 90%, 91%, 92%, 93%, 94%, 95%, 96%, 97%, 98% or 99% of sequence identity with them.

Mutations can be performed in antibody or peptide codifying DNA sequences provided herein, including in CDRs, so that a specific codon is replaced by a colon that codifies a different amino acid. Such mutation is usually performed by making as few changes as possible. Such type replacement mutation can be performed to replace an amino acid in protein resulting in a non-conservative way (i.e., by amino acid codon change belonging to an amino acid grouping, with a specific size or characteristic by one amino acid belonging to another grouping) or in a conservative way (i.e., by codon replacement of an amino acid belonging to an amino acid grouping, with a specific size or characteristic by one amino acid belonging to the same grouping). A conservative replacement usually causes a smaller change in resulting protein structure and function. A non-conservative change probably changes more the structure, activity or function of resulting protein. It shall be considered that present invention includes sequences, containing conservative changes that do not change significantly resulting protein bonding activity or characteristics.

Present invention polypeptides presented reproducibility concerning sensibility and specificity. This suggests that proteins developed can keep stable for long periods, keeping their reactive capacity. It is possible that stock buffer composition may have enable its stability, protease inhibitor use, buffer denaturing agent presence, or even due to their amino acid sequence. Stable proteins are the ones considered whenever there is diagnostic application interest.

As a second achievement, present invention discloses pharmaceutical compositions, which include monoclonal antibody abovementioned.

Pharmaceutical composition can include AcM combination of present invention.

Compositions abovementioned can also include additionally other antifungal agents.

Adequate antifungal agents can be selected of the group comprised by one (1) polyene antifungal agent, including Natamycin, Rimocidin, Filipin Nystatin, Anphotericin B e Candicidin; (2) Imidazole antifungals, including Miconazole, Ketoconazole, Clotrimazole, Econazole, Bifonazole, Butoconazole, Fenticonazole, Isoconazole, Oxiconazole, Sertaconazole, Sulconazole, Tioconazole; (3) Triazole antifungals, including FLC, itraconazole, isavuconazole, ravuconazole, posaconazole, voriconazole, terconazole; (4) Allylamine antifungals, including terbinafine, amorolfine, naftifine and butenafine; (5) Echinocandin antifungals, including Anidulafungin, Caspofungin and Micafungin.

Preferably, additional antifungal agents are AmB or FLC.

What is more, pharmaceutical compositions can be formulated with pharmaceutically acceptable vehicles or excipients, as well as any other adjuvants and diluents known by a topic technical expert with general knowledge of the area.

Pharmaceutically acceptable vehicles include excipients and auxiliaries that enable active compound processing in preparations that can be used pharmaceutically. Pharmaceutically acceptable media is widely known in art and is described, for instance, in Gennaro, Alfonso, Ed., Remington's Pharmaceutical Sciences, 18th Edition 1990, Mack Publishing Co., Easton, Pa., which is a reference text in this technical field. More specifically, pharmaceutically acceptable excipients, carriers or stabilizers do not present toxicity to receiving organism in dosages and concentrations used and include buffers like phosphate, citrate, and other organic acids: antioxidants like ascorbic acid and methionine; conservants like ammonium octadecyl dimethyl benzyl, hexamethonium chloride, benzalkonium chloride, benzethonium chloride, phenol, butyl alcohol, benzilic acid, alkyl parabens like methyl- and propylparaben, catechol, resorcinol, cyclohexanol, 3-pentanol and m-cresol; proteins like albumin, gelatin or immunoglobulins; amino acids, monosaccharides, disaccharides and other carbohydrates like glucose, mannose, sucrose, mannitol or sorbitol; polymer excipients like polyvinylpyrrolidones, Ficoll®, dextrins and polyethylene glycols; flavor agents, sweeteners, antistatic agents; chelating agents like EDTA or EGTA; ion releasing salts like sodium; metallic complexes; non-ionic surfactant agents, like polysorbates 20 and 80; lipids like phospholipids, fatty acids and steroids like cholesterol. Methods to prepare several pharmaceutical compositions are widely known, or shall be apparent at the light of present invention, by pharmaceutical technology art expert.

What is more, compositions can include additives with the purpose of increasing administration convenience, capacity to be stored, strength, bioavailability, half-life, providing isotonic degradation preparations, etc. Usual additives to pharmaceutical composition preparations are widely known in art.

Pharmaceutically acceptable media can be routinely selected according to peptide administration mode and solubility and stability.

For instance, formulations to intravenous administration can include aqueous sterile solutions that can also include buffers, diluents and other adequate additives.

Adequate formulations to parenteral administration include active compound aqueous solutions in water soluble form, for instance, soluble salts in water. Moreover, active compound suspension, including appropriate oily injection suspensions, can be administered. Adequate lipophilic solvents or media include fatty oils, for instance, sesame oil, or synthetic fatty acid esters, for instance ethyl oleate or triglycerides. Aqueous injection suspensions that can contain substances that increase suspension viscosity include, for instance, sodium carboxymethylcellulose, sorbitol and/or dextran. Alternatively, suspension can also contain stabilizers.

Pharmaceutical compositions to oral administration (in appropriate dosage) can be, preferably, but not necessarily, in tablets or capsules, in pharmaceutical industry standard size.

Pharmaceutical composition invention antibody concentration may vary widely and be selected especially based on fluid volumes, viscosities, among others. Specific administration mode shall be determinant. Compositions can also include another antibody type.

For any compound, therapeutically effective dose can be estimated initially, whether in cell culture trials, for instance, neoplastic cells, or in animal models, usually mice, rabbits, dogs or pigs. Animal model can also be used to define adequate concentration range and administration route. Such kind of information may then be used to define useful doses and administration routes in humans.

Overall, active ingredient quantity that can be combined with a pharmaceutically acceptable media to produce a single dosage form shall vary, depending on the subject to be treated and the specific administration mode. Active ingredient quantity that can be combined with a pharmaceutically acceptable media to produce a single dosage form shall usually be the composition quantity that produces a therapeutic effect. Usually, out of one hundred percent, such quantity varies from approximately 0.01 t0 99% of active ingredient, preferably approximately 0.1 to 70%, more preferably from 1 to 30% of active ingredient, in combination with a pharmaceutically acceptable media.

Invention pharmaceutical compositions can be administered by several administration routes, including, among other, oral, sublingual, nasal, intravenous, intramuscular, intraperitoneal, intra-joint, subcutaneous, cutaneous, transdermal, but not limited to them.

As a third achievement, present invention discloses the use of monoclonal antibody abovementioned to prepare a drug to treat fungal infections. The use can be in combination with other active antifungal agents, including AmB and/or FLC.

'Combination' can be understood as administration of two or more therapeutic agents to treat a disease, condition and/or disorder. Such administration includes co-administration of two or more therapeutic agents in substantially simultaneous way, as in a single capsule with fixed active ingredient ratio or in multiple capsules and separated to each active agent. Moreover, administration can be sequential.

Invention antibodies can be administered in combination with others with standard drugs to treat fungal infections. Preferably AmB, that has broad spectrum against yeast and filamentous fungi and FLC, that has fungicidal action against *Cryptococcus*.

Both drugs present their actions in ergosterol, and AmB is directly bonded to ergosterol, forming pores and FLC, bonding to lanosterol 14 alpha demethylase enzyme, which is ergosterol synthesis key enzyme.

As a fourth achievement, present invention discloses a fungal infection diagnostic method that includes:

(i) providing monoclonal antibody or composition abovementioned with a sample achieved from an individual (ii) contacting monoclonal antibody or composition abovementioned with the sample to be tested for enough time and under enough conditions to develop antigenic/antibody complex development; and (iii) detecting antigenic/antibody complex developed in previous stage through a detection technique capable of generating detectable signal at present of antigenic/antibody complex abovementioned.

Samples can be selected from the group, including saliva, urine, serum, blood, Bronchoalveolar Lavage, peritoneal fluid or liquid, or any other biological fluids of the individual.

Antibody can include a detectable marker, including a fluorescent, radioisotope, chemiluminesent or enzymatic, including wild radish peroxidase, alkaline phosphatase or luciferase.

Several fluorescent materials are known and can be used as markers. They include, for instance, fluorescein, rhodamine, auramine, Texas red, AMCA blue and Lucifer yellow. A specific detection material is the anti-rabbit antibody prepared in goats and conjugated with fluorescein through isothiocyanate. Peptide SLC34A2 or its bonding partner(s) can also be marked as a radioactive element or with an enzyme. Radioactive marker can be detected by any of currently available count procedures. Preferred type can be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{123}$I, $^{125}$I, $^{131}$I, $^{186}$Re, $^{99}$Tc, $^{67}$Ga, $^{201}$Tl and $^{111}$In.

Enzyme markers are likewise useful, and can be detected by any colorimetric, spectrophotometric, fluorospectrophotometric, amperometric or gasometric used at present. Enzyme is conjugated in the particle selected by bridge molecule reaction, including carbodiimides, diisocyanate, glutaraldehyde and similar. Many enzymes that can be used in these procedures are known and can be used. Preferred ones include peroxidase, β-glucuronidase, β-D-glucosidase, β-D-galactosidase, urease, glucose oxidase plus peroxidase and alkaline phosphatase. U.S. Pat. Nos. 3,654,090; 3,850, 752; and 4,016,043 are referred to by means of example, for alternative labeling method and material disclosure.

Detection media can be known in the art. A non-limiting example of detecting media can be conjugated by an antibody coupled to a signal generating compound, capable of generating a detectable signal.

Alternatively, antibody can be bonded to a solid support, that can accommodate trial automation. Adequate solid supports include, but not limited to, glass or plastic blades, tissue culture plates, micro-titration well, pipe, chips or particles like beads, selected of, but not limited to, latex, polystyrene or glass beads.

Invention can be performed in any method known in technical field can be used to connect the antibody to solid support, including covalent and non-covalent bondings, passive absorption or bonding portion parties bonded to antibody and solid support. Antigenic and antibody bonding can be performed in any adequate recipient to contain reagents. Examples of such vessels include micro-titration plates, test tubes and microcentrifuge tubes.

Antibodies can also be used, especially to differentiate invasive fungal infections from bacterial infections at hospital environment and with high risk and/or immunocompromised patients.

As a fifth achievement, invention discloses a fungal infection diagnostic kit that includes monoclonal antibody or composition abovementioned and instructions for use.

The kit can also include antigenics/antibody complex detection media, which can include a signal generator, capable of generating a detectable signal. For instance, antibody can bear a label with a detection media that enables detecting the antibody whenever it is bonded to its relevant antigenic.

Detection media can be a fluorescent labeling agent, like fluorescein isocyanate (FIC), fluorescein isothiocyanate (FITC), and among others, an enzyme, like wild radish peroxidase (HRP), glucose oxidase or similar, a radioactive element like $^{125}$I or $^{51}$Cr that produces gamma ray emissions, or a radioactive element that releases positrons that produce gamma rays after encounters with electrons present at test solution, like $^{11}$C, $^{15}$O or $^{13}$N. Bonding can also be detected by other methods, for instance, through avidin-biotin. What is more, labeling agent can be any enzyme included in oxidase groups (like radish peroxidase), luciferases, peptidases (like caspase-3), glucosidases (like beta-galactosidase) and phosphatases (like alkaline phosphatase).

Detection media bonding is widely known by topic technical area experts. Thus AcM produced can be metabolically labeled by incorporating amino acids containing radio isotopes in culture media, or can be conjugated or coupled to a detection media through activated functional groups.

Adequate fungal infection diagnostic kits, to present invention can be based preferably in the following techniques: ELISA, Lateral Flow Immunochromatographic Assay and Liquid Microarrays.

ELISA test in an immunoenzymology test based on antigenic-antibody reactions that can be detected through enzymatic reactions.

Purified antigenics are fastened over appropriate solid supports, (for instance, a polystyrene plate). Next, the sample is added to wells, and in case the sample is of a positive individual to the condition abovementioned, specific antibodies shall bond to antigenics fastened in solid support.

After this stage, antibodies bonded to markers are added (peroxidase) against antibodies bonded to antigenics. Thus, in wells where antigenic-antibody bonding takes place, coloration occurs, as substrate is added to marker.

Lack of coloration points out lack of antibody in sample against substrate antigenic.

Lateral flow immunochromatographic assay is comprised by overlapping of different membranes assembled over support adhesive card. Antibody is immobilized in nitrocellulose membrane and the latter is overlapped by membrane that receives the sample to be tested in card proximal region. A membrane impregnated with compounds (conjugated) that disclose the reaction is located in nitrocellulose membrane end and an absorbing membrane in distal region. Resulting strips are enclosed in plastic devices.

The test uses samples (serum, plasma or blood) in volume to be assessed, followed immediately by buffer application. Buffer solution enables migration of conjugated and proteins included in the sample.

Sample migration occurs by capillarity until test line area and control at room temperature. Test visual reading is performed after complete sample/buffer migration, that usually takes place within 15 minutes. Test and control line viewing points out positive result to disease. Lack of test line view with simultaneous control line labeling points out negative result and lack of control line view invalidates the test.

Liquid microarrays is a trial performed in suspension with polystyrene microsphere matrix, with 5.6 or 6.5 micrometer diameter, that work as solid support to antibody coupling through covalent bonding. Antibody-antigenic reaction detection occurs with assistance of a detection molecule (fluorophore), especially phycoetritin. In this system, it is possible to use a mix of different microsphere types, that have uniform size, however, they release intensities with different fluorescence.

Coupling takes place by means of covalent boning between microsphere carboxylated surface and primary amines present in antibodies.

Microspheres have internal dyers that have individual codes that differentiate concerning single emission profile. Thus, it is possible to perform multiple analyte simultaneous analysis, as each microsphere coupled covalently to a capture reagent, can be differentiated by its spectrum.

Reaction reading is performed through microsphere aspiration in solution that are transported to a special chamber. Then, microspheres are centralized in continuous flow and in individualized way, so that both lasers intercept a single particle at a time and identify accurately each code.

As a sixth aspect, invention provides a fungal infection treatment kit, including
(i) monoclonal antibody, as provided in claim 1 or a composition, as provided in any claims 2 to 4; and
(ii) Antifungal agent;
(iii) Instructions to use components in combination.

As a seventh achievement, invention provides a fungal infection treatment method including administration of a therapeutically efficient quantity of antibody of composition abovementioned in an individual requiring the former.

As an eighth achievement, invention provides an antibody or composition to be used in fungal infection treatment in an individual requiring the former.

Treatment use can be designed to human and veterinary use. Preferably, the individual treated is a human being requiring treatment.

Effective quantity for a human individual shall rely on disease state severity, individual general health, age, weight, sex, diet, administration time and frequency, drug combination/combinations, reaction sensibilities, and tolerance/response to therapy. Thus, doses to be provided rely on several factors that cannot be measured before clinical test studies are performed. The topic technical expert, however, knows how to achieve adequate doses to different treatment.

The examples abovementioned are for illustration only, and they shall be used only for a better understanding of developments provided in present invention, and they shall not, however, be used with the purpose of limiting of objects described.

EXAMPLES

Example 1—Cellular Types and Growth Conditions

Fungi species used included *C. neoformans* (serotype A, clinical isolate H99 ATCC 208821), *C. gatti* (serotype B, strain R265 ATCC MYA-4093), *C. albicans* (ATCC 90028), *C. neoformans* acapsular (mutant Cap67 ATCC 52817), *Giardia lamblia* (ATCC 30957), human lung line cell A549 (ATCC CCL-185), *Escherichia coli* (ATCC 9637) and *Staphylococcus aureus* (ATCC 25923). For in vitro and in vivo trials, cells were cultivated in minimum media (glucose 15 mM, $MgSO_4$ 10 mM, $KH_2PO_4$ 29.4 mM, glycine 13 mM, thiamin-HCl 3 μM, pH 5,5) and kept under agitation for 2 days at 30° C. Cells were achieved by centrifugation, washed in PBS and counted in Neubauer chamber.

For hybrid cell development, line SP2/0 myeloma cells (Sp2/0-Ag14 (ATCC® CRL-1581™), along with cells B originated from animal spleen previously immunized with chitooligomers and by fungus *C. gattii*. Cultivation was performed in DMEM (LONZA) media supplemented with Glutamine 6.4 mM/SFB 10%. All content was transferred to bottle type T 25 $cm^2$ (Corning®) and incubated at 37° C./5% $CO^2$ until reaching feasibility required.

Example 2—Animal Immunization

Mice immunization was performed as follows line Balb/C mice were immunized in intraperitoneal form (i.p.; 200 μl) at every 15 days. Thus, two different strategies were used: in first strategy, animals were immunized via i.p. with *C. gattii* ($1 \times 10^6$ cell/ml) previously fastened in paraformolaldehyde (PFA) 4% and washed in PBS, followed by two immunizations via i.p. with 15-day interval with 200 μg of free chitotriose (molecule trimer comprised by units of β-1,4-N-acetylglycosamine-β-1,4-GlcNAc), using as adjuvant aluminum hydroxide ($Al(OH)_3$—1.5 mg), complying with 1:1 ratio (v/v). Finally, animals were immunized by intravenous route (i.v.) with 50 µg of free chitotriose, using PBS as media. The second strategy was identical to the first one, except for additional immunization introduction with free chitotriose with Al(OH)$_3$ before final injection, i.v. In both strategies, bleeding was performed by the end of immunizations, to check antibody titration in serum through indirect ELISA. Pre-immune serum was collected for every animal to be used as screening control and cut-off.

Example 3—Fusion

After four/five immunizations, animal splenectomy to process splenocytes to execute cellular fusion with murine myeloma cells SP2/0 (ATCC), adapted from Köhler & Milstein 1975.

Splenocytes and SP2/0 are fused assisted by solution PEG 3000-3700 at 50%, pre-heated at 37° C. Later, cell homogenate was volumed in DMEM media supplemented with Glutamine 6.4 mM/Antibiotic (ATB) 1×/SFB 20% at 1×10$^8$ cell/100 mL ratio. All suspension volume was transferred to 96-well to cellular culture (Corning) at 100 µL/well, and 3 wells of the last plate were added 6×10$^4$ cells SP2/0 that were used as selection media control. Plats were then incubated at 37° C., 5% CO$_2$ for 24 hours and one day after initial incubation, 100 µL of DMEM media supplemented with Glutamine 6.4 mM/ATB 1×/SFB 20%/hypoxanthine, aminopterin, thymidine (HAT) 2× were added to plate wells to start viable hybrid cell selection process resulting from fusion process for 14 days. Well supernatant was used to perform specific indirect ELISA trial against chitotriose.

Example 4—Direct Elisa

Indirect ELISA (97) was performed in two moments. 1) Animal serum antibody titration determination by the end of immunization process; 2) Specific polyclonal and monoclonal antibody determination to chitooligomers produced by hybridoma.

Example 4.1—ELISA for Animal Serum Titration Determination 96-well plate was coated with chitotriose conjugated at BSA at 0.5 µg/ml concentration in PBS and incubated at night at 4° C. After incubation, the plate was incubated with PBS/BSA 1% for 1 hour at 37° C., later washing was performed and animal serum was added in different dilutions and incubated for 2 hours at 37° C. The plate was washed three times with PBS/Tween 0.05% and conjugated murine anti-IgG and anti-IgM was added to peroxidase and incubated for 2 hours at 37° C. After the incubation, the plate was washed, as previously described and incubated with Tetramethylbenzidine (TMB) and incubated for 30 minutes at 37° C. The reaction was stopped with HCl 1 N and 450 nm reading was achieved in spectrophotometer.

Example 4.2—ELISA for Polyclonal and Monoclonal Antibody Determination

The same procedure described previously was performed, and the difference was that reaction primary antibody originated from hybridoma cultivation supernatant.

Example 5—Polyclonal Hybridoma Cloning

Positive polyclonal hybridoma cloning in ELISA trial provided in previous item is performed through cell count in Neubauer chamber, so that such cellular suspension dilution presents, by the end, 1 cell/well concentration, in 200 µl final volume. Cultivation is incubated at 37° C., 5% CO2 for 14 days and observing clonality (monoclonal or polyclonal) as from 5th day. Cultivations that remain viable and monoclonal are submitted again to ELISA trial to check specificity before antigenic defined.

Example 6—Selected Clone Isotyping

Isotyping of previously selected clones by ELISA was performed by commercial kit—Rapid ELISA Mouse mAb Isotyping Kit—ThermoFisher. Thus, 1:10 dilution was performed of supernatant of clone cultivation and added to specific test plate. Kit defines murine isotype presence IgG1, IgG2a, IgG2b, IgG3, IgA and IgM present in sample quickly and efficiently.

Example 7—Selected Monoclonal Antibody RNA Extraction

RNAM extraction was performed for each monoclonal antibody originated from cultivation bottle T-25, in which only cells were collected by means of centrifugation (400 g for 10 minutes at room temperature). Each monoclonal antibody pellet was used to total RNA extraction with RNeasy Mini Kit (Qiagen) commercial kit, following protocol set forth by manufacturer.

Example 8—Polymerase Chain Reaction Via Reverse Transcriptase (RT-PCR)

Before RT-PCR stage, monoclonal cDNA synthesis was performed by means of Super Script III First-Strand Synthesis System (INVITROGEN) commercial kit.

Later, PCR was performed with primer oligonucleotides selected from the publication of Zhou et al. 1994, as they are described as universal primers to murine heavy variable chain (VH) and light variable chain (VL), as provided in table 2. Sequences achieved were assessed before Kabat database.

RT-PCR was performed according to the following conditions: initial denaturation 94° C./5 minutes, denaturation 94° C./2 minutes, annealing 48° C./1 minute, extension 72° C./1 minute and 30 seconds, repeated for 30 times and final extension 72° C./1 minute to VH chain and the same conditions to VL, however with annealing temperature of 55° C./1 minute.

Band viewing was performed in agarose gel 1.5% at approximate size 570 pb to VH and 370 pb to VL.

TABLE 2c

| Synthetic oligonucleotides used in RT-PCR reaction to codifying cDNA amplification to urine VH and VL from end 5' | |
| --- | --- |
| | Sequence |
| VH-Fw | |
| 307 | 5'ATG(GA)A(GC)TT(GC)(TG) GG(TC)T(AC)A(AG)CT(GT)G (GA)TT3' |
| 308 | 5'ATG(GA)AATG(GC)A(GC)CT GGGT(CT)(TA)T(TC)CTCT3' |

TABLE 2c-continued

Synthetic oligonucleotides used in RT-PCR
reaction to codifying cDNA amplification
to urine VH and VL from end 5'

| | Sequence |
|---|---|
| 309 | 5'GATGTGAAGCTTCAGGAGTC3' |
| 310 | 5'CAGGTGCAGCTGAAGGAGTC3' |
| 311 | 5'CAGGTGCAGCTGAAGCAGTC3' |
| 312 | 5'CAGGTTACTCTGAAAGAGTC3' |
| 319 | 5'GAGGTCCAGCTGCAACAATCT3' |
| 320 | 5'GAGGTCCAGCTGCAGCAGTC3' |
| 321 | 5'CAGGTCCAACTGCAGCAGCCT3' |
| 322 | 5'GAGGTGAAGCTGGTGGAGTC3' |
| 324 | 5'GATGTGAACTTGGAAGTGTC3' |

VH-Rev

| γ1 | 5'TGGACAGGGATCCAGAGTTCCA GGTCACT3' |
|---|---|

VL-Fw

| 353 | 5'GACATTGTGATGACCCAGTCT3' |
|---|---|
| 362 | 5'GATGTTTTGATGACCCAAACT3' |
| 364 | 5'GATATTGTGATAACCCAG3' |
| 365 | 5'GACATTGTGCTGACCCAATCT3' |
| 390 | 5'GATATTGTGCTAACTCAGTCT3' |
| 391 | 5'GATATCCAGATGACACAGACT3' |
| 392 | 5'GACATCCAGCTGACTCAGTCT3' |
| 393 | 5'CAAATTGTTCTCACCCAGTCT3' |
| 394 | 5'CAGGCTGTTGTGACTCAGGAA3' |

VL-Ver

| K-18 | 5'TACAGTTGGTGCAGCATC3' |
|---|---|

Example 9—Selected Monoclonal Antibody DNA Sequencing

Selected monoclonal antibody DNA sequencing was performed according to protocol described in BigDye Terminator v3.1 (Life Technologies) commercial kit, and the same primers described in PCR were used (example 8). What is more, each sequencing identity was assessed using BLAS—Basic Local 54 Search Alignment Tool (www(dot)ncbi(dot)nlm(dot)nih(dot)gov/blast) tool, within VH and VL sequences of selected hybridomas. Sequences were assessed using the program SeqMan (DNAStar), and identify CDR1, 2 and 3, gene sequences were submitted to analysis by IgBlast tool (IgBlast Tool—NCBI—NIH; https://www(dot)ncbi(dot)nlm(dot)nih(dot)gov/igblast/).

Example 10—Monoclonal Antibody (AcMs) Purification

AcMs purification is performed in three stages: PEG precipitation, molecular exclusion chromatography and ion exchange chromatography in high efficiency liquid chromatography (AKTA Purifier 10; GE Healthcare).

PEG precipitation was performed submitting cultivation supernatant to precipitation with polyethylene glycol (PEG 6000) at 4% concentration (p/v). Suspension was sustained by agitation for three hours at room temperature (TA), and then, material centrifugation was carried out (1600×g; 30 minutes; 4° C.).

Supernatant achieved upon centrifugation was submitted to a second precipitation stage with PEG 6000 at 6% concentration (p/v), followed by centrifugation in the the same conditions described previously. Precipitate achieved was dissolved in 15 mL volume of buffer solution Tris-HCl 50 mM, pH 8.0.

Material achieved after second precipitation was fractioned through molecular chromatography exclusion (SEC) using Superdex 200 High Load 26×60 (320 mL) column, with 3.0 mL/min flow, and buffer solution Tris-HCl 50 mM, pH=8.0 is used as eluent, with collection volume equal to 10 mL.

After selection and pool of samples originated from SEC, anionic exchange chromatography was performed in Pores HQ 10×100. Fraction elution was performed in 5.0 mL/min flow in buffer solution Tris-HCl 50 mM, pH 8.0 with saline gradient in two segments (20% and 50%). Fractions were collected with 4.0 mL volume.

Achieved sample homogeneity in each purification process stage was assessed by denaturing electrophoresis in polyacrylamide gel (SDS-PAGE). To estimate the molecular weight (PM), Precision Plus Protein™ Dual Color (Bio-Rad) commercial standard was used. Proteins were developed with Coomassie Blue R350 dying solution and result assessed through Image Lab™ software, after image processing in Gel Doc™ XR+(BIO RAD) system.

Example 11—Affinity Constant Determination and Dissociation by Surface Plasmon Resonance (SPR)

SPR experiments were performed using BIACORE X (GE Healthcare) system equipped with chip sensor CM5. Linkers tested included AcM AF1/CC5 and HC6/DD11 (described later in Results), which were immobilized using amine coupling. Both flow cell surfaces were activated for 7 min with mix 1:1 of 0.1 M NHS (N-hydroxysuccinimide) and 0.1 M EDC (3-(N, N-dimethylamine) propil-N-ethyl-carbodiimide) at 10 μl/min flow rate. Linkers were immobilized at 100 μg/ml concentration in sodium acetate at 10 mM, pH 5.0. Ester waste waste deactivated with 7 min inject of ethanolamine 1 M, pH 8.0.

To collect kinetic bonding data, analyte BSA-(GlcNAc)$_3$ was injected over two flow cells in 0.1 and 0.6 nM concentrations in 5 μl/min flow rate and 25° C. temperature using buffer HBS-EP (10 mM HEPES, 150 mM NaCl, 3 Mm EDTA and 0.005% P20) pH 7.4.

Data was adjusted by means of concentration in single interaction template (1:1) of linker and analyte using global data analysis option, that enables setting all graphs achieved simultaneously. All data was assessed in BiaEvaluation 4.1 software.

Example 12—Bonding Site Determination Trial 96-well plates were coated with chitotriose-BSA at 0.5 μg/ml concentration in PBS and incubated at night at 4° C., followed by incubation with PBS/BSA 1% for 1 hour at 37°. Later, washing was performed (PBS/Tween 0.05%) and wheat germ lectin solution (WGA) was added, peroxidase conjugated at 25 µg/ml concentration, used as reaction control. Cold WGA was used to test system with the purpose of blocking boning site at chitotriose-BSA and AcMm to check if there would be bonding at chitotriose-BSA. Cold WGA was incubated for 1 hour at 37° C., and then washed three times with PBS/Tween 0.05%. AcM were incubated at 25 µg/ml concentration, followed by incubation for 2 hours at 37° C. Plate was washed three times with PBS/Tween 0.05% and were incubated again for 2 hours at 37° C. with conjugated murine anti-IgM at peroxidase (1:10000). Systems were washed as previously described and incubated with TMB for serological reaction development, as above-mentioned.

Example 13—Functional Trials

Example 13.1—Indirect ELISA Against Sound Cells Adapted From Stearns et al. 1999

For this test, *C. neoformans* (H99), *Candida albicans, Giardia lamblia,* human lung line cell A549 (ATCC), *Escherichia coli* and *Staphylococcus aureus.* Cells were washed in PBS three times and suspended at $10^7$ cell/ml density in poly-L-Lysine (5 µg/ml in PBS) for adherence at night at 4° C. The next day, plates were blocked with PBS/BSA 5% and incubated for 1 hour at 37° C., then they are incubated for 1 hour at 37° C. with anti-chitooligomer AcM at 50 µg/ml concentration and diluted at 5 µg/ml, washing with PBS/Tween 0.05% was performed for 3 times and anti-IgM murine peroxidase was added diluted 1:5000 and incubated for 2 hours at 37° C. Plates were washed again and TMB was added and incubated for 30 minutes at 37° C.

Reaction was stopped with HCl 1 N and reading with spectrophotometer at 450 nm. After this trial, seriated dilutions were performed at density of cells $10^7$ until 10 cells/ml to fungi and $10^7$ until 104 cells/ml to other cellular types and tested of AcM anti-chitooligomer at 25 µg/ml concentration, followed by the same procedures abovementioned.

What is more, similar trials were performed with other chitin derivative, chitosan (deacetylated form) in different concentrations, keeping the same procedures described.

Example 13.2—Dot Blot Against Sound Cells Adapted From Nimrichter et al. 2007

*C. neoformans* (H99) and *Candida albicans* in $10^7$ cell/ml density until 10 cells/ml were suspended in poly-L-Lysine solution (5 µg/ml in PBS) and 10 µl were loaded in nitrocellulose membranes. Then, the same steps for ELISA were followed, however, 25 µg/ml concentration of AcM anti-chitooligomers. Membrane was cut and deposited in 96-well plates, to which 50 µl TMB was added and incubated for 30 minutes at 37° C. Volume was removed and transferred to a new plate, to which stop reaction was added with HCl 1 N and read with spectrophotometer at 450 nm.

Example 13.3—Activity Assessment of AcM Anti-Chitooligomer Against Sound Cells by Immunofluorescence Adapted From Rodrigues et al. 2008

Fungal cells ($10^6$ cells)) were fastened (cacodylate paraformolaldehyde buffer 4%; 30 min) and blocked later (PBS/BSA 1%; 1 hour). Then, they were incubated with AcM anti-chitooligomer(25 µg/mL; 1 h at 37° C.) After washing with PBS, cells were incubated with mouse anti-IgM antibody conjugated at Alexa 568 (SIGMA; 1:1000).

After PBS washing, cells were incubated with 25 µM of white calcofluor (Invitrogen) and washed again. Cellular suspensions were assembled in glass blades and assessed under microscope Olympus AX70, coupled to camera system (QImaging Retiga 1300) and assessed in QCapture suite V2.46 software.

Example 13.4—Minimum Inhibiting Concentration (MIC) Adapted From Joffe et al. 2017

*C. neoformans* cells were cultivated in RPMI 1640 buffered with MOPS in pH 7 at $10^5$ cell/well density in 96-well plates in 200 µl final volume. Systems were supplemented with AcM at concentration (25 to 0.05 µg/ml), AmB (1 to 0.1 lµg/ml) or FLC (8 to 2 µg/ml), alone or in association. After 48 hours of incubation at 37° C. under agitation, cells were suspended by pipetting for spectrophotometer reading at 592 nm wavelength.

Example 13.5—Biofilm Development Adapted From Joffe et al. 2017

*C. neoformans* (H99 and Cap67) and *Candida albicans* were cultivated in Sabouraud media for 24 hours at 30° C. Cellular suspensions were centrifuged for 5 minutes at 3000 g, washed 3 times in PBC and suspended in minimum media (20 mg/ml thiamin, 30 mm glucose, 26 mM glycine, 20 mM MgSO4, and 58.8 mM KH2PO4). Then, they were added to 96-well plates (100 µl/well—1×$10^6$ células/ml) and cultivated for 48 hours at 37° C. at presence of AcM (HC6/DD11 and AF1/CC5) and AcM anti-GXM 18B7 (only to H99) at 25 µg/ml concentration, keeping under agitation for 30 minutes, for AcM total homogenization with fungi. As control, drug AmB was used at 1 µg/ml concentration.

Two analysis systems were performed: in the first, cells were washed, so that non-adhering cells were removed and only cells bonded to biofilm under development remained; in the second system, cells were not washed and all cells adhered or not to substrate were quantified.

Viable cell metabolic activity in both trials was assessed by the method based on decrease of XTT (2-methoxy-4-nitro-5-sulfophenyl)-5-[(phenylamino) carbonyl]-2H-tetrazolium hydroxide) in spectrophotometer at 492 nm of wavelength.

Example 13.6—Melanization Trial Adapted From Walker et al. 2010

*C. neoformans* cultivation was performed as paragraph and cellular suspension (1×$10^6$ cells/ml) was cultivated for 72 hours in minimum media supplemented with 1 mM of L-DOPA in 96-well plate of U-shape bottom. Antibodies HC6/DD11 and AF1/CC5 were added to minimum media within 25 to 0.05 µg/ml concentration range. The plate was centrifuged and pigment development quantification was defined densitometrically upon image scanning by iBright FL1000 Invitrogen equipment.

Example 14—Survival Trial

Balb/C line mice (n=7) were lethally challenged via i.p. with $10^5$ cells in PBS of *C. neoformans* (H99) and treated 2 hours later with 100 µl of AmB (2.5 mg/kg and 0.25 mg/kg), 100 µl of AcM (85 µg/ml) and 100 µl of AcM and AmB combined solution (0.25 mg/kg). Control animals were challenged only by *C. neoformans* (H99) or only with 100 µl of a solution of PBS, AmB (2.5 mg/kg) or AcM (85 µg/ml)

without fungus (adapted from Liedke et al.). Survival rate was achieved and analysis was extended up to 90 days after infection, presenting statistical value with $p<0.005$.

Example 15—Molecular Modeling

HC6/DD11 and AF1/CC5 antibody variable region sequences were achieved by sequencing and translated to achieve corresponding amino acid sequences using biocomputing tool ExPASy Translate tool (https://web.expasy.org/translate/).

Sequence humanization was performed using IMGT (http://imgt.org/3Dstructure-DB/cgi/DomainGapAlign.cgi) database, to achieve more identical human germinative repertory (percentage identity) to VH and VL chains.

Humanized sequences achieved from more identical human repertory were aligned separately using blastp (https://blast(dot)ncbi(dot)nlm(dot)nih(dot)gov) tool against PDB (Protein Data Bank—https://www(dot)rcsb(dot)org) database to select mold protein. Three-dimension template development was performed using Modeller 9.19 program.

Example 16—Murine Monoclonal Antibody Development Against Chitooligomers Through Hybridoma Technology

Example 16.1—Immunized Animal Titration Against *C. gattii* E Chitotriose

Two immunization strategies were developed, and in both, bleeding was performed by the end of the last immunization, to check antibody serum titration (FIG. 6). Regardless of strategy adopted, 1:3200 titration was achieved, to IgG and IgM dosed in serum, being used to screening and chitotriose-BSA. To set forth the cut line, absorbance values were used, achieved in reactions with pre-immune serum. Three animals were used to proceed with fusion.

Example 16.2—AcM Producing Hybridoma Selection by ELISA 3 fusions were performed from 3 animal splenectomy. Splenocytes were fused with Sp2/0 and 172 hybridomas were achieved, 4 of which producing reactive antibodies against chitotriose.

Four polyclonal antibody-producing hybridomas were submitted to cloning, generating 541 AcM producing hybridomas. In this group, 58 reactive against chitotriose hybridomas were selected, and 10 hybridomas were finally selected to later studies, which presented higher response (optical density–D.O.≥3×cut-off) in ELISA tests, using chitotriose-BSA as primary antigenic.

Example 16.3—AcM Purification

2 AcMs were purified through Ion Exchange Chromatography and assessed by electrophoresis in polyacrylamide gel (FIG. 8).

Every IgM aliquot presented two main IgM bands, corresponding to heavy (~70 kDa) and light chains (molecular mass ranging between ~23-24 kDa) of immunoglobulin M. Other bands observed are suggestive to IgM partial decrease and micro protein and glycidic heterogeneity.

Example 16.4—CDR Identification

AcM AF1/CC5 and HC6/DD11 producing hybridomas had their RNA extracted to generate a cDNA, and consequently, be amplified from PCR VH and VL of both AcM. After amplification, chains were sequenced and had their CDRs identified through a Kabat number system, which is a scheme to number amino acid waste in antibodies based on variable regions. With CDR identified, alignment was performed through database of immunoglobulin, IgBlast, to check AcM identify with immunoglobulins deposited in GeneBank.

Thus, a very high identity of both AcM was achieved, however they had punctual differences in HC6/DD11 VH CDR, where there was an amino acid change in relation to deposited in bank and AF1/CC5 VH and VL CDR3 change, and heavy chain CDR3 had a higher change percentage rate, reaching 95% of identity, against 99% of other CDR3 pointed out, as provided by tables 3 and 4, respectively.

TABLE 3

| AcM HC6/DD11 CDR identification. | | |
| --- | --- | --- |
| Sequence | GeneBank Deposited Sequence | Identity (%) |
| HC6/DD11 Heavy Chain (VH) | | |
| CDR1 GFTFSDYGMA (SEQ ID NO: 1) | AAO19699.1 | 100 |
| CDR2 ISNLAYSIY (SEQ ID NO: 2) | AAO19699.1 | 100 |
| CDR3 DYYGSSYWYFDV (SEQ ID NO: 3) | AAO19699.1 | 99 |
| Light Chain (VL) | | |
| CDR1 SASSSVSYMH (SEQ ID NO 4) | AAB05147.1 | 100 |
| CDR2 STSNLAS (SEQ ID NO: 5) | AAB05147.1 | 100 |
| CDR3 QQRSSYPLT (SEQ ID NO: 6) | AAB05147.1 | 100 |

TABLE 4

| AcM AF1/CC5 CDR identification. | | |
| --- | --- | --- |
| Sequence | GeneBank Deposited Sequence | Identity (%) |
| AF1/CC5 Heavy Chain (VH) | | |
| CDR1 GFTFSDAWMD (SEQ ID NO: 7) | AMN90557.1 | 100 |
| CDR2 IRSKANNHA (SEQ ID NO 8) | AMN90557.1 | 100 |
| CDR3 HRYDGFDY (SEQ ID NO: 9) | AMN90557.1 | 95 |

TABLE 4-continued

AcM AF1/CC5 CDR identification.

| Sequence | GeneBank Deposited Sequence | Identity (%) |
|---|---|---|
| Light Chain (VL) | | |
| CDR1 | SASSSISYMH (SEQ ID NO: 10) | AAA63380.1 | 100 |
| CDR2 | DTSKLAS (SEQ ID NO: 11) | AAA63380.1 | 100 |
| CDR3 | QRSSYPCT (SEQ ID NO: 12) | AAA63380.1 | 99 |

Example 16.5—ELISA Using PL

PL is a lysine polymer that provides positive load to bottle, place or blade surface, which work as cellular substrate. Fungi can have cellular wall formed by chitin, which is comprised by long chins of N-acetylglucosamine, a polymer that has negative load. *C. neoformans*, apart from chitin, has a polysaccharide capsule comprised by glucuronoxylomannan and galactoxylomannan, which also has negative load in its structure. Due to such background, PL was used to change plate charge (positive) and consequently manage to perform cell adherence to such surface.

In this trial, $10^7$ cell/ml of *C. albicans* were used to perform an absorbance curve, in which it was observed that there was a 25 µg/ml concentration reliable signal of both AcM, as above such value the curve starts to enter in plateau, as provided in FIG. 9. With the purpose of checking both AcM detection sensibility, cell saturation curve was performed. It was defined that maximum sensibility level of both AcM was $10^3$ cells/ml. This conclusion was reached due to reaction signal detection considered positive 3 times greater than cut-off (reaction blank). However, signal achieved by antibody HC6/DD11 was slightly more sensitive in concentrations of $10^4$ and $10^5$ cells/ml, and to AF1/CC5, a plateau to both cells was achieved.

Example 16.6—Dot Blot Using PL

The principle used in this trial was the same of ELISA and was based on the load presented by fungi. As nitrocellulose membrane has negative load, PL was used to check positive load to fungus, and consequently have bond to membrane.

As provided in FIG. 11, it was initially diluted in 5 µg/ml of PL at $10^7$ cell/ml concentration and diluted in base 10. In this trial, it was evidenced that AcM HC6/DD11 was capable to bond to *C. albicans* up to $10^4$ cell/ml order, which counters *C. neoformans*, that was identified to $10^6$ cell/ml order. 3 independent experiments were performed to each trial. Example 16.7—Immunofluorescence From reliable and ELISA and Dot Blot trials, biological activity validation tests. Thus, AcMs were used through immunofluorescence (IF), using the pathogen *Candida albicans* as template. AcMs were efficient at fungal cellular wall labeling, showing the same profile whenever standard marker is used (lectin), data not provided. This experiment was performed for 3 times and showed the same response pattern, however FIG. 12 provides an isolate experiment data.

Example 16.8—Melanization Trial

*C. neoformans* skill to produce melanin pigments represents its second most relevant virulence factor, after polysaccharide capsule presence. Due to that, it was proposed assessing AcM activity in melanin deposit in fungal cellular wall.

AcM HC6/DD11 e AF1/CC5 established concentrations were 0.2 to 25 µg/ml. L-DOPA was used with substrate to melanization.

Pigmentation in *C. neoformans* was assessed through brown to black sedimentation observation in 96-well plate bottom. To document pigmentation or inhibition, plates were photographed over white surfaces (clear bottom), to enable differentiation between pigmented and non-pigmented populations. It shall be noted that every AcM dose presents fungal growth, however with negative pigmentation or partial inhibition.

It was evidenced that treatments with AcM HC6/DD11 inhibit melanization partially, until concentration up to 6.2 µg/ml (p<0.05), however in lower concentrations there is not significant inhibition (p>0.05). AcM AF1/CC5 inhibits melanization up to 6.2 µg/ml (p<0.001) concentration, and in 3.2 and 1.6 µg/ml (p<0.05) concentrations, there is partial inhibition, and in lower concentrations there is not significant inhibition (p>0.05). (FIG. 13)

Example 16.9—Biofilm Development

Biofilm development is highly significant in medical clinic, as it causes difficulties in several disorder treatment, including cryptococcosis. Due to that, it was proposed assessing AcM effect in biofilm development by XTT trial.

AcMs were tested (25 µg/ml) against three fungus species (*C. albicans*, *C. neoformans*—H99—and acapsular mutant of *C. neoformans*—Cap67), with control by AcM anti-GXM 18B7 (25 µg/ml) only to H99. In the first assay (FIGS. 14A and B), cellular suspensions were washed to remove non-adhering cells to substrate. AcMs inhibited significantly biofilm development compared to non-treated cells adhered directly to substrate (p<0.05). In second assay (FIGS. 14C and D), cellular suspensions were not washed, and again AcM inhibited biofilm development (p<0.05) compared to cell not treated with antibodies. In both assays, cell growth was observed.

AcMs were compared to AcM anti-GXM 18B7 concerning biofilm development inhibition. For cell suspensions washed and not washed, AcMs were capable of inhibiting significantly cell H99 biofilm development compared to non-treated cell effect, and it presents a similar behavior to AcM anti-GXM 18B7 (p<0.05) (FIG. 15).

It was evidenced that treatments with AcM impact biofilm development (p<0.05) compared to non-treated fungus, and has similar behavior to AmB. Every treatment tested impacted only biofilm development, as there was cellular growth.

Example 16.10—ELISA Against Several Cells Using PL

In this assay, the same principle was used to fungus labeling by ELISA using PL, however it was performed against different cellular types to evidence that AcMs are specific against chitin, and consequently against fungus. For that, a human lung cell line was used, A549, *Giardia lamblia* and negative gram and positive gram bacteria. Graph provides that, in every cellular density, AcMs were not capable of identifying specific target, on the other hand, it presented the same result to identify target in *C. neoformans*, that shows that AcMs are specific targets and keeps its sensibility in $10^6$ cells/ml, as provided by FIG. 16. The experiment was performed 3 times, which kept their reproducibility.

Example 16.11—Minimum Inhibiting Concentration Assay

AcMs fungicide activity was tested through CIM test. No AcMs presented fungicide effect, unlike controls with 1 µg/ml of AmB and 8 µg/ml of FLC (FIGS. 18 and 19). It was assessed if AcMs association with AmB or FLC would trigger antifungal effects in sub-inhibiting concentrations, thus 1 µg/ml concentrations of AmB and 4 and 2 µg/ml to FLC in combination with AcMs different concentrations. To assess whether there was combining effect of AcMs with drug, it was used as drug action base in isolate form.

As AcMs fungicide action was assessed in combination with AmB, it was observed that 6.2 µg/ml concentration of both antibodies triggered AmB fungicide action in sub-inhibiting concentration, compared to drug isolate action in its optimal action concentration (p<0.001). However, there was fungicide effect potentialization of AmB 0.1 µg/ml combined to antibody HC6/DD11 as from 1.6 µg/ml (p<0.01) concentration, and to antibody AF1/CC5, the combining effect presented fungicide effect as from 3.2 µg/ml (p<0.01) concentration, compared to isolate AmB sub-inhibiting concentration (FIG. 18).

Concerning AcMs combining effect, FLC, antibody partial fungicide effect was observed (3.2 µg/ml to both AcM) in combination with FLC (4 µg/ml) (p<0.01). Thus, there was drug action potentialization compared to isolate form at 4 µg/ml concentration. What is more, AcMs combining fungicide action was observed with FLC at 2 µg/ml concentration, as drug action was triggered, reaching levels in isolate form at 4 µg/ml concentration.

Example 16.12—Survival Trial

Mice were lethally challenged with inoculant i.p. of $1 \times 10^5$ cells of yeast *C. neoformans* strain H99. After 2 hours, they were treated with PBS (negative control), 85 µg/animal of AcM (HC6/DD11) in isolate form, 0.25 or 2.5 mg/kg of AmB in isolate form, and in synergic form, AcM keeping test concentrations. Treatments were repeated for another two times, with 10-day interval.

Animals infected with *C. neoformans* and treated with PBS died on the 28th day after the infection, and the ones treated with AcM died until the 29th day, animal group treated only with AmB at 0.25 mg/kg died on the 37th day, and synergic group (AcM—85 µg/animal—with AmB—0.25 mg/kg-) did not die. Control group treated with AmB standard dose (2.5 mg/kg) did not die as expected (data not provided). Thus, 100% survival was achieved for animals infected with *C. neoformans* and treated with AcM HC6/DD11 and sub-inhibiting AmB.

Synergic group was significantly statistical in relation to the group treated with PBS and AcM (p≤0.001). The same was observed in relation to the group treated with AmB (0.25 mg/kg) (p=0.01). Surviving animals of group treated with mAb and AmB did not have symptoms by the end of the experiment (90 days) (FIG. 20).

Example 16.13—Comparative Modeling

With the purpose of humanizing murine AcM, light and heavy chains of AcM HC6/DD11 and AF1/CC5 were aligned against human antibody database of IMGT (http://imgt(dot)org/3Dstructure-DB/cgi/DomainGapAlign(dot) cgi). Sequences that presented greater homology to heavy and light chain HC6/DD11 were, respectively IGHV3-11*01 and IGKV1-16*01, and to AF1/CC5, respectively, IGHV3-73*01 and IGKV1-17*03. Amino acids that differed between murine and human sequences were replaced by amino acids present in human antibody framework.

To achieve murine and humanized HC6/DD11 and AF1/CC5 antibody three-dimension structures, molecular modeling methodology was used. Local alignment was performed through BLASTp (Basic Local Alignment Search Tool) against PDB database to choose and select mold proteins. Sequence 4UOR was used as template to murine AcM HC6/DD11, and to murine AF1/CC5, the following heavy and light chain sequences, respectively, 5IJK 3NFT. Concerning HC6/DD11 humanized, sequence 5F72 was used, and to AF1/CC5 humanized heavy and light chain, 6MAM and 3NFP, respectively.

Three-dimension template development was performed using Modeller 9.19 program. Murine and humanized templates were submitted to energy minimization using Wincoot program and aligned between themselves to check foreseen structures (FIG. 21).

REFERENCES

1. Kö Hler J R, Casadevall A, Perfect J. The Spectrum of Fungi That Infects Humans. [cited 2018 Dec. 6]; Available from: www.perspectivesinmedicine.org.
2. Heitman J. Microbial Pathogens in the Fungal Kingdom. 2011 [cited 2018 Dec. 6]; Available from: https://www.ncbi.nlm.nih.gov/pmc/articles/PMC3081590/pdf/nihms-264974.pdf.
3. Armstrong-James D, Meintjes G, Brown G D. A neglected epidemic: fungal infections in HIV/AIDS. 2014 [cited 2018 Aug. 15]; Available from: http://dx.doi.org/10.1016/j.tim.2014.01.001.
4. Bongomin F, Gago S, Oladele R, Denning D. Global and Multi-National Prevalence of Fungal Diseases—Estimate Precision. J Fungi [Internet]. 2017; 3(4):57. Available from: http://www.mdpi.com/2309-608X/3/4/57.
5. Brown G D, Denning D W, Gow N A R, Levitz S M, Netea M G, White T C. Hidden killers: Human fungal infections. Sci Transl Med. 2012; 4(165).
6. Vallabhaneni S, Mody R K, Walker T, Chiller T. The Global Burden of Fungal Diseases. 2016 [cited 2018 Aug. 22]; Available from: http://dx.doi.org/10.1016/j.idc.2015.10.004.
7. Benedict K, Richardson M, Vallabhaneni S, Jackson B R, Chiller T. Fungal infections 7 Emerging issues, challenges, and changing epidemiology of fungal disease outbreaks. Ser Lancet Infect Dis [Internet]. 2017 [cited 2018 Aug. 17]; 17:403-15. Available from: http://dx-.doi.org/10.1016/.
8. Nucci M, Marr K a. Emerging fungal diseases. Clin Infect Dis. 2005; 41(4):521-6.
9. Harris J R, Lockhart S R, Sondermeyer G, Vugia D J, Crist M B, Tobin D'angelo M, et al. *Cryptococcus gattii* Infections in Multiple States Outside the US Pacific Northwest. 2013 [cited 2018 Aug. 22]; 19(10). Available from: http://dx.doi.org/10.3201/eid1910.130441.
10. Harris J R, Lockhart S R, Debess E, Marsden-Haug N, Goldoft M, Wohrle R, et al. *Cryptococcus gattii* in the United States: Clinical Aspects of Infection With an Emerging Pathogen. [cited 2018 Aug. 22]; Available from: https://academic.oup.com/cid/article-abstract/53/12/1188/400737.

11. Polvi E J, Li X, O'meara T R, Leach M D, Cowen L E. Opportunistic yeast pathogens: reservoirs, virulence mechanisms, and therapeutic strategies. [cited 2018 Aug. 16]; Available from: https://link.springer.com/content/pdf/10.1007%2Fs00018-015-1860-z.pdf.

12. Leach M D, Cowen L E. Surviving the Heat of the Moment: A Fungal Pathogens Perspective [Internet]. [cited 2018 Aug. 21]. Available from: http://www.wellcome.ac.uk/Funding/.

13. Bain J M, Lewis L E, Okai B, Quinn J, Gow N A R, Erwig L-P. Non-lytic expulsion/exocytosis of Candida albicans from macrophages. Fungal Genet Biol [Internet]. 2012 [cited 2018 Aug. 21]; 49:677-8. Available from: https://www.ncbi.nlm.nih.gov/pmc/articles/PMC3430864/pdf/main.pdf.

14. Moraes Nicola A, Robertson E J, Albuquerque P, da Silveira Derengowski L, Casadevall A. Nonlytic Exocytosis of Cryptococcus neoformans from Macrophages Occurs In Vivo and Is Influenced by Phagosomal pH. 2011 [cited 2018 Aug. 21]; Available from: https://www.ncbi.nlm.nih.gov/pmc/articles/PMC3150755/pdf/mBio.00167-11.pdf.

15. Coelho C, Bocca A L, Casadevall A. The Tools for Virulence of Cryptococcus neoformans. Adv Appl Microbiol [Internet]. 2014 Jan. 1 [cited 2018 Aug. 21]; 87:1-41. Available from: https://www.sciencedirect.com/science/article/pii/B9780128002612000013?via%3Dihub.

16. Rajasingham R, Smith R M, Park B J, Jarvis J N, Govender N P, Chiller T M, et al. Global burden of disease of HIV-associated cryptococcal meningitis: an updated analysis. [cited 2018 Aug. 21]; Available from: https://www.ncbi.nlm.nih.gov/pmc/articles/PMC5818156/pdf/nihms886671.pdf.

17. Giacomazzi J, Baethgen L, Carneiro L C, Millington M A, Denning D W, Colombo A L, et al. The burden of serious human fungal infections in Brazil. Mycoses. 2016; 59(3):145-50.

18. Roemer T, Krysan DJ. Antifungal Drug Development: Challenges, Unmet Clinical Needs, and New Approaches. 2016.

19. Kontoyiannis D P. Antifungal Resistance: An Emerging Reality and A Global Challenge. Glob Chall Antifung Resist•JID [Internet]. 2017 [cited 2018 Sep. 18]; 2017: 216. Available from: https://academic.oup.com/jid/article-abstract/216/suppl_3/S431/4107053.

20. Spivak E S, Hanson K E. Candida auris: an Emerging Fungal Pathogen. Kraft C S, editor. J Clin Microbiol. 2017 November; 56(2):e01588-17.

21. Ostermann H, Solano C, Jarque I, Garcia-Vidal C, Gao X, Barrueta J A, et al. Cost analysis of voriconazole versus liposomal amphotericin B for primary therapy of invasive aspergillosis among patients with haematological disorders in Germany and Spain [Internet]. Vol. 15. 2014 [cited 2018 Aug. 21]. Available from: http://www.biomedcentral.com/2050-6511/15/52.

22. Lin X. Cryptococcus neoformans: Morphogenesis, infection, and evolution. Infect Genet Evol. 2009; 9(4): 401-16.

23. Kwon-Chung K J, Bennett J E, Wickes B L, Meyer W, Cuomo C A, Wollenburg K R, et al. The Case for Adopting the " Species Complex" Nomenclature for the Etiologic Agents of Cryptococcosis. 2017 [cited 2018 Dec. 11]; Available from: https://doi.org/10.1128/mSphere.00357-16.

24. Hagen F, Khayhan K, Theelen B, Kolecka A, Polacheck I, Sionov E, et al. Recognition of seven species in the Cryptococcus gattii/Cryptococcus neoformans species complex. Fungal Genet Biol [Internet]. 2015 May [cited 2019 Aug. 20]; 78:16-48. Available from: https://linkinghub.elsevier.com/retrieve/pii/S1087184515000328.

25. Kwon-Chung K J, Fraser J A, Doering T L, Wang Z, Janbon G, Idnurm A, et al. Cryptococcus neoformans and Cryptococcus gattii, the Etiologic Agents of Cryptococcosis [Internet]. [cited 2018 Dec. 11]. Available from: www.perspectivesinmedicine.org.

26. Chayakulkeeree M. Cryptococcosis. 2006; 20:507-44.

27. Colombo A N A C, Rodrigues M L. Fungal colonization of the brain: anatomopathological aspects of neurological cryptococcosis epidemic in HIV patients (Armstrong-James et al. people die each year because of systemic fungal cryptococcosis presented in the last (9 th) edition and Cryp. 2015; 87:1293-309.

28. Lin X, Heitman J. The Biology of the Cryptococcus neoformans Species Complex. Annu Rev Microbiol [Internet]. 2006; 60(1):69-105. Available from: http://www.annualreviews.org/doi/10.1146/annurev.micro.60.080805.142102.

29. Casadevall A, Pirofski L-A. MINIREVIEWS Accidental Virulence, Cryptic Pathogenesis, Martians, Lost Hosts, and the Pathogenicity of Environmental Microbes. Eukaryot Cell [Internet]. 2007 [cited 2018 Dec. 11]; 6(12):2169-74. Available from: https://www.ncbi.nlm-.nih.gov/pmc/articles/PMC2168257/pdf/0308-07.pdf.

30. Dutra F F, Albuquerque P C, Rodrigues M L, Fonseca F L. Warfare and defense: The host response to Cryptococcus infection. Fungal Biol Rev [Internet]. 2018; 32(2): 35-51. Available from: https://doi.org/10.1016/j.fbr.2017.09.002.

31. Templeton S, Pirofski L-A, Johnston S A, Wormley F L, Williamson P R, Elsegeiny W, et al. immunology of Cryptococcal infections: Developing a Rational Approach to Patient Therapy. 2018 [cited 2018 Aug. 10]; 9:651. Available from: www.frontiersin.org.

32. Olszewski M A, Wormley F L, Williamson Sarah E Hardison P R, Malachowski A N, Davis J J, Vedula P, et al. Polarization Response by Promoting Macrophage M2 during the Afferent Phase of the Immune Cryptococcus neoformans Expansion of Homolog Ssa1 Contributes to Pulmonary Cryptococcal Heat Shock Protein 70. J Immunol Ref [Internet]. 2015 [cited 2019 Feb. 6]; 194:5999-6010. Available from: http://www.jimmunol.org/content/194/12/5999http://www.jimmunol.org/content/194/12/5999.full#ref-list-1.

33. Campuzano A, Wormley F L. Innate Immunity against Cryptococcus, from Recognition to Elimination. [cited 2018 Aug. 10]; Available from: www.mdpi.com/journal/jof.

34. Olszewski M A, Wormley F L, Chrissy Leopold Wager J M, Hole C R. Mice Infection in Cryptococcus neoformans against STAT1 Signaling Is Essential for Protection. J Immunol Ref [Internet]. 2014 [cited 2019 Aug. 20]; 193:4060-71. Available from: http://www.jimmunol.org/content/193/8/4060http://www.jimmunol.org/content/193/8/4060.full#ref-list-1.

35. Leopold Wager C M, Hole C R, Wozniak K L, Wormley F L, Jr. Cryptococcus and Phagocytes: Complex Interactions that Influence Disease Outcome. Front Microbiol [Internet]. 2016 [cited 2018 Aug. 10]; 7:105. Available from: http://www.ncbi.nlm.nih.gov/pubmed/26903984.

36. Liu T-B, Perlin D S, Xue C. Molecular mechanisms of cryptococcal meningitis. 2012 [cited 2019 Feb. 6]; Available from: https://www.tandfonline.com/action/journalInformation?journalCode=kvir20.

37. Kozel T R, Wickes B. Fungal Diagnostics. [cited 2018 Aug. 24]; Available from: www.perspectivesinmedicine.org.

38. Theel E S, Doern C D. D-Glucan Testing Is Important for Diagnosis of Invasive Fungal Infections. 2013 [cited 2018 Aug. 27]; Available from: https://www.ncbi.nlm.nih.gov/pmc/articles/PMC3889722/pdf/zjm3478.pdf.

39. Schwartz S, Kontoyiannis D P, Harrison T, Ruhnke M. Advances in the diagnosis and treatment of fungal infections of the CNS. Lancet Neurol [Internet]. 2018; 17(4): 362-72. Available from: http://dx.doi.org/10.1016/S1474-4422(18)30030-9.

40. Meya D B, Manabe Y C, Castelnuovo B, Cook B A, Ali M, Kambugu A, et al. Serum Cryptococcal Antigen (CRAG) Screening is a Cost-Effective Method to Prevent Death in HIV-infected persons with CD4 ≤100/μL starting HIV therapy in Resource-Limited Settings. Clin Infect Dis. 2010; 51(4):448-55.

41. Barnes P D, Marr K A. Aspergillosis: Spectrum of Disease, Diagnosis, and Treatment. [cited 2018 Aug. 24]; Available from: https://ac.els-cdn.com/S0891552006000511/1-s2.0-S0891552006000511-main.pdf?_tid=507238c0-e399-4d35-a636-9d578d958447&acdnat=1535138005_2968e5 6d5f508d2a5e02c85f2d1d7496.

42. Ramanan P, Wengenack N L, Theel E S. Laboratory Diagnostics for Fungal Infections: A Review of Current and Future Diagnostic Assays. Clin Chest Med [Internet]. 2017; 38(3):535-54. Available from: http://dx.doi.org/10.1016/j.ccm.2017.04.013.

43. Powers-Fletcher M V, Hanson K E. Nonculture Diagnostics in Fungal Disease. Infect Dis Clin NA [Internet]. 2016 [cited 2018 Aug. 27]; 30:37-49. Available from: http://dx.doi.org/10.1016/j.idc.2015.10.005.

45. Lamoth F. Galactomannan and 1,3-ß-d-Glucan Testing for the Diagnosis of Invasive Aspergillosis. J Fungi [Internet]. 2016; 2(3):22. Available from: http://www.mdpi.com/2309-608X/2/3/22.

46. Jaijakul S, Vazquez J A, Swanson R N, Ostrosky-Zeichner L. 3)-β-D-Glucan as a Prognostic Marker of Treatment Response in Invasive Candidiasis. [cited 2019 Aug. 20].

47. Nguyen H, Wissel M C, Shields R K, Salomoni M A, Hao B, Press E G, et al. Performance of Candida Real-time Polymerase Chain Reaction, b-D-Glucan Assay, and Blood Cultures in the Diagnosis of Invasive Candidiasis. [cited 2018 Aug. 28]; Available from: https://academic.oup.com/cid/article-abstract/54/9/1240/391720.

48. Onishi A, Sugiyama D, Kogata Y, Saegusa J, Sugimoto T, Kawano S, et al. Diagnostic Accuracy of Serum 1,3-D-Glucan for Pneumocystis jiroveci Pneumonia, Invasive Candidiasis, and Invasive Aspergillosis: Systematic Review and Meta-Analysis Downloaded from. 2011 [cited 2018 Aug. 28]; Available from: http://jcm.asm.org/.

49. Sulahian A, Porcher R, Bergeron A, Touratier S, Raffoux E, Menotti J, et al. Use and limits of (1-3)-β-D-glucan assay (fungitell), compared to galactomannan determination (platelia Aspergillus), for diagnosis of invasive aspergillosis. J Clin Microbiol. 2014.

50. Azab M M, Taleb A F A, Mohamed N A E, Omran F H. Rapid Diagnosis of Invasive Fungal Infections [Internet]. Vol. 4, Int.J.Curr.Microbiol.App.Sci. 2015 [cited 2018 Aug. 29]. Available from: http://www.ijcmas.com.

51. Singh N, Paterson D L. Aspergillus Infections in Transplant Recipients. Clin Microbiol Rev [Internet]. 2005 [cited 2018 Aug. 29]; 18(1):44-69. Available from: https://www.ncbi.nlm.nih.gov/pmc/articles/PMC54 4171/pdf/0014-04.pdf.

52. Fisher C E, Stevens A M, Leisenring W, Pergam S A, Boeckh M, Hohl T M. Independent contribution of bronchoalveolar lavage and serum galactomannan in the diagnosis of invasive pulmonary aspergillosis.

53. Rampini S K, Zbinden A, Speck R F, Bloemberg G V. Similar efficacy of broad-range ITS PCR and conventional fungal culture for diagnosing fungal infections in non-immunocompromised patients. 2016 [cited 2018 Aug. 29]; Available from: https://bmcmicrobiol.biomedcentral.com/track/pdf/10.1186/s12866-016-0752-1.

54. Zeller I, Schabereiter-Gurtner C, Mihalits V, Selitsch B, Barousch W, Hirschl A M, et al. Detection of fungal pathogens by a new broad range real-time PCR assay targeting the fungal ITS2 region. 2018 [cited 2018 Sep. 18]; Available from: www.ebi.ac.uk/clustalw/.

55. Buitrago M J, Aguado J M, Ballen A, Bernal-Martinez L, Prieto M, Garcia-Reyne A, et al. Efficacy of DNA amplification in tissue biopsy samples to improve the detection of invasive fungal disease. Clin Microbiol Infect [Internet]. 2013 [cited 2019 Aug. 21]; 19:E271-7. Available from: http://www.ncbi.nlm.nih.gov/Genbank/.

56. Rodrigues M L, Carlos Chagas I, Oswaldo Cruz F. The Multifunctional Fungal Ergosterol. 2018 [cited 2018 Sep. 18]; Available from: https://doi.org/10.1128/mBio.01755-18.

57. Pelleschi Taborda C, Frases S, Rao Juvvadi P, Fusco-Almeida A M, Scorzoni L, A de Paula Silva A C, et al. Antifungal Therapy: New Advances in the Understanding and Treatment of Mycosis. 2017 [cited 2018 Aug. 23]; Available from: www.frontiersin.org.

58. Vandeputte P, Ferrari S, Coste A T. Antifungal Resistance and New Strategies to Control Fungal Infections Antifungal Resistance and New Strategies to Control Fungal Infections. 2014; (June).

59. Edith Albengres, Hervé Le Louët J-PT, Tillement J-P. Systemic Antifungal Agents. Drug Saf [Internet]. 1998 [cited 2019 Aug. 22]; 18(2):83-97. Available from: http://link.springer.com/10.2165/00002018-199818020-00001.

60. Denning D W, Venkateswarlu K, Oakley K L, Anderson M J, Manning N J, Stevens D A, et al. Itraconazole Resistance in Aspergillus fumigatus [Internet]. Vol. 41. 1997 [cited 2019 Aug. 22]. Available from: https://www.ncbi.nlm.nih.gov/pmc/article s/PMC163916/pdf/411364.pdf.

61. Lemke F Kiderlen O Kayser Amphotericin B AA. MINI-REVIEW. Appl Microbiol Biotechnol [Internet]. 2005 [cited 2018 Sep. 25]; 68:151-62. Available from: https://link.springer.com/content/pdf/10.1007%2Fs00253-005-1955-9.pdf.

62. Spitzer M, Robbins N, Wright G D. Combinatorial strategies for combating invasive fungal infections. 2017 [cited 2019 Feb. 26]; Available from: http://dx.doi.org/10.1080/21505594.2016.1196300.

63. Zotchev S. Polyene Macrolide Antibiotics and their Applications in Human Therapy. Curr Med Chem. 2012; 10(3):211-23.

64. Alvarez C, Andes D R, Kang J Y, Krug C, Kwon G S. Antifungal Efficacy of an Intravenous Formulation Containing Monomeric Amphotericin B, 5-Fluorocytosine, and Saline for Sodium Supplementation HHS Public Access. Pharm Res [Internet]. 2017 [cited 2018 Sep. 25]; 34(5): 1115-24. Available from: https://www.ncbi.nlm.nih.gov/pmc/articles/PMC5383515/pdf/nihms8 53112.pdf.

65. Steimbach L M, Tonin F S, Virtuoso S, Borba H H L, Sanches ACC, Wiens A, et al. Efficacy and safety of amphotericin B lipid-based formulations—A systematic review and meta-analysis. Mycoses. 2017; 60(3): 146-54.

66. Borba H H L, Steimbach L M, Riveros B S, Tonin F S, Ferreira V L, Bagatim B A de Q, et al. Cost-effectiveness of amphotericin B formulations in the treatment of systemic fungal infections. Mycoses. 2018; 61(10):754-63.

67. Hamill R J. Amphotericin B Formulations: A Comparative Review of Efficacy and Toxicity. Drugs [Internet]. 2013 Jun. 1 [cited 2019 Aug. 22]; 73(9):919-34. Available from: http://link.springer.com/10.1007/s40265-013-0069-4.

68. Thorn C F, Marsh S, Carrillo M W, Mcleod H L, Klein T E, Altman R B. PharmGKB summary: fluoropyrimidine pathways. 2011 [cited 2019 Aug. 22]; Available from: http://www.pharmgkb.org/search/annotatedGene/mthfr/index.jsp.

69. Mukherjee P K, Sheehan D J, Hitchcock C A, Ghannoum M A. Combination Treatment of Invasive Fungal Infections. Clin Microbiol Rev [Internet]. 2005 [cited 2019 Aug. 22]; 18(1): 163-94. Available from: https://www.ncbi.nlm.nih.gov/pmc/articles/PMC544182/pdf/0092-03.pdf.

70. Fesel P H, Zuccaro A. β-glucan: Crucial component of the fungal cell wall and elusive MAMP in plants. Fungal Genet Biol [Internet]. 2016 May [cited 2019 Aug. 22]; 90:53-60. Available from: https://linkinghub.elsevier.com/retrieve/pii/S1087184515300529.

71. Odds F C, Brown A J P, Gow N A R. Antifungal agents: mechanisms of action. Trends Microbiol [Internet]. 2003 June [cited 2019 Aug. 22]; 11(6):272-9. Available from: https://linkinghub.elsevier.com/retrieve/pii/S0966842X03001173.

72. Kurtz M B, Douglas C M. Lipopeptide inhibitors of fungal glucan synthase [Internet]. Vol. 35, Journal of Medical & Veterinary Mycology. 1997 [cited 2019 Aug. 22]. Available from: https://academic.oup.com/mmy/article-abstract/35/2/79/940389.

73. Abbas A K, Lichtman A H, Pillai S. Imunologia Celular e Molecular. 8th ed. Digital T, editor. Rio de: Elsevier Inc.; 2015. 549 p.

74. Köhler G, Milstein C. Pillars Article: Continuous cultures of fused cells secreting antibody of predefined specificity. Nature, 1975, 256 (5517): 495-497. J Immunol. 2005; 174(5517):2453-5.

75. Dos Santos M L, Quintilio W, Manieri T M, Tsuruta L R, Moro AM. Advances and challenges in therapeutic monoclonal antibodies drug development. Brazilian J Pharm Sci. 2018; 54(Special Issue): 1-15.

76. Kaplon H, Reichert J M. Antibodies to watch in 2019. MAbs [Internet]. 2019; 11(2):219-38. Available from: https://doi.org/10.1080/19420862.2018. 1556465.

77. Casadevall A, Pirofski L-A. IMMUNOGLOBULINS IN DEFENSE, PATHOGENESIS AND THERAPY OF FUNGAL DISEASES. 2012 [cited 2018 Nov. 16]; Available from: https://www.ncbi.nlm.nih. gov/pmc/articles/PMC3360875/pdf/nihms375082.pdf.

78. Nosanchuk J D, Steenbergen J N, Shi L, Deepe G S, Casadevall A, Casadevall A. Antibodies to a cell surface histone-like protein protect against *Histoplasma capsulatum*. J Clin Invest [Internet]. 2003 October [cited 2018 Nov. 8]; 112(8):1164-75. Available from: http://www.ncbi.nlm.nih.gov/pubmed/14561701.

79. Rachini A, Pietrella D, Lupo P, Torosantucci A, Chiani P, Bromuro C, et al. An Anti-Glucan Monoclonal Antibody Inhibits Growth and Capsule Formation of *Crypto-*

42

*coccus neoforman s*In Vitro and Exerts Therapeutic, Anticryptococcal Activity In Vivo. Infect Immun [Internet]. 2007 [cited 2018 Jul. 5]; 75(11):5085-94. Available from: http://iai.asm.org/.

80. Rodrigues M L, Shi L, Barreto-Bergter E, Nimrichter L, Farias S E, Rodrigues E G, et al. Monoclonal antibody to fungal glucosylceramide protects mice against lethal *Cryptococcus neoformans* infection. Clin Vaccine Immunol. 2007; 14(10):1372-6.

81. Guimarães A J, de Cerqueira M D, Nosanchuk J D. Surface architecture of *Histoplasma capsulatum*. Front Microbiol. 2011; 2(November):1-14.

82. Guimarães A J, Frases S, Gomez F J, Zancopé-Oliveira R M, Nosanchuk J D. Monoclonal Antibodies to Heat Shock Protein 60 Alter the Pathogenesis of *Histoplasma capsulatum* †. Infect Immun [Internet]. 2009 [cited 2018 Sep. 20]; 77(4): 1357-67. Available from: https://www.ncbi.nlm.nih.gov/pmc/articles/PMC2663142/pdf/1443-08.pdf.

83. Kauffman C A. Histoplasmosis: a Clinical and Laboratory Update. Clin Microbiol Rev [Internet]. 2007 [cited 2018 Nov. 5]; 20(1):115-32. Available from: http://cmr.asm.org/.

84. Huang H-R, Fan L-C, Rajbanshi B, Xu J-F. Evaluation of a New Cryptococcal Antigen Lateral Flow Immunoassay in Serum, Cerebrospinal Fluid and Urine for the Diagnosis of Cryptococcosis: A Meta-Analysis and Systematic Review. 2015 [cited 2018 Aug. 27]; Available from: http://journals.plos.org/plosone/article/file?id=10.1371/journal.pone.0127117 &type=printable.

85. Rivera J, Zaragoza O, Casadevall A. Antibody-Mediated Protection against *Cryptococcus neoformans* Pulmonary Infection Is Dependent on B Cells. Infect Immun [Internet]. 2005 [cited 2018 Jan. 18]; 73(2):1141-50. Available from: https://www.ncbi.nlm.nih.gov/pmc/articles/PMC546959/pdf/0809-04.pdf.

86. Posch W, Steger M, Wilflingseder D, Lass-Flörl C. Promising immunotherapy against fungal diseases. Expert Opin Biol Ther [Internet]. 2017 [cited 2018 Aug. 23]; 17(7):861-70. Available from: http://www.tandfonline.com/action/journalInformation?journalCode=iebt20.

87. Martinez L R, Casadevall A. Specific Antibody Can Prevent Fungal Biofilm Formation and This Effect Correlates with Protective Efficacy. Infect Immun [Internet]. 2005 [cited 2019 Feb. 27]; 73(10):6350-62. Available from: https://www.ncbi.nlm.nih.gov/pmc/articles/PMC1230912/pdf/0374-05.pdf.

88. Martinez L R, Moussai D, Casadevall A. Antibody to *Cryptococcus neoformans* Glucuronoxylomannan Inhibits the Release of Capsular Antigen. Infect Immun. 2004; 72(6):3674-9.

89. Moragues M D, Omaetxebarria M J, Elguezabal N, Sevilla M J, Conti S, Polonelli L, et al. A Monoclonal Antibody Directed against a *Candida albicans* Cell Wall Mannoprotein Exerts Three Anti-*C. albicans* Activities. Infect Immun. 2003; 71(9):5273-9.

90. Casadevall A, Pirofski L-A. A new synthesis for antibody-mediated immunity NIH Public Access. Nat Immunol [Internet]. 2012 [cited 2019 Aug. 22]; 13(1):21-8. Available from: http://www.nature.com/reprints/index.html.

91. Torosantucci A, Chiani P, Bromuro C, De Bernardis F, Palma A S, Liu Y, et al. Protection by Anti-b-Glucan Antibodies Is Associated with Restricted b-1,3 Glucan Binding Specificity and Inhibition of Fungal Growth and Adherence. [cited 2019 Feb. 26]; Available from: www.plosone.org.

92. Brena S, Omaetxebarria M J, Elguezabal N, Cabezas J, Moragues M D, Pontón J. Fungicidal Monoclonal Antibody C7 Binds to *Candida albicans* Als3. Infect Immun [Internet]. 2007 [cited 2019 Aug. 23]; 75(7):3680-2. Available from: https://www.ncbi.nlm.nih.gov/pmc/articles/PMC193295 6/pdf/1840-06.pdf.

93. Guimarães A J, Frases S, Gomez F J, Zancopé-Oliveira R M, Nosanchuk J D. Monoclonal Antibodies to Heat Shock Protein 60 Alter the Pathogenesis of *Histoplasma capsulatum* †. Infect Immun [Internet]. 2009 [cited 2018 November 7]; 77(4): 1357-67. Available from: https://www.ncbi.nlm.nih.gov/pmc/articles/PMC2663142/pdf/1443-08.pdf.

94. Beenhouwer D O, Yoo E M, Lai C-W, Rocha M A, Morrison S L. Human Immunoglobulin G2 (IgG2) and IgG4, but Not IgG1 or IgG3, Protect Mice against *Cryptococcus neoformans* Infection. Infect Immun [Internet]. 2007 [cited 2019 Aug. 23]; 75(3):1424-35. Available from: https://www.ncbi.nlm.nih.gov/pmc/articles/PMC1828574/pdf/1161-06.pdf.

95. Buissa-Filho R, Puccia R, Marques A F, Pinto F A, Muñoz J E, Nosanchuk J D, et al. The monoclonal antibody against the major diagnostic antigen of *Paracoccidioides brasiliensis* mediates immune protection in infected BALB/c mice challenged intratracheally with the fungus. Infect Immun. 2008; 76(7):3321-8.

96. Smulian A G, Sullivan D W, Theus S A. Immunization with recombinant *Pneumocystis carinii* p55 antigen provides partial protection against infection: characterization of epitope recognition associated with immunization [Internet]. Vol. 2, Microbes and Infection. 2000 [cited 2019 Aug. 23]. Available from: https://pdf.sciencedirect assets.com.

97. Saeed A F U H, Ling S, Yuan J, Wang S. The Preparation and Identification of a Monoclonal Antibody against Domoic Acid and Establishment of Detection by Indirect Competitive ELISA. 2017 [cited 2019 Feb. 7]; Available from: www.mdpi.com/journal/toxins.

98. Goding, Anoclodies Monoclonal: Principies and Practice, pp. 59-103). (Academic Press, 1986).

99. Erwig L P, R Gow N A. Interactions of fungal pathogens with phagocytes. Nat Rev Microbiol. 2016 March; 14(3): 163-76. doi: 10.1038/nrmicro.2015.21.

100. Katzung B, Masters S, Trevor A. Farmacologia básica e clínica. 12° edição Porto Alegre. AMGH, 2014.

101. Ward, E. S. et al., Nature 341, 544-546 (1989)).

102. Bird et al., Science, 242, 423-426, 1988.

103. Huston et al., PNAS USA, 85, 5879-5883, 1988).

104. Power e Hudson, J Immunol. Methods 242: 193-204 9 (2000)).

105. Holliger et al. Proc. Natl. Acad. Sci. USA 90 6444-6448, (1993).

106. Hoogenboom et al. Trends Biotechnol, 15:62-70 (1997).

107. Hoogenboom, et al. Immunotechnology 4:1-20 (1998).

108. McGregor et al. Mol. Biotechnol, 6:155-62 (1996).

109. Bird et al., Science, 242:423-426 (1988).

110. King "Applications and Engineering of Monoclonal Antibodies" Taylor & Francis, 1998.

The invention claimed is:

1. An isolated monoclonal antibody that specifically binds to a fungal chitooligomer, comprising:
   (i) a heavy chain variable region comprising a CDR1 sequence as set forth in SEO ID NO: 1, a CDR2 sequence as set forth in SEQ ID NO: 2, and a CDR3 sequence as set forth in SEQ ID NO: 3; and
   (ii) a light chain variable region comprising a CDR1 sequence as set forth in SEQ ID NO: 4, a CDR2 sequence as set forth in SEQ ID NO: 5, and a CDR3 sequence as set forth in SEQ ID NO: 6;

or
   (i) a heavy chain variable region comprising a CDR1 sequence as set forth in SEQ ID NO: 7, a CDR2 sequence as set forth in SEQ ID NO: 8, and a CDR3 sequence as set forth in SEQ ID NO: 9; and
   (ii) a light chain variable region comprising a CDR1 sequence as set forth in SEQ ID NO: 10, a CDR2 sequence as set forth in SEQ ID NO: 11, and a CDR3 sequence as set forth in SEQ ID NO: 12.

2. The antibody according to claim 1, wherein the antibody is selected from the group consisting of a murine antibody, humanized antibody, a human antibody, and a chimeric antibody.

3. A pharmaceutical composition, comprising the antibody of claim 1 and a pharmaceutically acceptable carrier, and optionally an excipient.

4. The pharmaceutical composition according to claim 3, further comprising polyenes and/or azoles.

5. The pharmaceutical composition according to claim 4, further comprising AmB and/or FLC.

6. A method for diagnosing a fungal infection, comprising:

(i) providing the antibody of claim 1 with a sample obtained from a patient, (ii) contacting said antibody with a biological sample to be tested under conditions and duration sufficient to develop an antigenic/antibody complex; and (iii) detecting said antigenic/antibody complex using a detection technique capable of generating detectable signal corresponding to said antigenic/antibody complex.

7. The method according to claim 6, wherein said biological sample is selected from the group consisting of saliva, urine, serum, blood, bronchoalveolar lavage, peritoneal fluid or liquid, and any other biological fluids of a patient.

8. A fungal infection diagnostic kit, comprising the antibody of claim 1.

9. The diagnostic kit according to claim 8, further comprising instructions for usage.

10. The diagnostic kit according to claim 8, further comprising a detection medium configured to generate a detectable signal corresponding to an antigen-antibody complex.

* * * * *

SEQUENCE LISTING

```
<160> NUMBER OF SEQ ID NOS: 20

<210> SEQ ID NO 1
<211> LENGTH: 10
<212> TYPE: PRT
<213> ORGANISM: Mus musculus

<400> SEQUENCE: 1

Gly Phe Thr Phe Ser Asp Tyr Gly Met Ala
1               5                   10

<210> SEQ ID NO 2
<211> LENGTH: 9
<212> TYPE: PRT
<213> ORGANISM: Mus musculus

<400> SEQUENCE: 2

Ile Ser Asn Leu Ala Tyr Ser Ile Tyr
1               5

<210> SEQ ID NO 3
<211> LENGTH: 12
<212> TYPE: PRT
<213> ORGANISM: Mus musculus

<400> SEQUENCE: 3

Asp Tyr Tyr Gly Ser Ser Tyr Trp Tyr Phe Asp Val
1               5                   10

<210> SEQ ID NO 4
<211> LENGTH: 10
<212> TYPE: PRT
<213> ORGANISM: Mus musculus
```

-continued

```
<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Mus musculus

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Arg Ser Ser Tyr Pro Leu Thr
1               5

<210> SEQ ID NO 7
<211> LENGTH: 10
<212> TYPE: PRT
<213> ORGANISM: Mus musculus

<400> SEQUENCE: 7

Gly Phe Thr Phe Ser Asp Ala Trp Met Asp
1               5                   10

<210> SEQ ID NO 8
<211> LENGTH: 9
<212> TYPE: PRT
<213> ORGANISM: Mus musculus

<400> SEQUENCE: 8

Ile Arg Ser Lys Ala Asn Asn His Ala
1               5

<210> SEQ ID NO 9
<211> LENGTH: 8
<212> TYPE: PRT
<213> ORGANISM: Mus musculus

<400> SEQUENCE: 9

His Arg Tyr Asp Gly Phe Asp Tyr
1               5

<210> SEQ ID NO 10
<211> LENGTH: 10
<212> TYPE: PRT
<213> ORGANISM: Mus musculus

<400> SEQUENCE: 10

Ser Ala Ser Ser Ser Ile Ser Tyr Met His
1               5                   10

<210> SEQ ID NO 11
<211> LENGTH: 7
<212> TYPE: PRT
<213> ORGANISM: Mus musculus

<400> SEQUENCE: 11
```

-continued

```
Asp Thr Ser Lys Leu Ala Ser
1               5

<210> SEQ ID NO 12
<211> LENGTH: 8
<212> TYPE: PRT
<213> ORGANISM: Mus musculus

<400> SEQUENCE: 12

Gln Arg Ser Ser Tyr Pro Cys Thr
1               5

<210> SEQ ID NO 13
<211> LENGTH: 373
<212> TYPE: DNA
<213> ORGANISM: Mus musculus

<400> SEQUENCE: 13
ggcagggagc ggtgaccgtg gtccctgcgc cccagacatc gaagtaccag tagctactac      60
cgtagtaatc ccttgcacag tagtacatgg ctgtgtcctc agacctcaga ctgctcattt     120
ccaggtacag ggtgttcttg gcattctctc tagagatggt gaatcggccc gtcacagtgt     180
ctgcatagta gatactatat gccaaattac taatgaatgc tacccactca ggcccccttcc     240 ctggagcctg tcgaacccac gccattccgt agtcactgaa agtgaatcca gaggctgcac     300
aggatagttt ccgggaccct ccaggctgca ctaagcctcc ccctgactcc tccagcttaa     360
cttgaccggt cga                                                        373

<210> SEQ ID NO 14
<211> LENGTH: 331
<212> TYPE: DNA
<213> ORGANISM: Mus musculus

<400> SEQUENCE: 14
gcaaccaatt cctgcatctc caggggagag gtcaccataa cctgcagtgc cagctcaagt      60
gtaagttaca tgcactggtt ccagcagaag ccaggcactt ctcccaaact ctggatttat     120
agcacatcca acctggcttc tggagtccct gctcgcttca gtggcagtgg atctgggacc     180
tcttactctc tcacaatcag ccgaatggag gctgaagatg ctgccactta ttactgccag     240
caaaggagta gttacccgct cacgttcggt gctgggacca agctggagct gaaacgggct     300
gatgctgcac caactgtatc cctcgagacc a                                    331

<210> SEQ ID NO 15
<211> LENGTH: 124
<212> TYPE: PRT
<213> ORGANISM: Mus musculus

<400> SEQUENCE: 15

Ser Thr Gly Gln Val Lys Leu Glu Glu Ser Gly Gly Gly Leu Val Gln
1               5                   10                  15

Pro Gly Gly Ser Arg Lys Leu Ser Cys Ala Ala Ser Gly Phe Thr Phe
            20                  25                  30

Ser Asp Tyr Gly Met Ala Trp Val Arg Gln Ala Pro Gly Lys Gly Pro
        35                  40                  45

Glu Trp Val Ala Phe Ile Ser Asn Leu Ala Tyr Ser Ile Tyr Tyr Ala
    50                  55                  60

Asp Thr Val Thr Gly Arg Phe Thr Ile Ser Arg Glu Asn Ala Lys Asn
65                  70                  75                  80
```

```
Thr Leu Tyr Leu Glu Met Ser Ser Leu Arg Ser Glu Asp Thr Ala Met
                85                  90                  95

Tyr Tyr Cys Ala Arg Asp Tyr Tyr Gly Ser Ser Tyr Trp Tyr Phe Asp
            100                 105                 110

Val Trp Gly Ala Gly Thr Thr Val Thr Ala Pro Cys
        115                 120

<210> SEQ ID NO 16
<211> LENGTH: 110
<212> TYPE: PRT
<213> ORGANISM: Mus musculus

<400> SEQUENCE: 16

Ala Thr Asn Ser Cys Ile Ser Arg Gly Glu Val Thr Ile Thr Cys Ser
1               5                   10                  15

Ala Ser Ser Ser Val Ser Tyr Met His Trp Phe Gln Gln Lys Pro Gly
                20                  25                  30

Thr Ser Pro Lys Leu Trp Ile Tyr Ser Thr Ser Asn Leu Ala Ser Gly
            35                  40                  45

Val Pro Ala Arg Phe Ser Gly Ser Gly Ser Gly Thr Ser Tyr Ser Leu
        50                  55                  60

Thr Ile Ser Arg Met Glu Ala Glu Asp Ala Ala Thr Tyr Tyr Cys Gln
65                  70                  75                  80

Gln Arg Ser Ser Tyr Pro Leu Thr Phe Gly Ala Gly Thr Lys Leu Glu
                85                  90                  95

Leu Lys Arg Ala Asp Ala Ala Pro Thr Val Ser Leu Glu Thr
            100                 105                 110

<210> SEQ ID NO 17
<211> LENGTH: 364
<212> TYPE: DNA
<213> ORGANISM: Mus musculus

<400> SEQUENCE: 17
cggggaatgt gagagtggtg ccttggcccc agtagtcaaa gccgtcgtac ctatgcctcg      60
tacagtaata aatgccagtg tcttcagctc ttaagctgtt catttgcagg tagacactac     120
ttttggaatc atctcttgag atggtgaacc tccctttcac agactcagca tagtatgttg     180
catgattatt agctttgctt ctaatttcag caacccactc aagcccttc tctggagact      240 ggcggaccca gtccatccag gcgtcactaa aagtgaatcc agaggcagca caagagagtt     300
tcatggatcc tccaggttgc accaagcctc ctcctgactc ctccagctta acttgaccgg     360
tcga                                                                  364

<210> SEQ ID NO 18
<211> LENGTH: 336
<212> TYPE: DNA
<213> ORGANISM: Mus musculus

<400> SEQUENCE: 18
gattattttc ttgcatctca gggagaggtc accatgacct gcagtgccag ctcaagtata      60
agttacatgc actggtacca gcagaagcca ggcacctccc ccaaaagatg gatttatgac     120
acatccaaac tggcttctgg agtccctgct cgcttcagtg gcagtgggtc tgggacctct     180
tattctctca caatcagcag catggaggct gaagatgctg ccacttatta ctgccatcag     240
cggagtagtt acccatgcac gttcggtgct gggaccaagc tggagctgaa acgggctgat     300
gctgcaccaa ctgtatccct cgagaccaag accagc                              336
```

-continued

```
<210> SEQ ID NO 19
<211> LENGTH: 121
<212> TYPE: PRT
<213> ORGANISM: Mus musculus

<400> SEQUENCE: 19

Ser Thr Gly Gln Val Lys Leu Glu Glu Ser Gly Gly Gly Leu Val Gln
1               5                   10                  15

Pro Gly Gly Ser Met Lys Leu Ser Cys Ala Ala Ser Gly Phe Thr Phe
                20                  25                  30

Ser Asp Ala Trp Met Asp Trp Val Arg Gln Ser Pro Glu Lys Gly Leu
            35                  40                  45

Glu Trp Val Ala Glu Ile Arg Ser Lys Ala Asn Asn His Ala Thr Tyr
        50                  55                  60

Tyr Ala Glu Ser Val Lys Gly Arg Phe Thr Ile Ser Arg Asp Asp Ser
65                  70                  75                  80

Lys Ser Ser Val Tyr Leu Gln Met Asn Ser Leu Arg Ala Glu Asp Thr
                85                  90                  95

Gly Ile Tyr Tyr Cys Thr Arg His Arg Tyr Asp Gly Phe Asp Tyr Trp
                100                 105                 110

Gly Gln Gly Thr Thr Leu Thr Phe Pro
            115                 120

<210> SEQ ID NO 20
<211> LENGTH: 112
<212> TYPE: PRT
<213> ORGANISM: Mus musculus

<400> SEQUENCE: 20

Asp Tyr Phe Leu Ala Ser Gln Gly Glu Val Thr Met Thr Cys Ser Ala
1               5                   10                  15

Ser Ser Ser Ile Ser Tyr Met His Trp Tyr Gln Gln Lys Pro Gly Thr
                20                  25                  30

Ser Pro Lys Arg Trp Ile Tyr Asp Thr Ser Lys Leu Ala Ser Gly Val
            35                  40                  45

Pro Ala Arg Phe Ser Gly Ser Gly Ser Gly Thr Ser Tyr Ser Leu Thr
        50                  55                  60

Ile Ser Ser Met Glu Ala Glu Asp Ala Ala Thr Tyr Tyr Cys His Gln
65                  70                  75                  80

Arg Ser Ser Tyr Pro Cys Thr Phe Gly Ala Gly Thr Lys Leu Glu Leu
                85                  90                  95

Lys Arg Ala Asp Ala Ala Pro Thr Val Ser Leu Glu Thr Lys Thr Ser
                100                 105                 110
```